United States Patent [19]

Adkisson et al.

[11] 4,000,417
[45] Dec. 28, 1976

[54] SCANNING MICROSCOPE SYSTEM WITH AUTOMATIC CELL FIND AND AUTOFOCUS

[75] Inventors: William M. Adkisson, Edina; Gerald D. Hunter, New Brighton; William M. Papic, Eden Prairie; Wayne L. Walters, Bloomington, all of Minn.

[73] Assignee: Honeywell Inc., Minneapolis, Minn.

[22] Filed: Aug. 25, 1975
(Under Rule 47)

[21] Appl. No.: 607,741

[52] U.S. Cl. .............................. 250/201; 356/39; 250/202; 250/222 PC; 235/92 PC
[51] Int. Cl.² .................. G01J 1/20; G05B 1/00
[58] Field of Search ............... 356/39, 125, 40; 250/201, 202, 222 PC, 461 B; 235/92 PC; 318/565, 577

[56] References Cited
UNITED STATES PATENTS

| | | | |
|---|---|---|---|
| 3,622,797 | 11/1971 | Bragg | 250/201 |
| 3,780,298 | 12/1973 | Agadzhanian et al. | 250/202 |
| 3,783,269 | 1/1974 | McConnell | 250/201 |
| 3,851,972 | 12/1974 | Smith et al. | 356/39 |
| 3,864,564 | 2/1975 | Adkins | 250/201 |
| 3,896,304 | 7/1975 | Aoki et al. | 250/201 |
| 3,916,205 | 10/1975 | Kleinerman | 356/39 |

*Primary Examiner*—Alfred E. Smith
*Assistant Examiner*—David K. Moore
*Attorney, Agent, or Firm*—Omund R. Dahle

[57] ABSTRACT

A scanning automated microscope system is designed as a clinical laboratory instrument which will aid and speed the task of the medical technologist in performing leukocyte differential count and red blood cell morphology studies. The microscope system has automatic stage drive which operates along the x, y, and z axes and an automated cell find system such that the leukocytes on normally prepared Wright stained slides are located automatically along a conventional meander search pattern, the found leukocytes are centered in the field of view, and are focused automatically. These cells can be observed on a color TV monitor and/or through the microscope oculars.

32 Claims, 54 Drawing Figures

OSC. DISPLAY DURING AUTO FOCUS

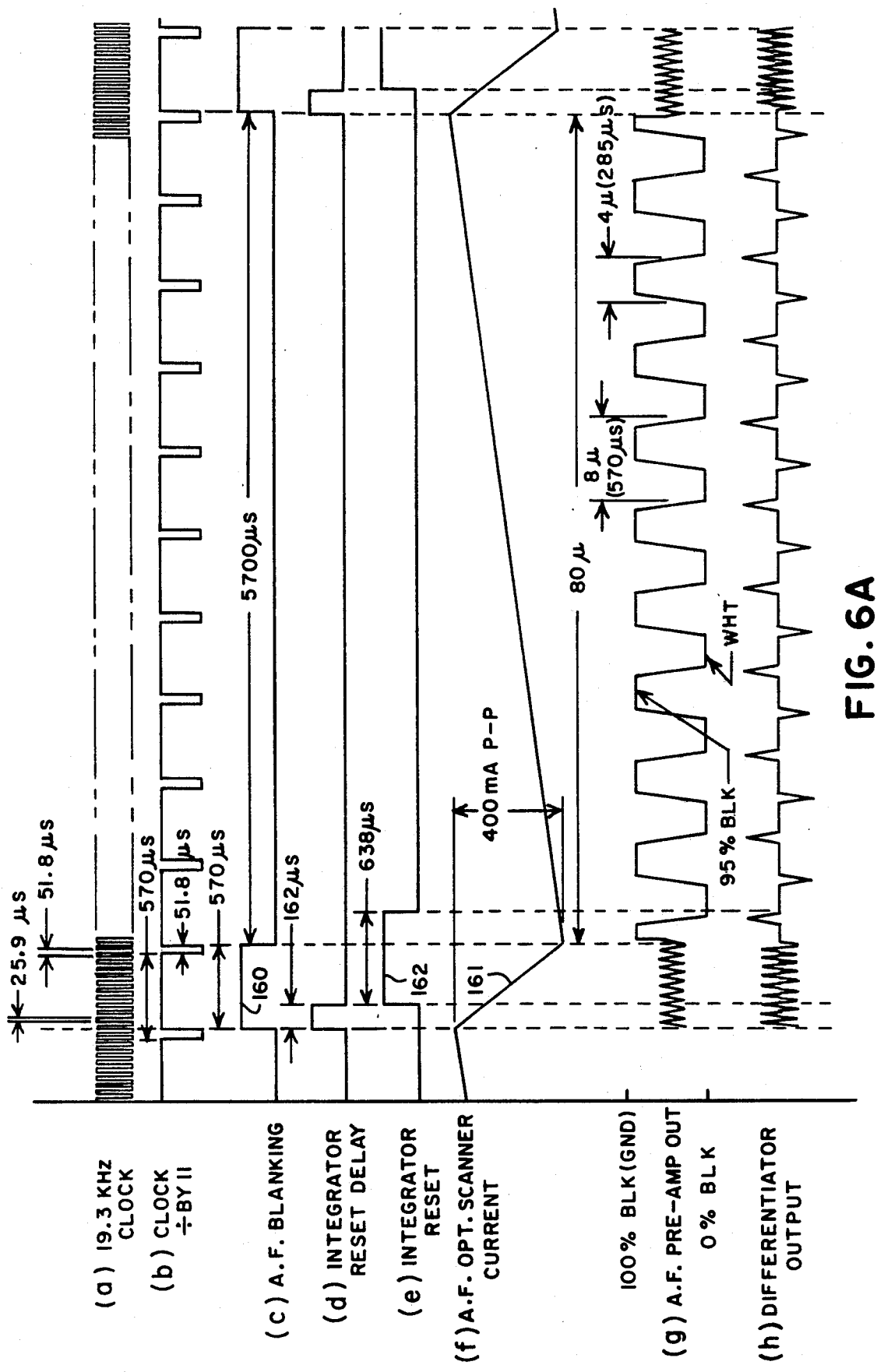

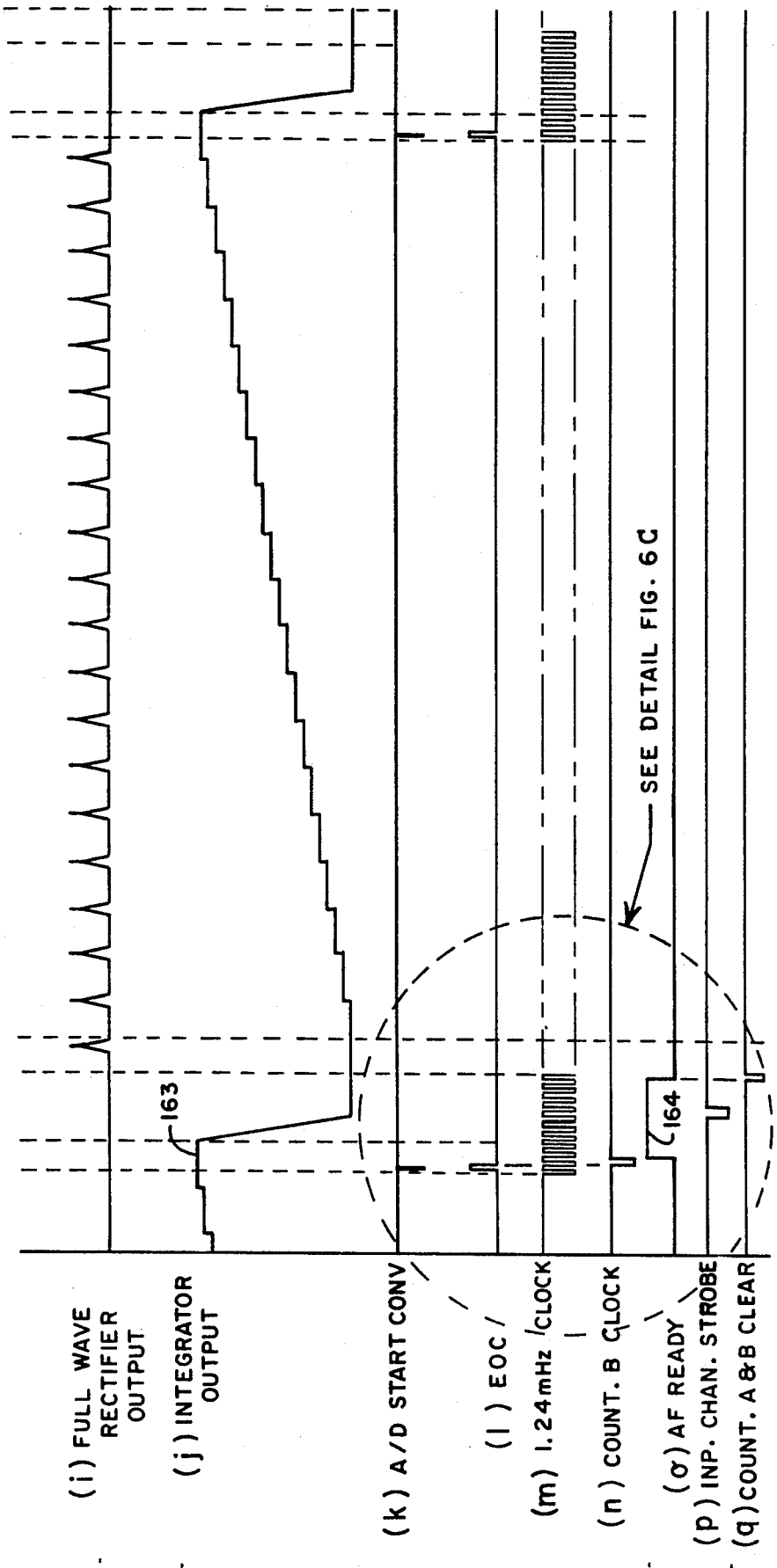

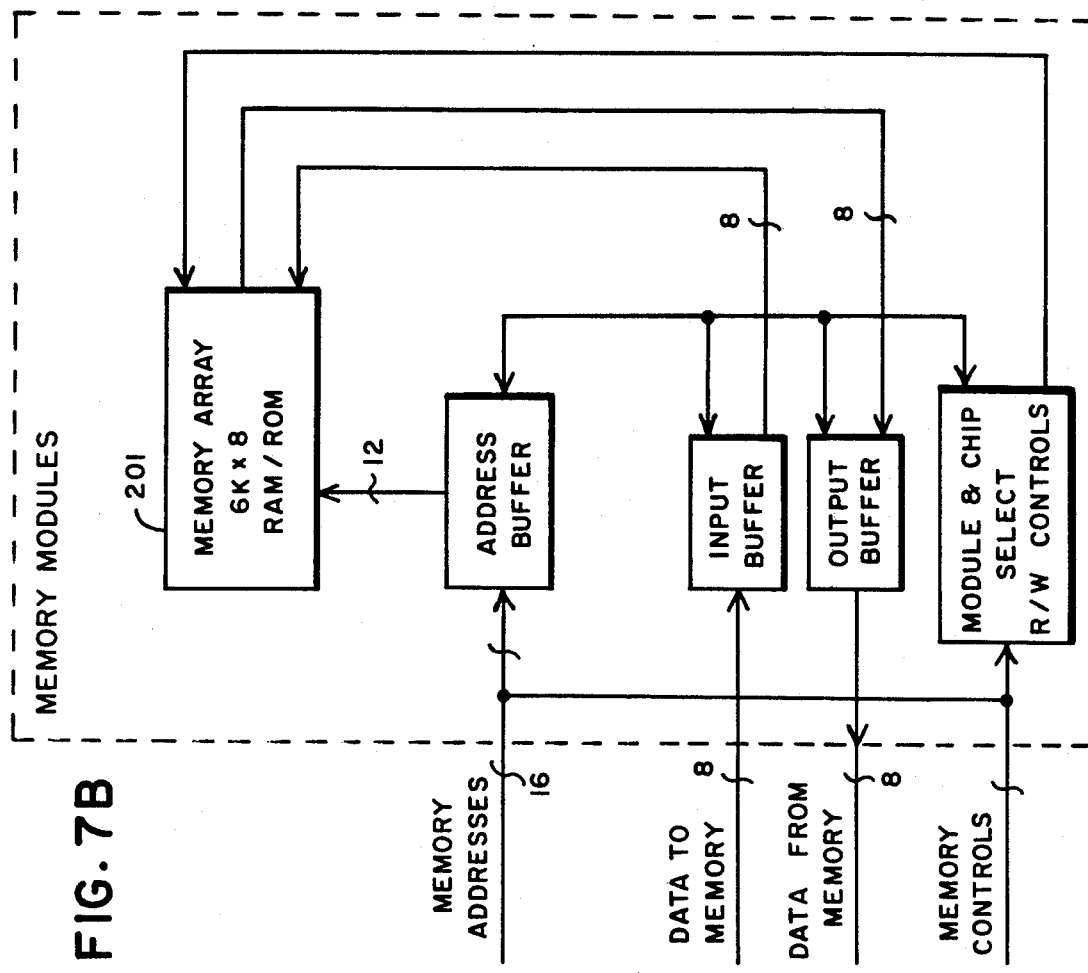

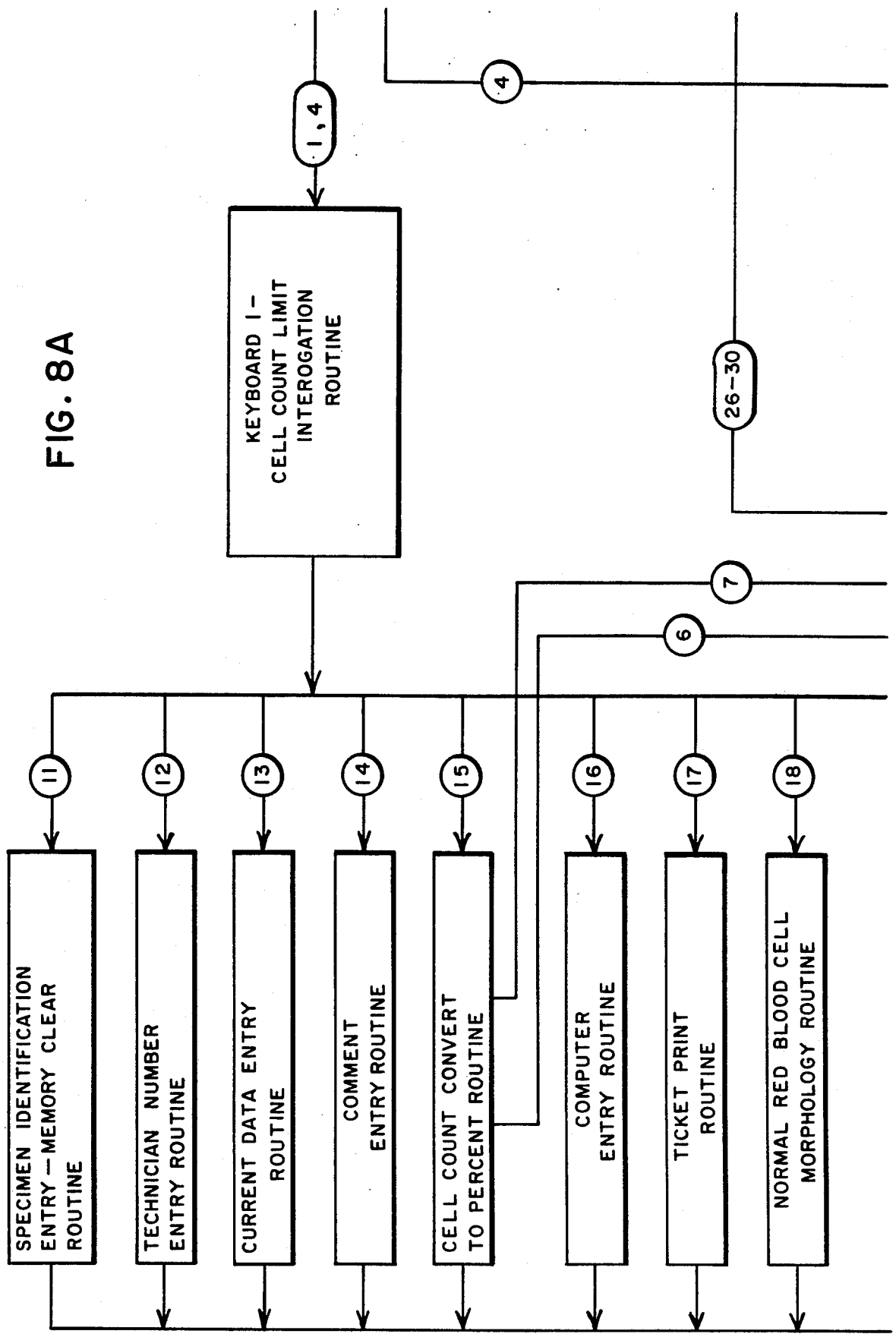

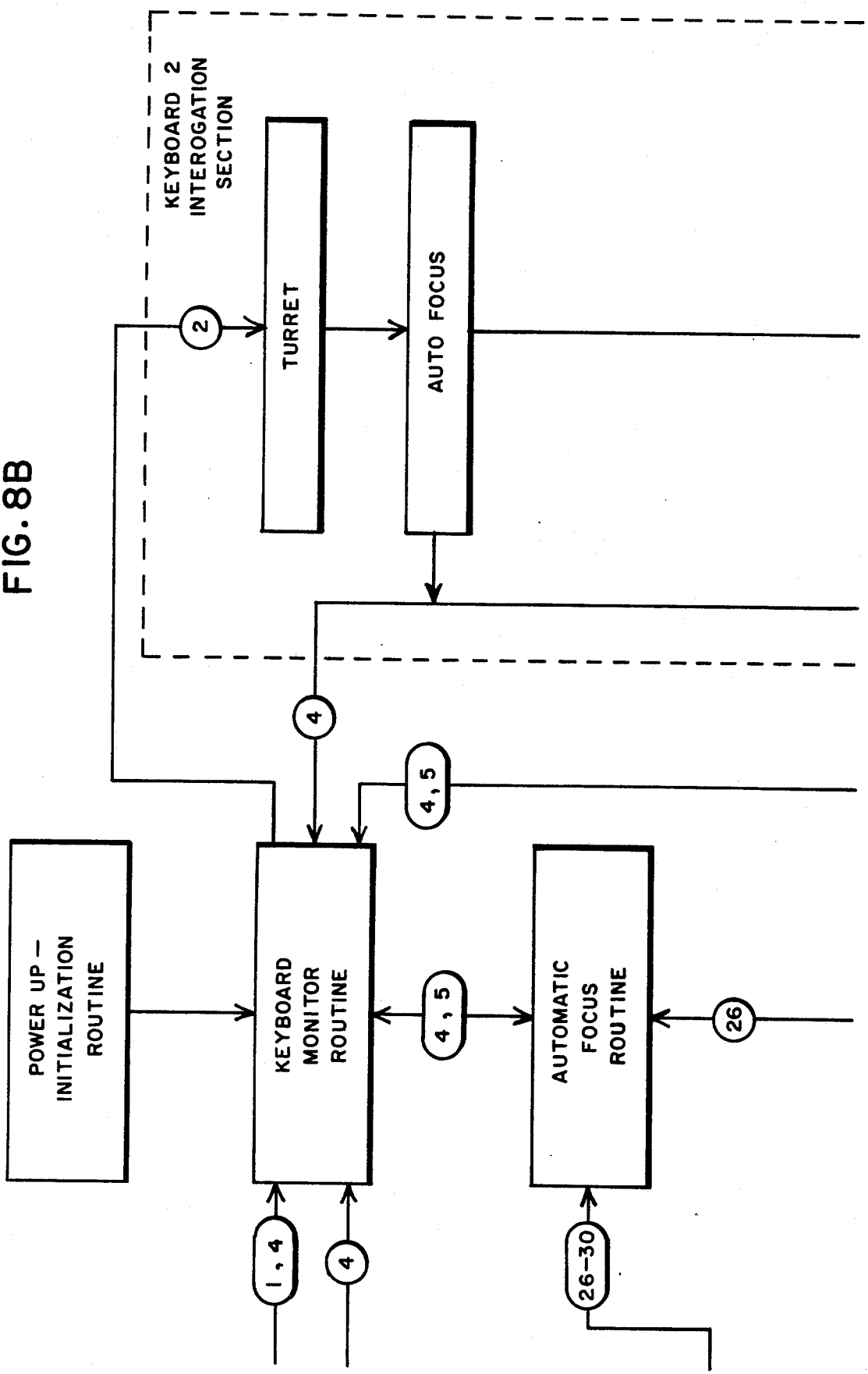

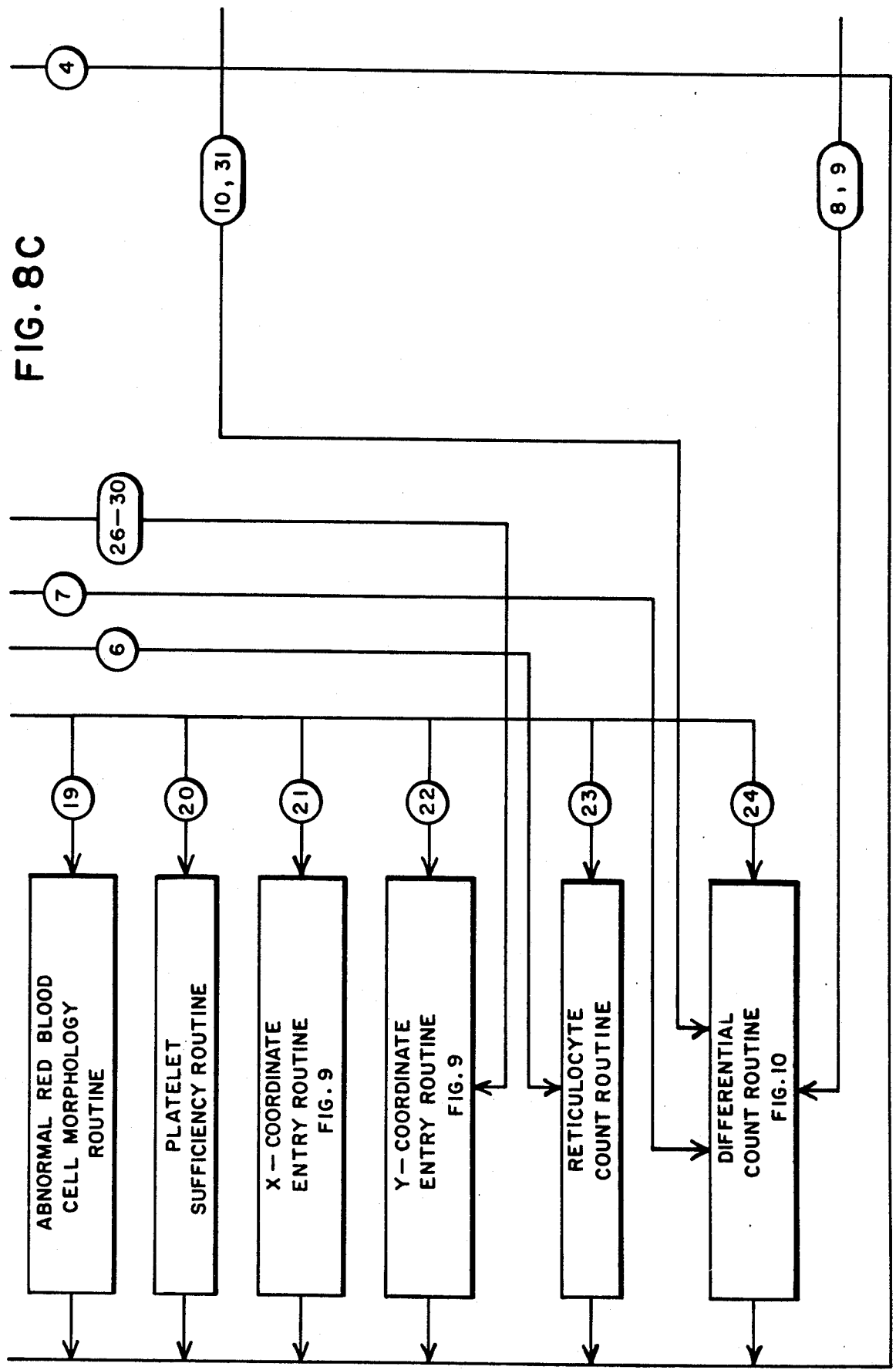

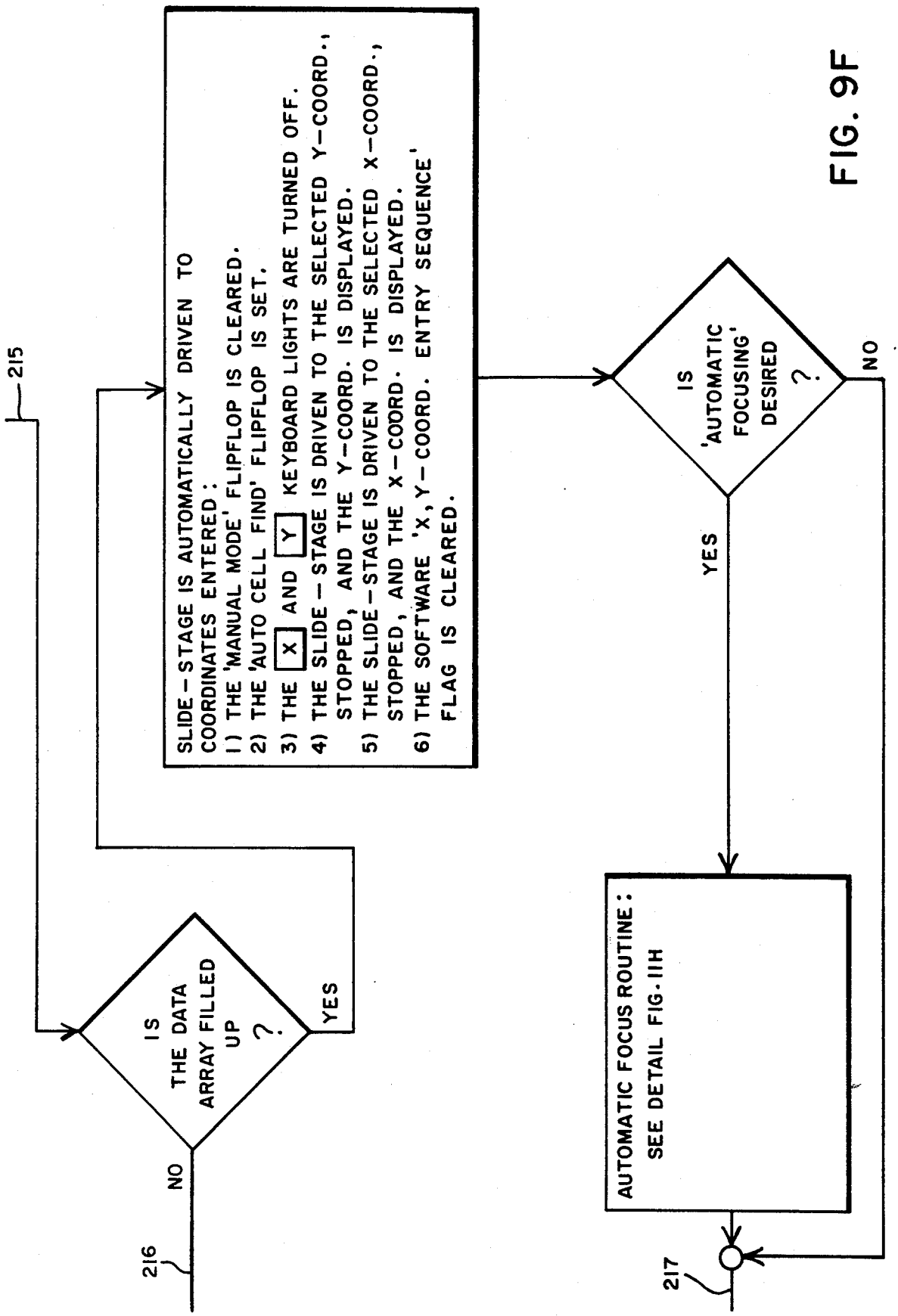

(27)

THE CELL IS CENTERED ON THE T-V MONITOR:
1) THE CELL'S POSITION RELATIVE TO THE MEANDER PATH IS USED TO DETERMINE THE X-MONITOR COMMAND.
2) THE CELL IS CENTERED ON THE T-V MONITOR AND THE SLIDE IS STOPPED.

(28) 241

THE PROCESS TO CENTER A CELL ON THE T-V MONITOR IS BEGUN HERE. THE NUMBER OF ENCODER PULSES, THE CELL LIES OFF THE MEANDER PATH, IS PICKED

IS THE CELL ALREADY ROUGHLY AT CENTER ?

NO

YES (29)

THE CURRENT X,Y COORDINATES ARE READ AND DISPLAYED.

IS 'AUTOMATIC FOCUSING' DESIRED ?

YES 239

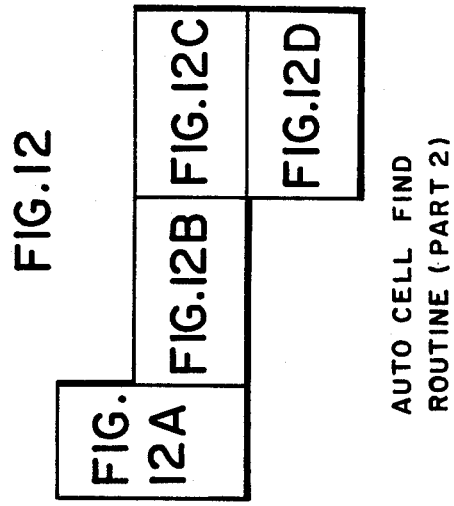
FIG. 12
AUTO CELL FIND ROUTINE (PART 2)
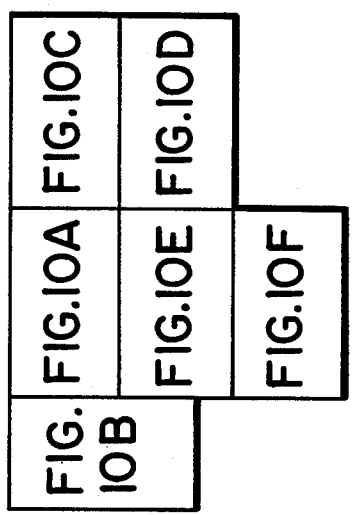
FIG. 10
KEYBOARD I: DIFFERENTIAL COUNT ROUTINE
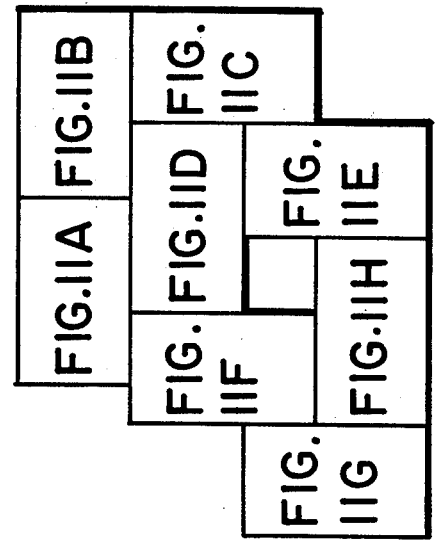
FIG. 11
AUTO CELL FIND ROUTINE (PART 1)
FIG. 8
| FIG.8A | FIG.8B |
|---|---|
| FIG.8C | FIG.8D |
SOFT WARE OPERATING SYSTEM
FIG. 9
| FIG.9A | FIG.9B |
|---|---|
| FIG.9C | FIG.9D |
| FIG.9E | FIG.9F |
X & Y COORDINATE ENTRY ROUTINES

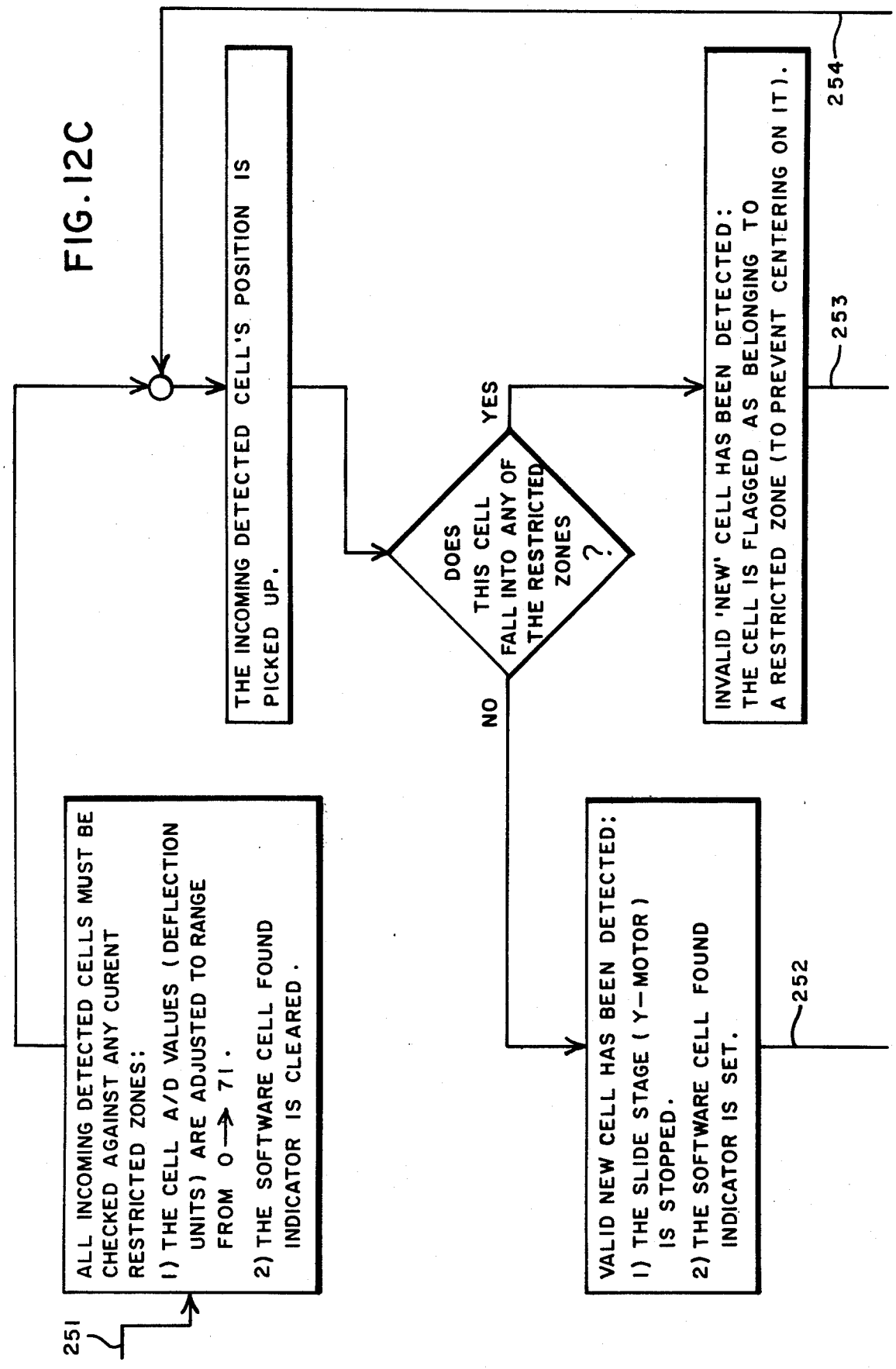

FIG. 14

SCANNING MICROSCOPE SYSTEM WITH AUTOMATIC CELL FIND AND AUTOFOCUS

BACKGROUND OF THE INVENTION

This invention relates to the field of microscopic examination of objects, one important example of which is leukocyte differential counts, i.e., the identifying and counting of the different types of white blood cells as well as red blood cell morphology studies. Since the task of finding or locating the desired blood cells on the slide is time consuming and tedious, there has been considerable effort expended previously in the area of automatically searching for and finding blood cells. One such reference is the Smithline U.S. Pat. No. 3,315,229, and there are other patents disclosing various details of automated blood study, for example, the Preston, Jr. et al U.S. Pat. No. 3,503,684, and Amos U.S. Pat. No. 3,806,257, and the Adkins U.S. Pat. No. 3,864,564.

SUMMARY OF THE INVENTION

Generally stated, the instrument is an automated computerized scanning system that enables the operator to perform leukocyte differential counts, red blood cell morphology studies, and platelet sufficiency estimates with greater speed and less fatigue than in previous methods. Although primarily designed for differential counts, the system also can be used for other blood examinations; for example, reticulocyte counts and bonemarrow studies. It may also be used to perform microscopic examinations in histology, cytology, microbiology, and clinical cytogenetics.

It automates routine functions, allowing the operator to concentrate on cell identification. The instrument finds white cells automatically and displays them on a color TV monitor for easy viewing and identification. Identification is made easy because the cells are presented several thousand times their actual size on a color TV monitor. The white cells appear as fast as the operator can identify them. As a teaching aid, the color TV provides medical students and technologists with a magnified view of the cells. It allows the instructor to point out specific cell characteristics to the entire class.

Data for each slide is stored in the memory system until the count is complete and printed out on the report form. Automatic recall, built into the instrument relocates specific cells on command. If suspect cells need further examination, the operator simply notes the displayed $x-y$ co-ordinates. The slide then may be removed. When the supervisor or pathologist is ready to review the slide, it is re-inserted and the co-ordinate position recalled by pressing the appropriate keys. The cell in question is automatically found for review. Work in the hematology lab flows along smoothly and the pathologist or supervisor doesn't have to be interrupted frequently for critical studies of abnormal cells. Because of this unique recall ability, slides may be transferred from one instrument to another.

In system operation generally, we place a conventionally prepared slide on the stage, position the slide over the good area and enter the specimen identification number using the data entry keys. The instrument is now ready for automatic function. Cells are automatically located and focused for the operator to identify. After the operator makes the identification, the next cell is presented in three-tenths of a second. The leukocyte count is stored in the instrument computer for later printing. At any time, complete RBC morphology comments and platelet sufficiency estimates may be entered into the instrument computer. After completing the differential, the results are printed on the report form.

In this invention a light source and microscope optics direct a light beam through a laboratory slide to a color TV camera. A first beam splitter directs a portion of the beam to the observer's oculars and a second beam splitter directs a further portion of the beam to automatic cell-find and automatic focus apparatus. An oscillating optical scanner in the path of the last mentioned beam portion provides a continuing sweep or scan across the field of view and presents the scanned light intensity representing the optical image to light responsive means such as photodiodes in the automatic cell-find and focus apparatus so that the light contrast of the scene is received. In the cell-find mode, the microscope "stage" carrying the slide is automatically driven along a traditional meander path or search pattern by the $x$ and $y$ stage drive motors. The cellfind apparatus makes use of the oscillating optical scanner during the stage automatic meander motion. The light responsive means and electronic circuit operate in conjunction with a digital computer to identify and store the $x-y$ address of leukocytes. Upon acquisition of a leukocyte in the meander path, the stage is caused to center the optic axis over the leukocyte address. When the stage stops over a leukocyte, the automatic focus apparatus activates to make use of the ocsillating optical scanner sweep, light responsive means, circuit and $z$-axis stage drive to automatically focus on high contrast objects (such as red cell edges) which lie in the observed region of the sweep and in the plane of the leukocyte. After the observer recognizes and identifies the type of leukocyte, the stage drive is directed to resume the prescribed meander search pattern to find the next leukocyte.

BRIEF DESCRIPTION OF THE DRAWINGS

FIGS. 6a, 6b, and 6c, is a graphical presentation of wave forms as related to the auto focus apparatus of FIG. 3, (i.e., a timing diagram);

FIGS. 7a and 7b is a block diagram of pertinent portions of the microprocessor shown in FIGS. 1 and 3;

FIG. 8, including FIGS. 8a, 8b, 8c, and 8d, is a general flow diagram of the systems operation;

FIG. 9, including FIGS. 9a, 9b, 9c, 9d, 9e, and 9f, is a flow of $x$ and $y$ coordinate entry routines;

FIG. 10, including

FIG. 11, including FIGS. 11a, 11b, 11c, 11d, 11e, 11f, 11g, 11h, is a flow diagram of automatic cell-find routine (Part 1);

FIG. 12, including FIGS. 12a, 12b, 12c, and 12d is a flow diagram of automatic cell-find routine (Part 2);

FIG. 14 is a pictorial view of the keyboard.

DESCRIPTION OF THE PREFERRED EMBODIMENTS

Figure 1:
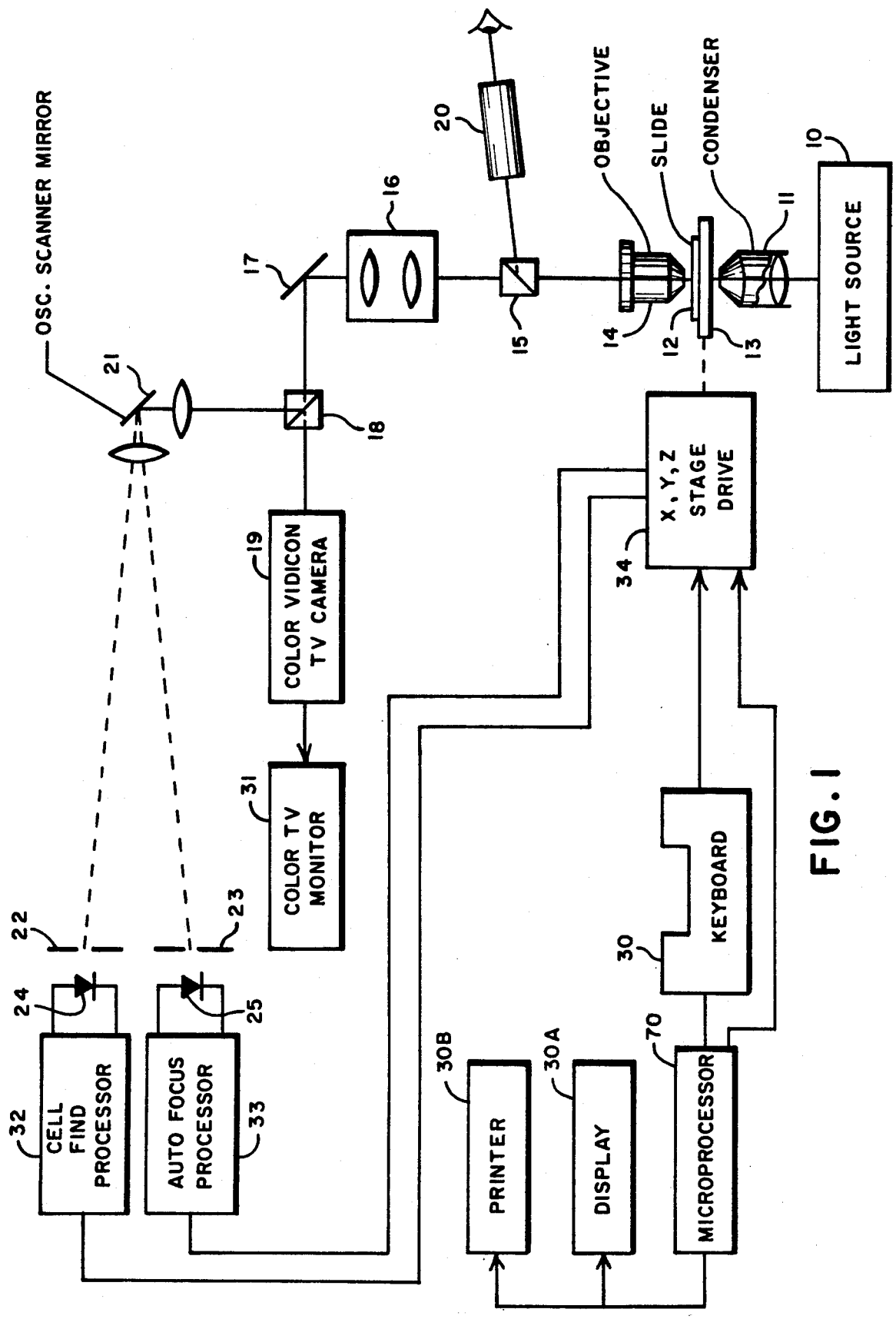
FIG. 1 is a functional block diagram of the scanning automated microscope system.

Referring to FIG. 1, there is a disclosed a system for automatically scanning, stopping and focusing on desired blood cells on a blood slide. The light from a light source 10 passes through microscope condenser lenses 11 and through a slide 12 which is positioned on a microscope stage 13. Standard objective lenses 14 collect the light which then passes through a beam splitter 15, through imaging lens assembly 16, mirror 17, and through a second beam splitter 18 to a color vidicon TV camera 19 which together with a monitor provides a real time presentation to the observer. The TV camera may be a Toshiba Model 1K-12, and the TV monitor may be a Sony Model KV-5000. The first beam splitter 15 reflects a portion of the light to operator oculars 20. The beam splitter 18 reflects a further portion of the light beam to an optical scanner 21, which may be an oscillating galvanometer mirror, and then through a pinhole aperture or apertures 22 and 23 to light responsive means 24 and 25, here shown as photodiodes. The oscillating optical scanner provides a continuously recurring scan across the optical field of view to the cell-find diode 24 and the focusing diode 25. Although the photodiodes 24 and 25 have been shown relatively far apart in FIG. 1 for clarity, it will be understood that they may be placed in close proximity. If desired, a single photodiode may be the light responsive means for both cell-find and auto-focus operations.

Figure 13:
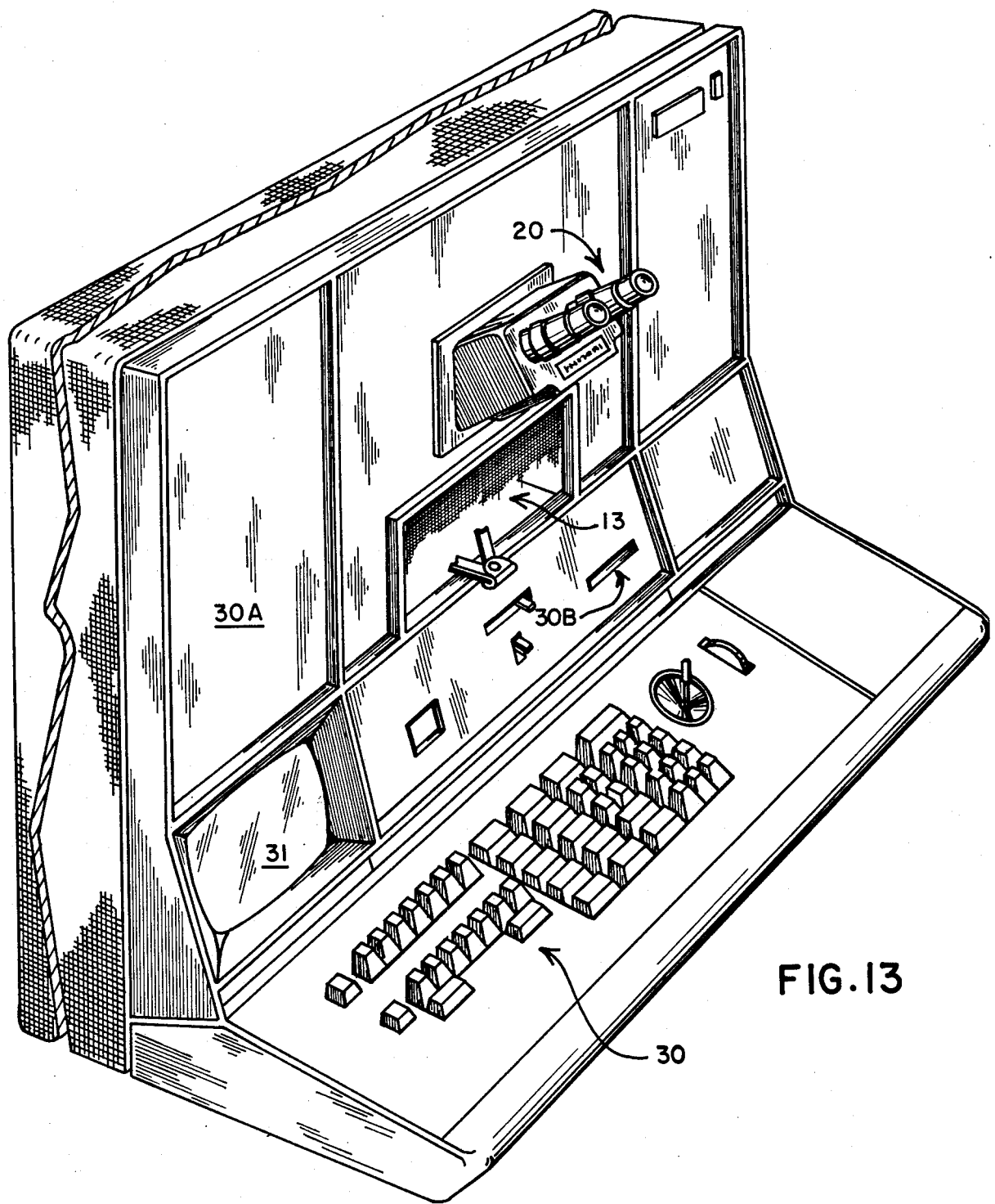
FIG. 13, is a pictorial view of the instrument.

A keyboard 30 (shown pictorially in FIGS. 13 and 14) allows the medical technologist or observer to control all scanning automated microscope system operations and to make extra data entries. Some of these operations include entry of initial test related information, automatic leukocyte finding and focus, manual stage control and manual control focus, display 30A and data printout at printer 30B. The printer may be of the general type of Model No. C-8304 by ITT-General Controls. The color vidicon TV camera 19 is a part of a color TV subsystem which also includes a camera control unit and a color TV monitor 31, the color TV in conjunction with the microscope providing real time, and true color representation of the cells being observed.

The electrical output of photodiode 24 is passed on to a cell-find processor 32, the output of which is connected to the x–y stage drive 34. The electrical signal from auto-focus diode 25 is utilized by auto-focus processor 33 to actuate the z-axis of the stage drive 34 and to bring into proper focus a cell which has been found, centered and stopped over. The auto-focus system is inhibited during the cell-find operation.

Figures 2, 2A, 2B:
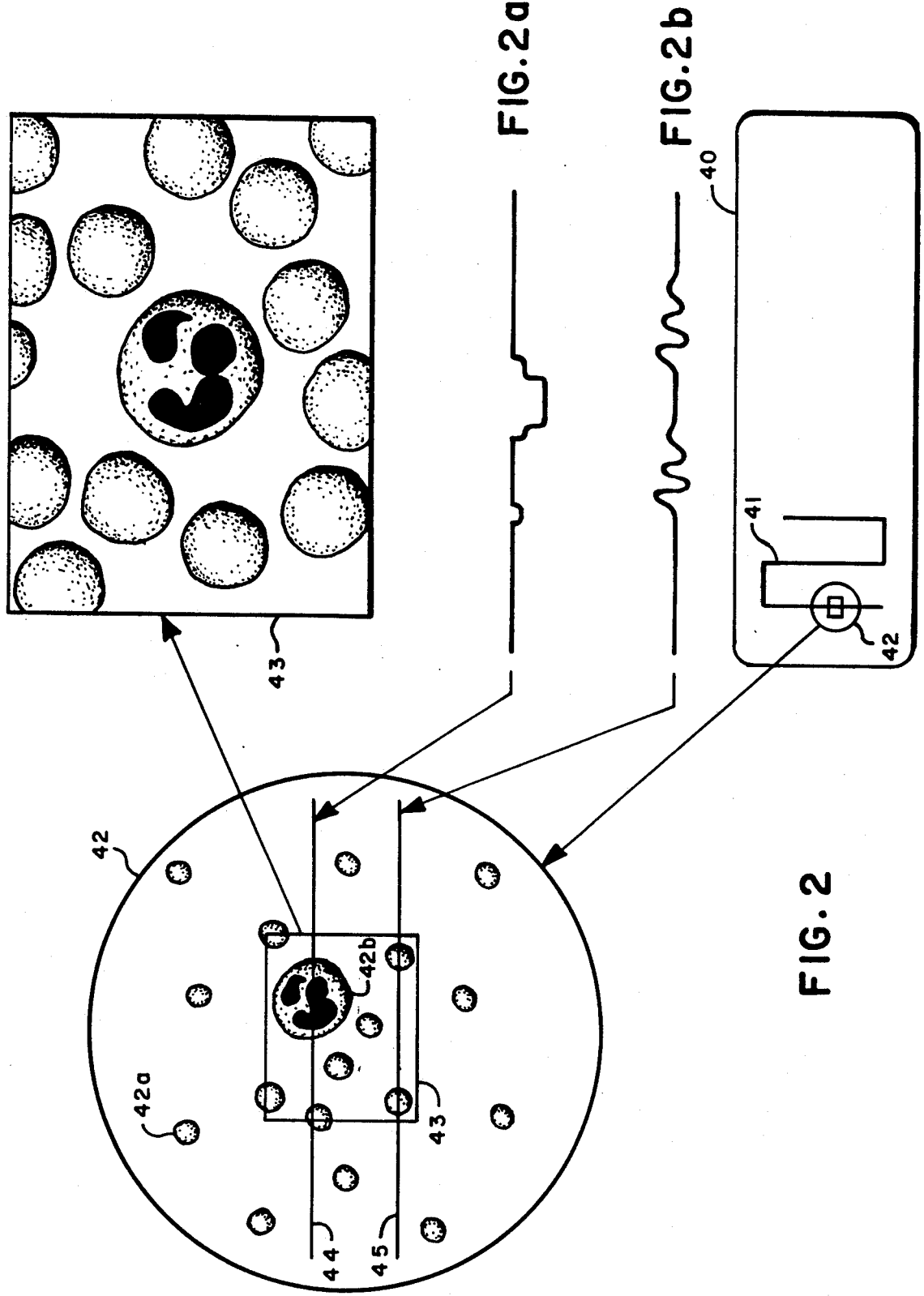
FIG. 2 is a twice exploded view of the microscope slide, search meander path, optical field of view and TV display.
FIGS. 2a and 2b are representative electrical wave forms related to FIG. 2.

Referring now to FIG. 2, there is disclosed a twice exploded or enlarged view of a blood smeared glass slide. The lower right hand portion of the figure depicts the standard 1 inch by 3 inches glass slide 40 which has superimposed thereon a line representing a typical meander pattern 41 followed by the microscope stage as the cell-find mode progresses while looking for leukocytes. Of course, the meander pattern can continue to the right as far as desired or other meander patterns can be chosen. The circular area 42 on the slide represents a typical field of view of the optical system as a particular period of time and can be seen by the observer looking through the oculars 20.

At the left of FIG. 2, the circular field of view 42 is magnified or enlarged to show a number of red cells 42a (small circles) and a leukocyte 42b (larger circle) which are in view at this point of the meander. In the center of the field of view is a rectangular area 43 which represents the more limited field of view of the TV camera. A horizontal line 44 across the center of the field of view represents the portion of the scene which is being optically scanned (i.e., an optical sweep) by the oscillating optical scanner 21 and presented to the cell-find photodiode 24. A similar line 45 may represent the portion of the field of view scanned for the auto-focus. Although line 45 is shown as dimensionally separated from line 44 and as scanning a different portion of the field of view for illustrative purposes, the photodiodes can equally as well be positioned so that the two lines 44 and 45 observed by the two photodiodes overlie one another. The field of view 43 is further magnified or enlarged in the upper right of FIG. 2 to reproduce a photograph taken of the TV presentation in which a leukocyte is centered and is surrounded by a number of red blood cells.

The observer has the option of viewing the blood cells by means of the color TV monitor 31 and/or the osculars 20. The optical scans 44 and 45 when projected to the light responsive means 24 and 25 and the associated control circuits are converted to electrical signals representing the optical characteristics of the cells encountered. FIGS. 2a and 2b at the center right are examples of such converted signals for cell-find and for auto-focus, respectively. It will be observed from FIG. 2a that the dark nucleus portion of the leukocyte results in a larger signal amplitude change which can be recognized by the cell-find circuit.

Figure 3:
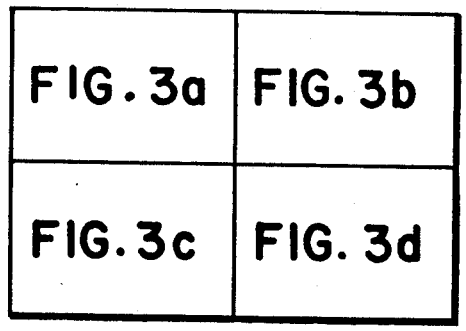
FIG. 3, including

Referring now to FIG. 3, which is an assembly of FIGS. 3a, 3b, 3c, and 3d, the automatic focus processor 33 and cell-find processor 32 is shown in a more detailed block diagram form. As previously described more generally, a light source 10 provides a beam through the microscope and a portion of the beam reaches the oscillating optical scanner mirror 21'; and is transmitted through the apertures 22 and 23 to the photodiodes 24 and 25 so that the photodiodes receive a continuing series of optical sweeps as represented by lines 44 and 45 of FIG. 2.

During the cell-find operation for leukocytes, the y axis motor drives continuously until a leukocyte is found, to advance the slide in the y direction along the prescribed meander path about 4μ (microns) per sweep. When a leukocyte is located, the y motor stops, the x motor drives the stage left of right to center over it optically and stops, whereupon automatic focus then occurs, the z-axis motor then operative to drive the stage in the z-axis or vertical direction. Cell-find only occurs during y motor and during the time increment when the x motor is transferring the stage to a new meander line there is no cell-find occurring. When a cell has been located and the x motor drives from the meander line to center the cell in the optics, the microcomputer retains the meander line position information and returns the stage to it before search starts again. During the auto-focus, a sawtooth scan (FIG. 6, curve f) of the optical scanner directs to the auto-focus diode an optical sweep which includes a number of red cells providing rate of changes in light intensity (FIG. 2b) across the sweep. The more accurately the microscope is focused, the sharper the rate of change signal becomes. Said another way, the automatic focus system depends on traversing cell edges which fall in the observed scan line to obtain rate of change signals.

The x, y, z axis stage drive comprises three servo motors of a known type such as Honeywell Inc., Microswitch Division, motor-tachometer. Identification No. 91929 (catalog lising 2VM61-033-4). Encoders are mounted on the servo motors to provide precise $x$–$y$ coordinates of the location of particular leukocytes into the microprocessor storage and to provide capability for automatic return of the stage of these coordinates to represent selected leukocytes for further visual observation. The $x$–$y$ coordinates of the current stage position are visually presented on the operator's display panel. Encoders being used on this apparatus are Model 992-200-O-C-L-P by Disc Instruments Inc. of Costa Mesa, California, installed on the Honeywell servometers.

The Display Panel 30a provides indication of numerous items including the (1) Cell Count which indicates the total number of cells counted; (2) NRBC/100WBC indicating the number of normal red blood cells counted or the NRBC's per 100 white blood cells when the Convert to % key is pressed or the cell count limited is reached; (3) Differential Tally which indicates the number of leukocytes counted for each of the twelve leukocyte types, or percent when the Convert to % key is pressed or when cell count limit is reached; and, (4) coordinates which indicate the current stage position through $x$–$y$ coordinates.

The automatic cell-find and auto-focus circuits operate either in an auto-focus mode or in a cell-find mode but not both simultaneously. Mode switching is provided by the microprocessor 70 to allow multiplexing of some of the electronic circuit such as the analog/-digital converter 55, the analog/digital output register 58 and the microprocessor interface circuits as well as the optical scanner 21 and its drive electronics 85. The auto-focus mode and the automatic cell-find mode are selected at the keyboard, and this selection puts mode switching under control of the microprocessor.

Figure 3A:
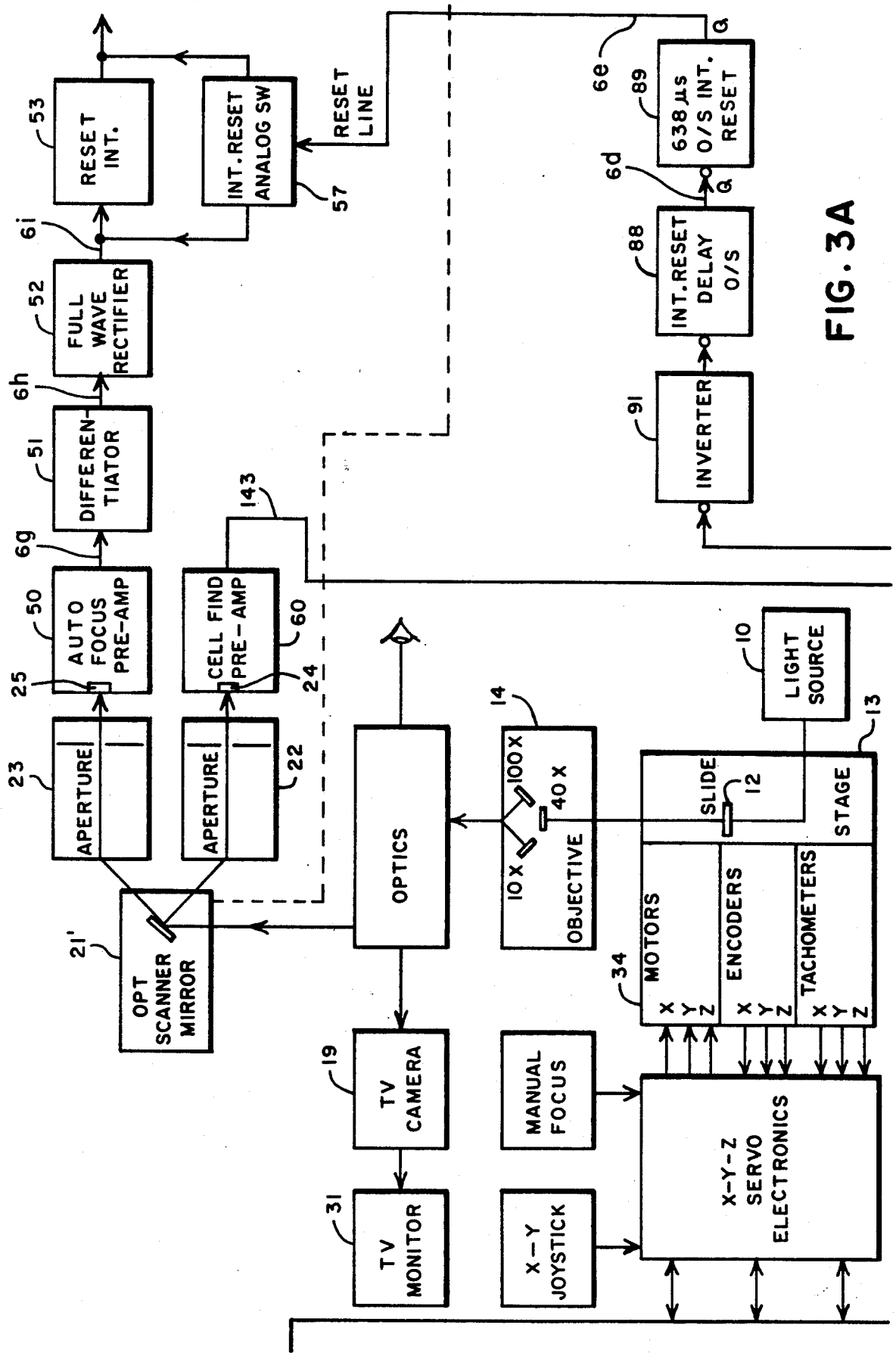
FIGS. 3a, 3b, 3c, and 3d, is a more detailed block diagram of the auto-focus and cell-find apparatus.
Figure 3B:
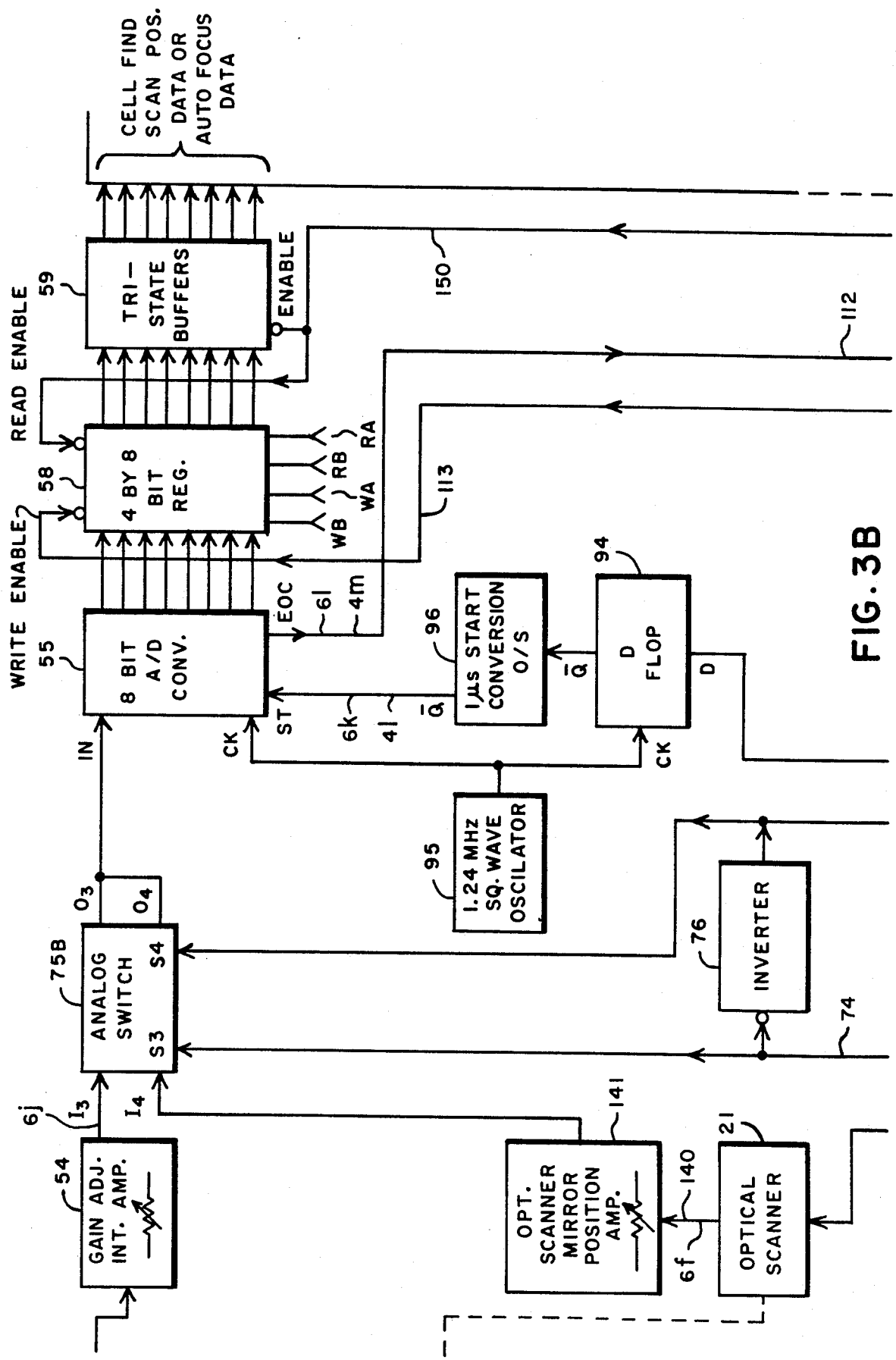
Figure 3C:
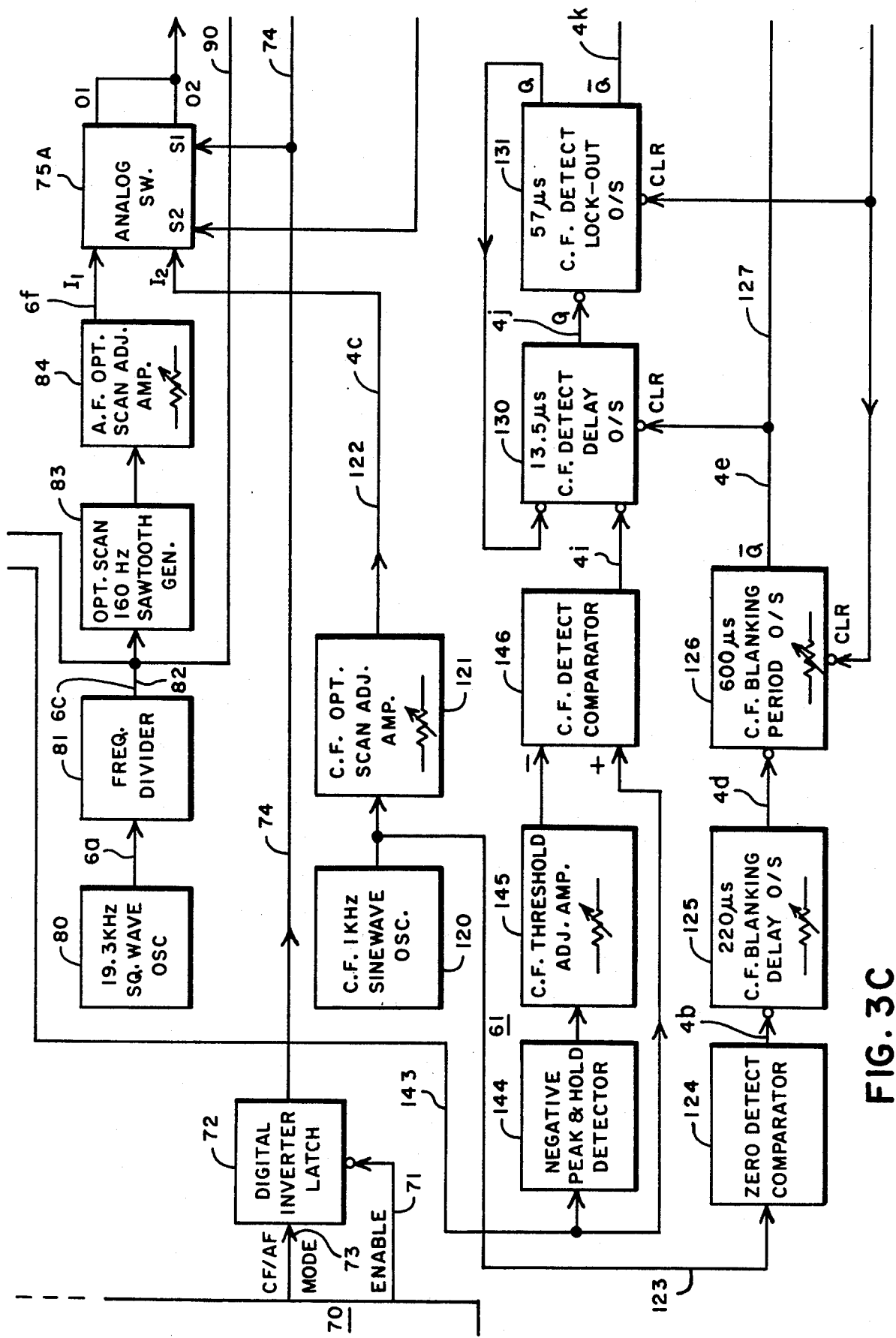
Figure 3D:
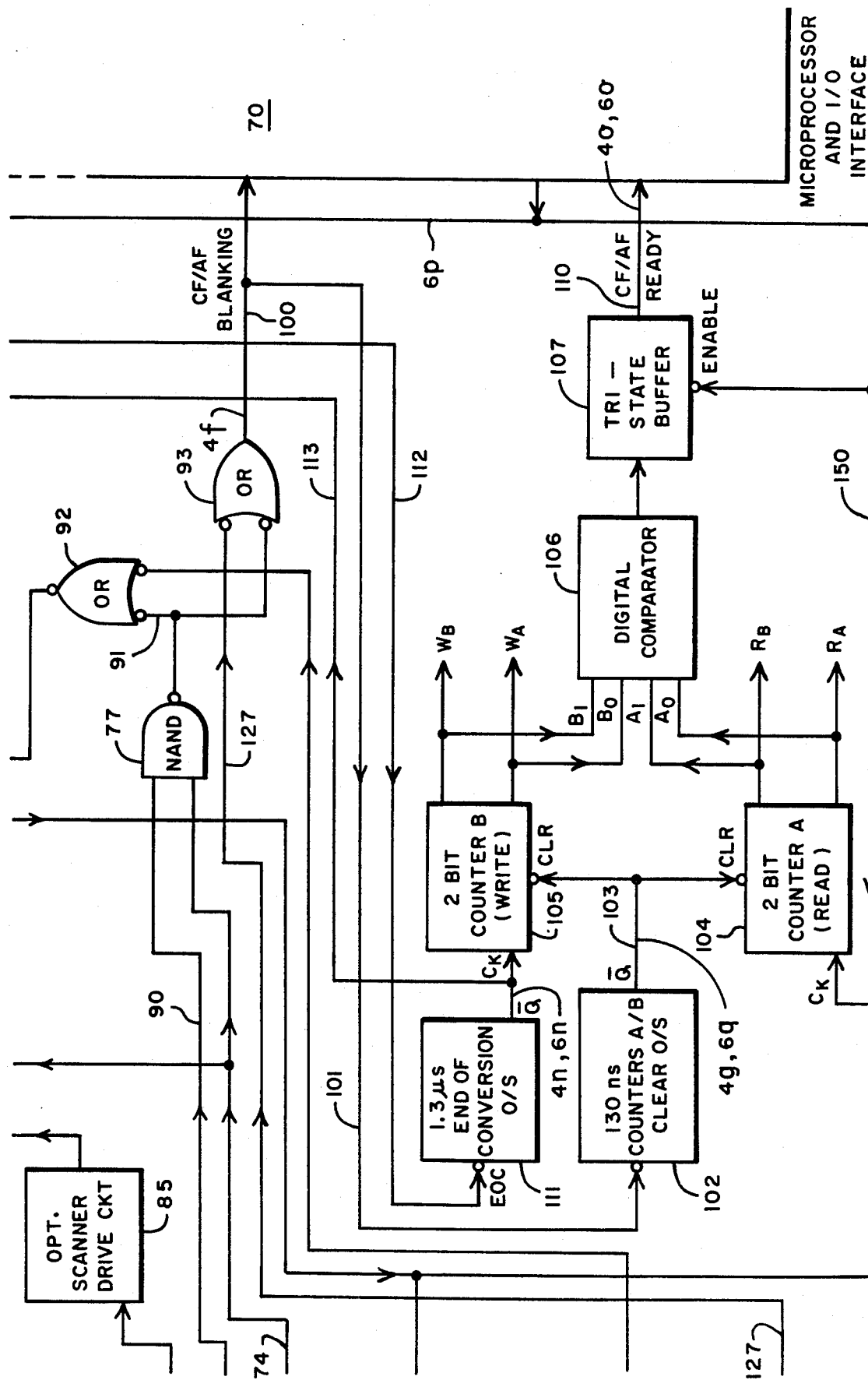

To control the operation of the auto-focus and automatic cell-find circuits from the microprocessor 70, an enable line 71, shown in FIG. 3c, provides a pulse to engage digital inverter latch 72. When the digital inverter latch is so activated, a logic 0 at the input 73 of the latch provides a logic 1 out and causes the autofocus circuits to be active, while a logic 1 at terminal 73 causes the automatic cell-find circuits to be active.

AUTO-FOCUS

Automatic focus routine after every cell-find even though the last good focus position, i.e., the focus setting from the previous auto-focus, may be adequate. The slide-stage is driven down (−z direction) two microns. The slide stage is then driven up (+z direction) four microns while the focus A/D value is read at every half micron interval, i.e. scan coincides with a half micron advance in the z direction. The maximum A/D value and its location are noted in the microprocessor 70. The maximum A/D value is compared against an upper and lower threshold and if the A/D value is within limits, the slide stage is driven down to the selected new good focus location. If the A/D value fails the threshold test, the slide stage is driven down to the last good or optimum focus position. This automatic focus routine occupies about 100 milliseconds.

Referring first to the auto-focus processor, the flow of the electrical signal is as follows: The light falling on photodiode 25 is converted to an electrical signal which is connected to amplifier means 50, the output of which is differentiated at differentiator 51, full-wave rectified at 52, and the resulting pulses are integrated at reset integrator 53. The aperture 23, light responsive means 25, preamp 50, differentiator 51, integrator 53, and A/D converter 55 work together to provide an optical to electrical transducer, or more specifically, a light intensity rate of change to voltage transducer. In the normal auto focus mirror scan, many red cells are crossed (only two of which are shown in FIG. 2, scan line 45), each cell edge providing a rapid rate-of-change in light intensity reaching light responsive means 25.

The plasma surrounding the red cells is much more transparent then the red cells so that as the scan crosses cell edges, a rapid rate of change of light intensity is seen by the light responsive means 25. The more closely optimum focus is achieved, the sharper is the cell edge produced rate-of-change signal. The aperture 23 used for auto-focus is very small, i.e. $\approx 0.5$ micron diameter compared to red cell diameter of $\approx 4$ microns, so that the cell edge sharpness is accentuated. The sharper the rate-of-change of light intensity at sensor 25, the larger will be the output pulses of differentiator 51 to be integrated. The integrated signal is further amplified as needed at gain adjustable integrator amplifier 54 (FIG. 3b), coupled through analog switch 75B and converted to a digital value in the A/D converter 55 when switch 75B is in position to transmit auto-focus data. The control of switch 75 is further discussed below. Analog switch 75 comprises block 75a with its two inputs $I_1$ and $I_2$ and block 75b with its two inputs $I_3$ and $I_4$. The analog switch 75 may be operated to one position in which the inputs $I_2$ and $I_4$, respectively, are connected through to their respective outputs, or to the opposite switched condition in which inputs $I_1$ and $I_3$ are connected to their respective switch outputs.

Thus, as will be described further, the analog switch 75a accepts a 160 Hz sawtooth drive during auto-focus and accepts a 1000 Hz sine wave drive during cell-find to provide two different drives to the optical scanner 21. At the same time, the analog switch 75B provides auto-focus scanning information to the converter 55 during auto-focus, and provides scanner mirror position information to the converter during cell-find.

Referring now to the A/D converter 55 in FIG. 3B, the converter has terminals IN, clock and strobe. The A/D converter input is connected to receive the auto-focus integrator output by the analog switch 75B when in the auto-focus mode, and to receive the optical scanner mirror position voltage when in the cell-find mode. An A/D start conversion in initiated at the end of each auto-focus optical scan in the auto-focus mode. It also occurs when a white cell is detected during cell-find.

The optical scanner drive electronics includes both a 1 KHz sine wave generator and a sawtooth generator 83 (FIG. 3c) which sawtooth generator drives the oscillating optical scanner mirror 21' for auto-focus at a repetition rate of about 160 Hz. Specifically, in FIG. 3c, a 19.3 KHz square wave oscillator or clock 80 (FIG. 6, curve a) is connected through a frequency divider 81 to provide a 160 Hz output on conductor 82. This frequency division (FIG. 6, curves b and c) may be done by conventional tandem connected divide-by-11 counters. The 160 Hz output or blanking signal on line 82 is preferably in the form of a positive going pulse (FIG. 6, curve c), having a width of 570 microseconds. The pulse is applied to the input of the sawtooth generator 83. The sawtooth is sent to the input $I_1$ of analog switch 75a by way of an auto-focus optical scan adjust amplifier 84, and when the analog switch is in the auto-focus mode, the sawtooth provides the input to optical scanner drive circuit 85, the output signal of which drives optical scanner 21. The optical scan in one embodiment is about four microns wide and about 150 microns long. An electrical signal representative of the position of scanner 21 is taken from the scanner and fed to a scanner position amplifier 141. The sawtooth wave form, as taken from the input to scanner position amp 141, is shown diagrammatically in FIG. 6, curve f. In one specific embodiment, the scanner 21 is a galvanometer, the sawtooth current from drive circuit 85 flow through the galvanometer coil to oscillate the mirror fastened to the movement. A small resistor in series with the galvanometer coil, and which also receives the drive current, provides a signal on lead 140 to mirror position amp 141.

Figures 4, 6:
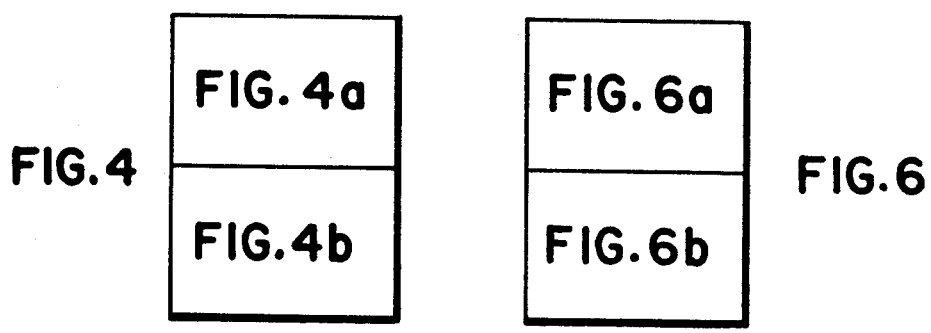
FIG. 4, including
FIG. 6, including

During the fly-back portion of the sawtooth wave form, the auto-focus blanking pulse on line 82 is also inverted 91 and sent to an integrator reset delay one-shot (0/S) 88 which has a 162 microsecond time out. The trailing edge of the pulse output from the delay 88 (FIG. 6, curve d) triggers an integrator reset one-shot 89 (FIG. 6, curve e) which closes the integrator reset analog switch 57 and discharges or resets the integrator 53. Each sweep of the optical scanner provides to the photodiode 25 the optical contrast across the scene. A simulated signal is shown in FIG. 6, curve g. These optical contrasts are amplified, differentiated, rectified and then the electrical pulses are combined in an integrator 53 to provide an analog output of the general type as shown in FIG. 6, curve j.

An additional connection of the output of frequency divider 81 is by conductors 82 and 90 (FIG. 3d) to the upper input of "nand" gate 77. Whenever the inverter latch 72 is enabled and is providing a logic 1 on conductor 74 (the auto-focus mode) to "nand" gate 77, this voltage together with the positive going pulse on line 90 to the "nand+ gate 77 provides a logic zero out on line 91 to one input of an "or" gate 92 and to one input of an "or" gate 93. The output of "or" gate 92 is connected to a D-flop 94. The D-flop 94 also has a clock input from a 1.24 MHz oscillator 95. The D-flop also includes a $\overline{Q}$ output which is connected to trigger a one microsecond start conversion O/S 96 which provides a strobe pulse to the 8-bit A to D converter 55. When the clock 95 goes to logic 1, the logic 1 at the D-flop input results in a logic 1 at the $\overline{Q}$ output to fire the one-shot 96 and strobe the A to D converter.

The output of "or" gate 93 provides an auto-focus blanking signal which is connected to the microprocessor 70 on a conductor 100 and is also connected on conductor 101 to counters A and B clear one-shot 102. The $\overline{Q}$ output (FIG. 6, curve q) of the one-shot 102 is connected by a conductor 103 to the clear input of two bit counter A (read) 104 and a two bit counter B (write) 105. The auto-focus blanking pulse fires the counter clear one-shot 102 which clears the read counter 104 and the write counter 105 at the beginning of each auto-focus optical scan. Each of the counters, 104 and 105, has a pair of outputs $W_B$, $W_A$, $R_B$, and $R_A$ which are connected to the four inputs $B_1$, $B_0$, $A_1$ and $A_0$ of a digital comparator 100, the output of which is connected to a tri-state buffer 107 which provides a cell-find or auto-focus ready signal to the microprocessor 70 on a line 110. The two bit counter B (write) 105 receives an input from an end of conversion one-shot 111 which in turn is triggered by an end of conversion signal carried on a line 112 from the eight bit A/D converter 55. The signal output from the one-shot 111 is also carried on a line 113 to provide an enable input to the 4 × 8 bit register 58. The outputs $W_B$, $W_A$, $R_B$, and $R_A$ of the counters 104 and 105 are also connected to indicate the count to the 4 × 8 bit register 58.

Figure 5:
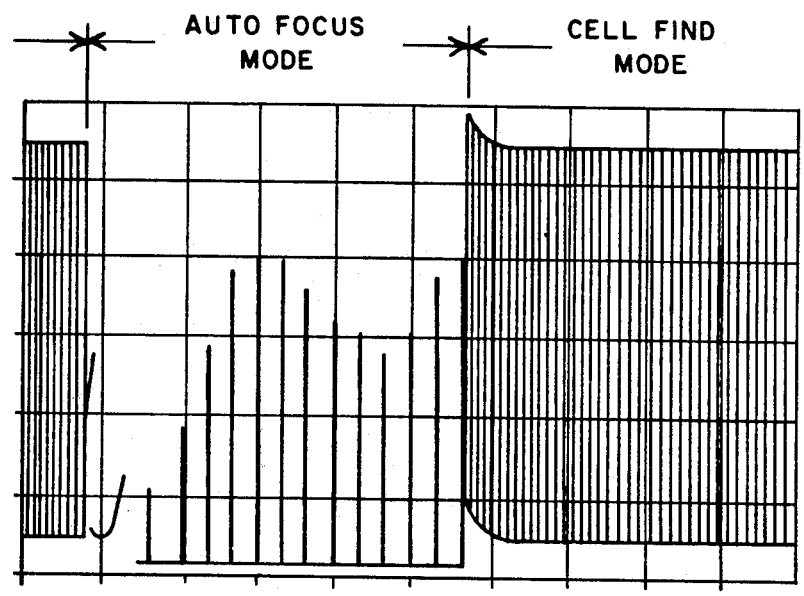
FIG. 5 is a graphical reproduction of an oscilloscope view of the auto focus operation.

In operation, the stage advances continuously in the z direction during successive sweeps of the optical scanner and as focus is approached, the light intensity rate of change become better defined, the differentiated pulses (FIG. 6, curve h) become better defined, the differentiated pulses (FIG. 6, curve h) become sharper and higher and the analog ouput of the integrator 53 increases, as shown graphically in FIG. 5. The advance in the z axis is 0.5μ/ sweep or scan. When the optimum focus is reached, the signals no longer increase and begin to decrease as the focus point is passed. A conventional comparator (not shown) in the microprocessor 70 compares the signal level of each sweep with that of the previous sweep and saves the maximum signal of the plurality of scans. The z address of the maximum level has been recorded in the microprocessor and the z axis position is returned to this address and adjustment stops. The blood cell is then in the optimum focus for viewing either from the TV monitor screen or from the microscope oculars.

The auto-focus timing diagram (FIGS. 6a, b, and c) which illustrates the progression of events during auto-focus, shows in curve a the output of the 19.3 KHz oscillator which is divided by 11 in curve b and again in curve c to therein provide a 160 Hz output, the elevated 570μs portion of which in curve c is called the auto-focus blanking pulse 160. The leading edge of the blanking pulse 160 triggers several events including the integrator reset delay 88 which produces 162μs pulse shown in curve d, it starts the retrace of the sawtooth generator shown as portion 161 of curve f, and it also starts the A/D conversion, curve k. 162μs later in time is the falling edge of the integrator reset delay pulse which triggers integrator reset one-shot 89 to provide a 638 integrator reset pulse 162 shown in curve 3. Curve j shows the integrator 53 output falling to zero and being held at zero until the end of the reset pulse 162. Meanwhile, before the integrator 53 is discharged, the A/D conversion of the voltage level at 163 of curve j is complete, the end-of-conversion EOC pulse being shown in curve 1. The information in the converter 55 is transferred to register 58 when enabled by the pulse, curve n, on line 113. The trailing edge of the EOC pulse triggers or docks the counter B, curve n, which updates the counter B, and provides to the microprocessor 70 on A.F. ready pulse 164, curve o. When the microprocessor can accept the data from the register 58 for storage, an input channel strobe pulse, curve p, read enables the register 58 and buffer 59 to transfer the data into microprocessor storage, the pulse also clocking counter A so that the digital comparator 106 is satisfied.

Next in order of time, the trailing edge of the blanking pulse 160 allows the sawtooth generator 83 to begin a sweep, curve f, thus commencing a new auto-focus sweep. Also, at this time, the A.F. ready pulse, curve o, terminates and the 130ns counters A and B clear pulse occurs. Finally, the integrator reset pulse, curve e, terminates allowing the integrator 53 to operate. A simulated signal output from A.F. preamp 50 is shown in curve g, which, when differentiated by differentiator 51, provides pulses such as curve h, and when full wave rectified appears as curve i to be integrated. The stair-step output of the integrator is shown at curve j. In FIG. 5, the integrator output on succeeding sweeps is shown as adjacent vertical lines increasing in amplitude as optimum focus position is determined and attained.

CELL-FIND

The cell-find operation which has been mentioned briefly above will now be considered further in connection with FIG. 3. Basically stated, during cell-find, the microscope state is caused to move in a predetermined meander pattern to locate leukocytes, and when found, to stop over the leukocyte so that it can be observed. The light source 10 provides a beam through the microscope and a portion of the beam reaches the oscillating optical scanner 21 and is transmitted through the aperture 22 to the photodiode 24 so that the photodiode receives a continuing series of optical sweeps as represented by line 44 of FIG. 2. The output of photodiode 24 is connected to cell-find pre-amplifier 60. An example of the electrical signal output wave form of the amplifier which results from sweep 44 is shown in FIG. 2a and in FIG. 4, curve h. The output of cell-find pre-amp 60 is connected by a line 143 (FIG. 3c) to the input of a negative peak-and-hold detector 144, the output of which is coupled to a cell-find threshold amplifier 145 and then to the negative input of a cell-find detect comparator 146. The line 143 is also directly connected to the positive input of cell-find detect comparator 146. The negative peak-and-hold circuit develops a D/C voltage which is a function of the plasma level when scanning a standard blood slide. The amplifier 145 is adjustable to provide an adjustable cell-find threshold voltage that is some percentage of the plasma level. This threshold level is then compared with the cell-find preamp output at comparator 146 and any signal coming from the cell-find preamp which is less negative then the threshold level (i.e., the signal from a nucleus of white cell) will cause a logic 1 to occur at the output of the comparator.

The level detector 61 which comprises negative peak-and-hold detector 144, threshold adjustable amp 145, and comparator 146 responds to the larger signal level produced by the dark nucleus of the leukocytes (FIG. 4, curve h) to provide a signal output (see FIG. 4, curve i) from comparator 146.

The output signal of the comparator 146 is effective to strobe A/D convertor 55, which convertor also receives, by way of analog switch 75B, an analog input signal which is a function of the optical scanner driving current and thus of the position of the sweep line. Since the optical scanner driving current wave form is generally in the form of a linear ramp which increases (or decreases) with time causing the optical sweep to advance across the field of view, the analog input to the convertor 55, likewise increases, and when the convertor is strobed indicating the presence of a leukocyte in the sweep, the digital output is indicative of the leukocyte address or coordinate along the sweep line. This information is fed to the 4 × 8 bit register 58. This register 58 which is actually four registers has the capacity to handle information on up to three leukocytes in a single scan. This information is subsequently transferred to the microprocessor 70 which stores the location of leukocytes.

Specifically, the leading edge of the logic 1 signal from the comparator 146 triggers cell detect delay O/S 130, the cell detect delay 130 providing a 13.5 microsecond delay (FIG. 4, curve j) which allows the cell detect to occur more near the center of the white cell nucleus, rather than at the cell edge. When the output of one-shot 130 goes to logic 0 it triggers the cell detect lockout one-shot 131, providing a time out of 57 microseconds (FIG. 4, curve k). The $\overline{Q}$ output of 131 is fed back to the input of delay 130, preventing detection of the second of two adjacent cells that are less than 20 microns apart. When the $\overline{Q}$ output of lockout 131 goes to a logic 0, it initiates the cell find A/D conversion (FIG. 4, curve l) by way of "or" gate 92, D-flop and start conversion one-shot 96. Therfore, when either input of "or" gate 92 goes to a logic 0, the output goes to logic 1 and this level connects to the D-flop 94. When the 1.24 MHz clock goes high, the 1 at the D-input results in the D-flop $\overline{Q}$ output going to a high causing the A/D start conversion one-shot 96 to fire and strobe the A/D converter 55. Because of the clock 95, there can be a maximum 18µs delay for conversion start.

At the end of conversion (EOC) at A/D converter 55, the signal on line 112 goes low and fires end of conversion one-shot 111, its $\overline{Q}$ output drops low, the signal on line 113 thereby enabling write register 58, and allows the converter 55 data to be transferred to the A/D converter output register 58. When the $\overline{Q}$ output of one-shot 111 returns to a logic 1 after 1.3 microseconds, it latches the data in register 0, and advances counter 105 to a count of 1. Read counter 104 is at a count of 0 and since 104 count is less than 105, the comparator 106 is satisfied. The CF/AF ready line 110 goes high, telling the microprocessor that data is available. The microprocessor then issues a strobe pulse on conductor 150 which enables read register 58 and tri-state latch or buffer 59 to transfer the data to the microprocessor data bus. When the strobe pulse on line 150 returns high, it advances read counter 104 to a count of 1. When read counter 104 equals write counter 105, the A<B requirement of comparator 106 is not satisfied, and the CF/AF ready signal at line 110 returns to 0 advising the microprocessor that no more data is available.

The oscillating optical scanner 21, 21' is driven at 1000 Hz during cell-find. In one successful embodiment of the present invention a sine wave generator 120 (FIG. 4, curve a) is used to drive the optical scanner during cell-find, a relatively linear portion of the wave being used to generate the sweep.

A sine wave oscillator 120 generates a 1 KHz cell-find optical scan wave form which is amplified to a desired level in a cell-find optical scan adjust amplifier 121, the output of which is connected by a line 122 to the $I_2$ input of the analog switch 75a and thereby to the optical scanner drive circuit 85. The sine wave output is also connected by a line 123 to a zero detect comparator 124 which generates a 1 KHz squarewave (FIG. 4, curve b). The squarewave output of 124 is connected to a 220µs cell-find blanking delay one-shot 125. The falling edge of the squarewave (FIG. 4, curve b) triggers the one-shot 125, the output of which (FIG. 4, curve b) is connected to a 600μs cell-find blanking period one-shot 126. The $\overline{Q}$ output of one-shot 126 (FIG. 4, curve e) is connected by a line 127 to the other input of "or" gate 93 so that the cell-find blanking and the auto-focus blanking are both fed to the "or" gate 93. The blanking signals at the output of "or" gate 93 in addition to being fed to the microprocessor 70 on line 100, are also applied to the input of counters A and B clear one-shot 102. The $\overline{Q}$ output goes low for 130 ns and clears read counter A and write counter B at the beginning of each cell-find optical scan or auto-focus optical scan. The $\overline{Q}$ output of cell-find blanking one-shot 126 on line 127 is connected to the clear input of cell-find detect delay one-shot 130 and this operation insures that no cell is detected during the cell-find retrace.

Referring now briefly to the optical scanner 21, 21' the position of the scanner, is indicated by a current magnitude on a line 140 which inputs to an optical scanner position amplifier 141, the output of which is connected to input $I_4$ of the analog switch 75B. The amplifier 141 provides a phase shift correction between the optical scanner current and the optical scanner mirror position, and provides an adjustable gain allowing the optical scanner position voltage to be adjusted within the dynamic range of the A/D converter 55.

An important feature of the system is that it is possible to record the addresses of a plurality of leukocytes which are encountered on a single scan. If the leukocytes are contiguous or nearly so (that is, less then about 20 microns between leukocytes) the system picks a single address which places all the contiguous leukocytes on the TV screen. When the multiple leukocytes are not contiguous, the individual addresses are stored in the micro computer and are presented sequentially.

Let us assume a cell-find search mode in which three non-contiguous cells are found on a single sweep so that each is detected and the coordinates are all stored in register 58. A count of three has been entered in the counter B105, the digital comparator has provided an output indicating information to be entered in the microprocessor, the cell-find ready signal on line 110 has been issued to the microprocessor 70, the y motor stops, the microprocessor takes the x sweep location data on the first of the three cells from register 48, (counter A104 directing access to the cell No. 1 data), and the process to enter each of the cells on the TV monitor begins. The number of encoder pulses (i.e., the distance), the first cell lies off the meander path is calculated by the microprocessor. If the cell is not already at center position on the TV monitor, the position of the cell relative to the meander path is used to determine the x command; the x motor drives to center the cell on the TV monitor and the slide motion is stopped; the current x and y co-ordinates are displayed; the auto-focus routine is accomplished and the cell is ready for observation and identification. As the identity of the first cell is entered by the observer on the keyboard, normal meander search for the next cell would commence but for the fact that the ready signal on line 110 to the microprocessor is still high indicating the register has information on another cell. The microprocessor issues another pulse on line 150, again enabling register 58, buffer 59, advancing counter A 104 a second time so that the microprocessor can take the data on the second of the three cells. The centering on the second cell proceeds as before. Counter B105 stands with a count of three and counter A104 has now advanced to a count of two. Since the count on A is less than the count on B, the cell-find ready signal remains high indicating yet another cell recorded in register 58. The above procedure repeats to record the location of cell three, center on it and refocus so that the third cell of the scan being described may be identified. Both counters 104 and 105 are now equal in count, the digital comparator recognizes no more unconsidered cells in the register 58 and the ready signal drops. Conventional cell-find now resumes.

The meander search advance for each sweep is about 4 microns. This compares with a typical leukocyte diameter of about 6 microns to about 10 microns, so that a leukocyte is normally recognized before it has passed the center of the field of view of the optics. The z-axis motor which is driving during cell-find is able to stop nearly instantaneously when a leukocyte is found. Since the advancing edge of the leukocyte is normally intercepted and recognized, and since the leukocytes have a relatively uniform size, a fixed y-axis correction from the computer together with an x-axis correction obtained from the leukocyte address in the sweep, adjusts the microscope stage position to bring the leukocyte into the approximate center of the optical axis and the TV monitor. The microprocessor does the calculation to determine how far the white cell is off center in the x direction. If the cell is already roughly at monitor center, no x correction occurs. Otherwise, the position of the cell relative to the meander path is used to determine the x command, the microprocessor then starts the x motor, counts encoder pulses until it gets the required number of encoder pulses and then it stops the x motor. The cell is centered on the TV monitor and the slide is stopped. The current x and y co-ordinates are read and displayed. The microprocessor uses those same numbers to get the system back on the original meander line. Speaking of x position, 1 micron of x position is equal to one A/D level. This provides an x resolution of one micron. The resolution of the encoder presently used is equal to four microns per encoder pulse, providing an effective x resolution of four microns.

Figure 4A:
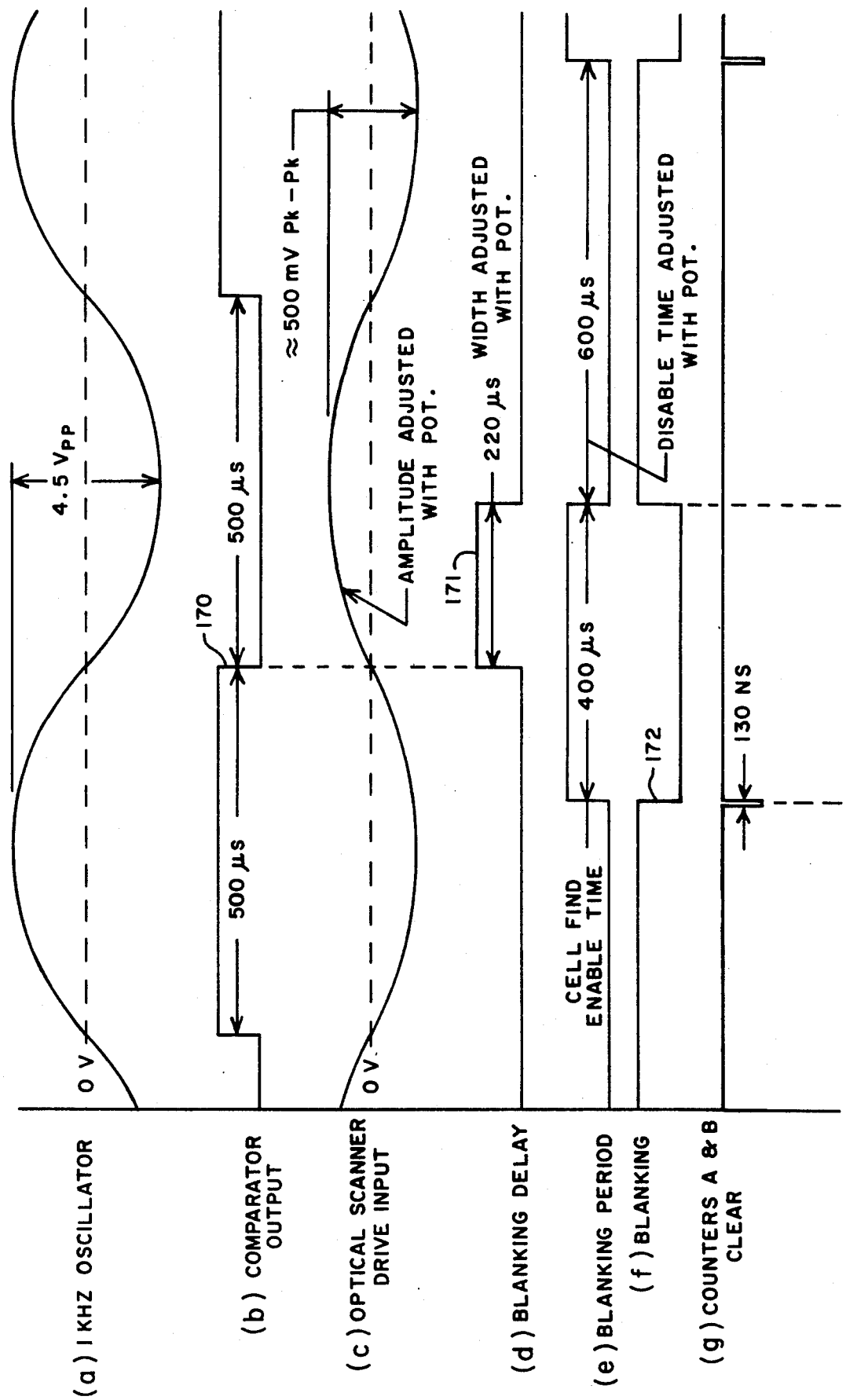
FIGS. 4a and 4b, is a graphical presentation of wave forms as related to the cell-find apparatus of FIG. 3, (i.e., a timing diagram)
Figure 4B:
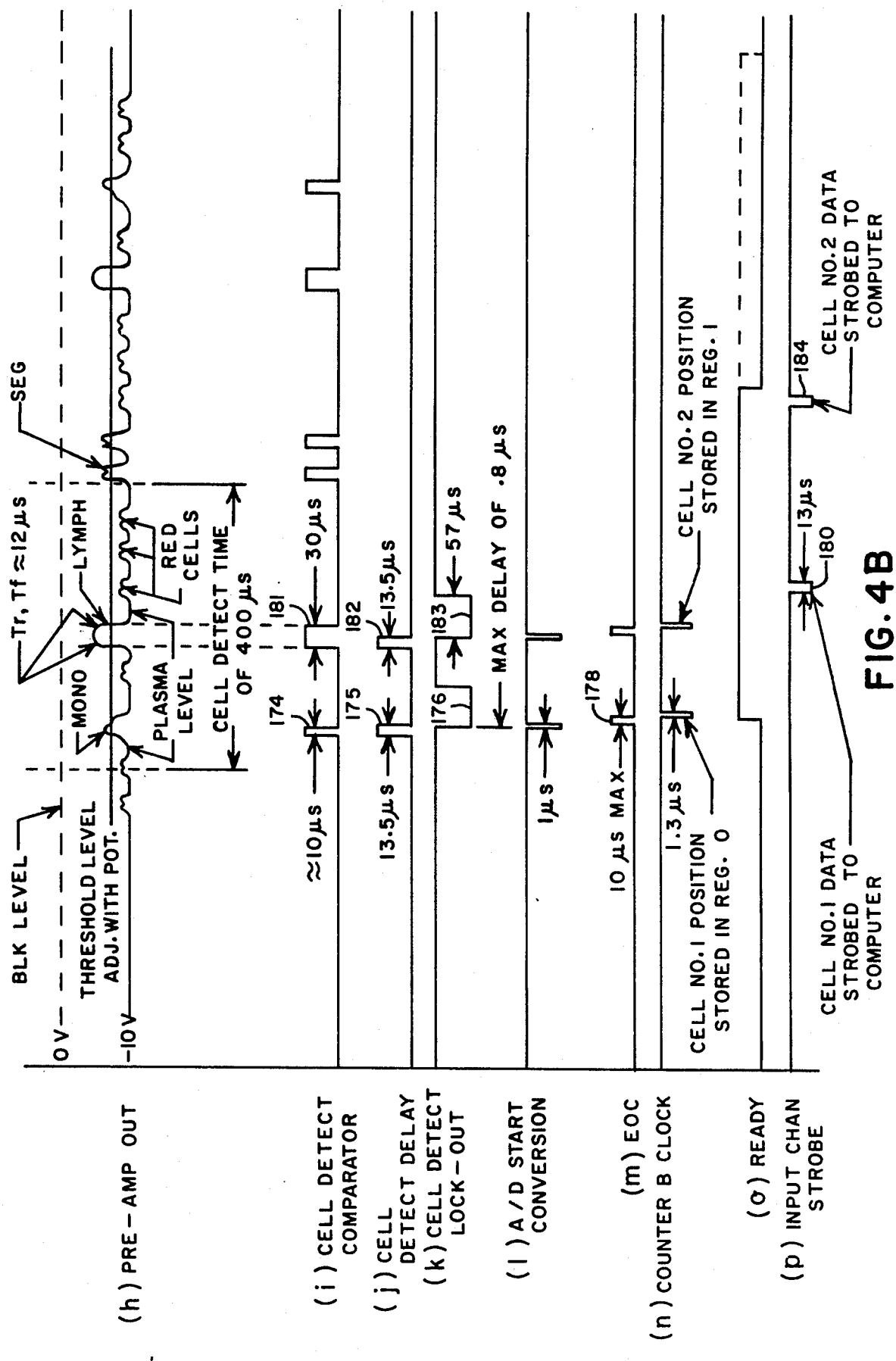
Figure 6C:
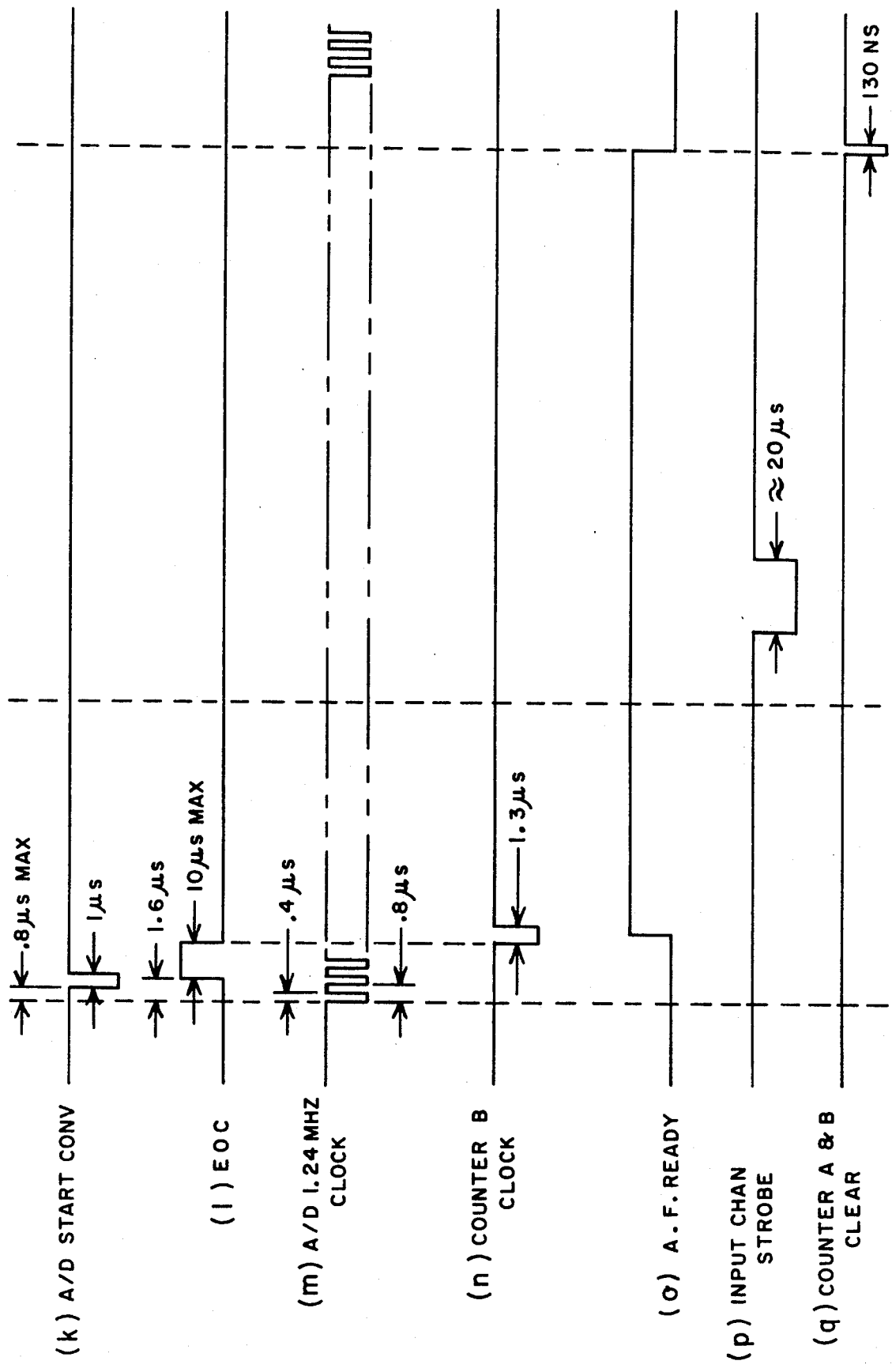

A typical progression through the cell-find timing diagram will now be described. The cell-find timing diagram, FIGS. 4a and b are based on a 1 KHz sine wave, curve a, from osc. 120. This sine wave drives optical scanner 21 by way of amp 121, switch 75a, and drive circuit 85. Comparator 124 detects the zero voltage crossover of the sine wave to provide as output a 1 KHz squarewave shown in curve b. The falling edge 170 of the squarewave triggers 220μs blanking delay one-shot 125 which provides an output pulse 171 as shown in curve d. The blanking delay can be adjusted by a potentiameter in the one-shot multivibrator to get the blanking in proper phase relation with the mirror 21'. At 1000 Hz a 90° phase shift is 225μs. The optical scan sweep is 500μs and 400μs of that is used for cell detect. The trailing edge of the delay pulse 171 triggers C.F. blanking period one-shot 126 which produces a squarewave, curve e, having ≈ 600μs disable time and ≈ 400μs cell-find enable time. The 400μs cell-find enable time is centered about the optical center of the mirror 21' swing. At the leading edge 172 of the enable time, curve f, the 130 ns counters clear one-shot 102 is pulsed, curve g, to reset counts 104 and 105. The cellfind scan which was discussed in connection with FIGS. 2 and 2a presents a light intensity to the photocell which is greatest when only plasma is scanned, which is less when crossing red cells and which intensity is least when intercepting leukocytes. FIG. 4, curve h, shows a curve of voltage level out of C.F. preamp 60 corresponding to light intensity at photocell 24. During the cell detect time of the particular sweep represented by curve h, two leukocytes are indicated and detected. The first to exceed the threshold level provides an output pulse 174, curve i, from the cell detect comparator 146. The pulse width is variable depending on the size of the cell which has been intercepted. The resulting cell detect delay one-shot 130 pulse 175 is shown in curve j, the trailig edge of which triggers cell detect lockout one-shot 131 which produces pulse 176 shown in curve k. This pulse by way of "or" gate 92 and D-flop 94 is effective to trigger start conversion one-shot 96 which provides the 1 $\mu$sec pulse shown in curve 1. The analog electrical signal from mirror position amp 141 which is connected through switch 75B to the input of the converter 55 is converted to digital to indicate the x coordinate of the detected leukocyte. At the end-of-conversion, the EOC pulse 178, shown in curve m, triggers one-shot 111, which updates the counter 105 to a count of one and write enables the register 58 so that the information in converter 55 is transferred to register o in the register 58. The count in counter B is connected by lines $W_B$ and $W_A$ to the register 58 and provides the proper coding into the register to load the information from the converter into the correct one of the 4 registers in register 58. Also at this time, a C.F. ready pulse, curve o, is provided to the microprocessor 70. When the microprocessor can accept the data from the register 58 for storage, and input channel strobe pulse 180, curve p, read enables the register 58 and buffer 59 to transfer the data into microprocessor storage.

Consider again the curve h of FIG. 4, showing the output of preamp 60 during a single scan and it will be seen that a second leukocyte is indicated. Again, the comparator 146 provides a pulse 181, curve i, which results in a delay pulse 182, curve j, a cell detect lockout pulse 183, curve k, followed by the same sequence described above. The 2 bit counter B105 is now advanced to the count of two so that the new information in converter 55 is stored in register 1 in the register 58. Curve p, pulse 184, indicates that the software does not have to accept the information as fast as it is put into the hardware and that, therefore, it may be a number of microseconds later that the microprocessor is ready to accept this data. Two leukocytes have been shown in the sweep, curve h, however, three separated leukocytes in a single sweep can be recorded by register 58 and transferred to the microprocessor. When there are two leukocytes close together in a sweep, the cell-find lockout 131 prevents the recording of the second cell coordinates, however, the operator sees both cells on the monitor when looking at the first cell that was detected. Immediatly after the cell number two data is strobed to the computer, the computer updates the counter A so that it is same as counter B and then the digital comparator is satisfied which causes a cell-find ready signal to go low indicating only two cells were detected on that sweep.

KEYBOARD

Figure 14:
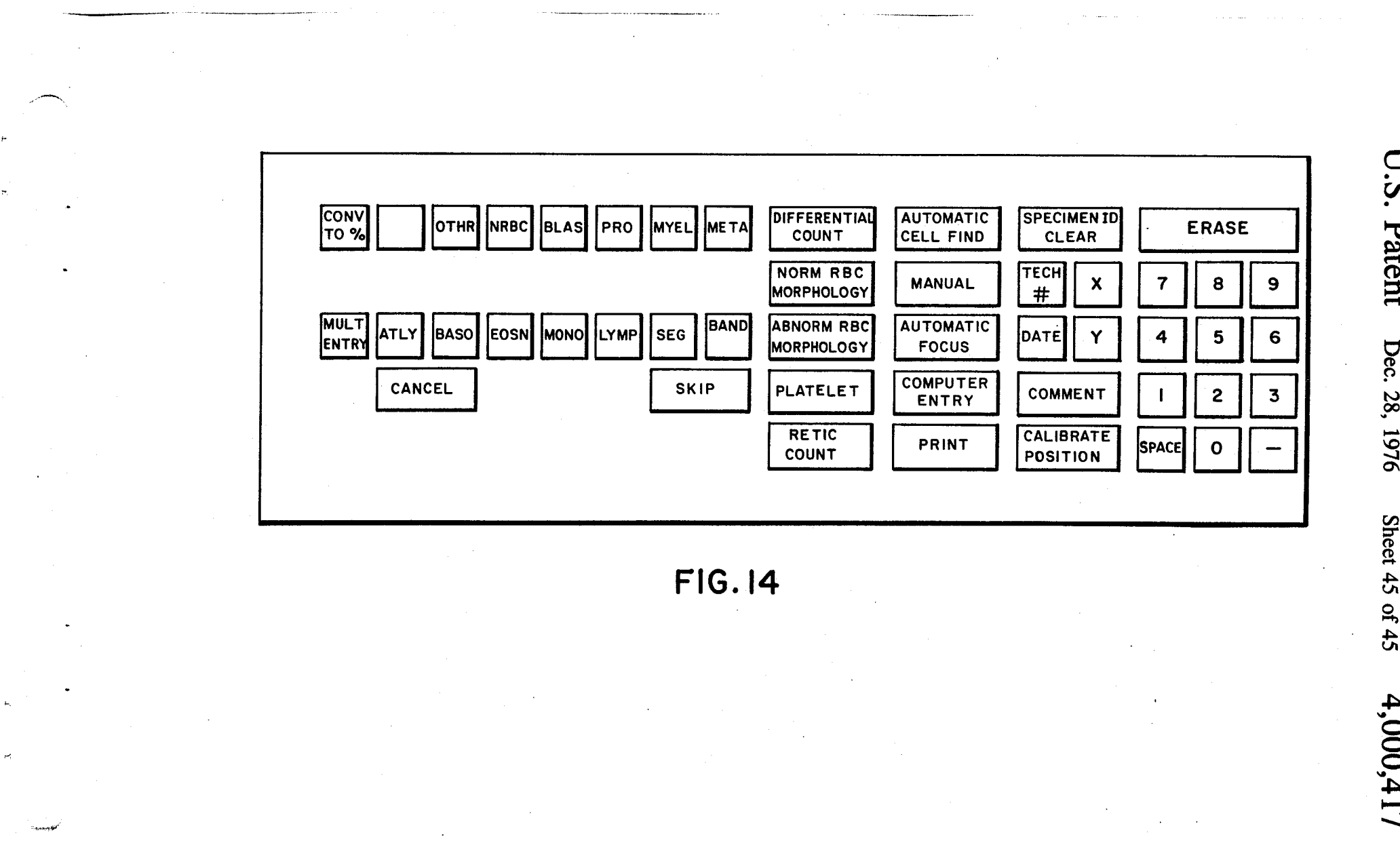

The keyboard 30 as detailed in FIG. 14 includes a numeric keyboard which is used to enter various numeric codes, platelet sufficiency code, abnormal RBC morphology severity codes and X–Y stage position coordindates. To the left of the numeric portion of the keyboard, the next set of keys includes Specimen ID Clear used to clear old data before data entry on a new slide; X to enable entry of a three-digit X-coordinate code through the numeric keyboard which causes stage to move to that coordinate; Y, same as X for the Y-coordinate; Tech No. to enable entry of an operator identification code through numeric keyboard; Date, to enable entry of date code through numeric keyboard; Comment, to enable entry of a three-digit comment code through numeric keyboard; and Calibrate to enable calibration of X–Y coordinates.

The next set of keys includes Automatic Cell-Find key which places the instrument in automatic mode and immediately below a Manual key which places the instrument in a manual mode for cell-find; Automatic Focus key which selects automatic focus when in manual mode; Computer Entry key to enter stored data into a computer; and, Print key to print stored data on a ticket.

The next set of keys includes a Differential Count key to enable entry of leukocyte differential count through cell counting keys; a Norm RBC Morphology key to enter normal red blood cell morphology comment; Abnorm RBC Morphology key to enable entry of abnormal RBC morphology comments through cell counting keys and severity comments through numeric keyboard; Platelet key to enable entry of platelet sufficiency through the numeric keyboard; and, Retic Count key to enable entry of reticulocyte count through cell counting keys.

The Cell-Counting keys are used to count leukocytes in differential count, red blood cells in abnormal RBC morphology studies, and reticulocytes in reticulocyte count. The Skip key allows for moving the stage off a cell without counting the cell. The Convert to % key enables conversion of display panel information from number of cells counted to percent of total cells counted; the Mult Entry key causes the stage to remain stationary over the last cell so that more than one cell can be counted.

MICROPROCESSOR

Figure 7A:
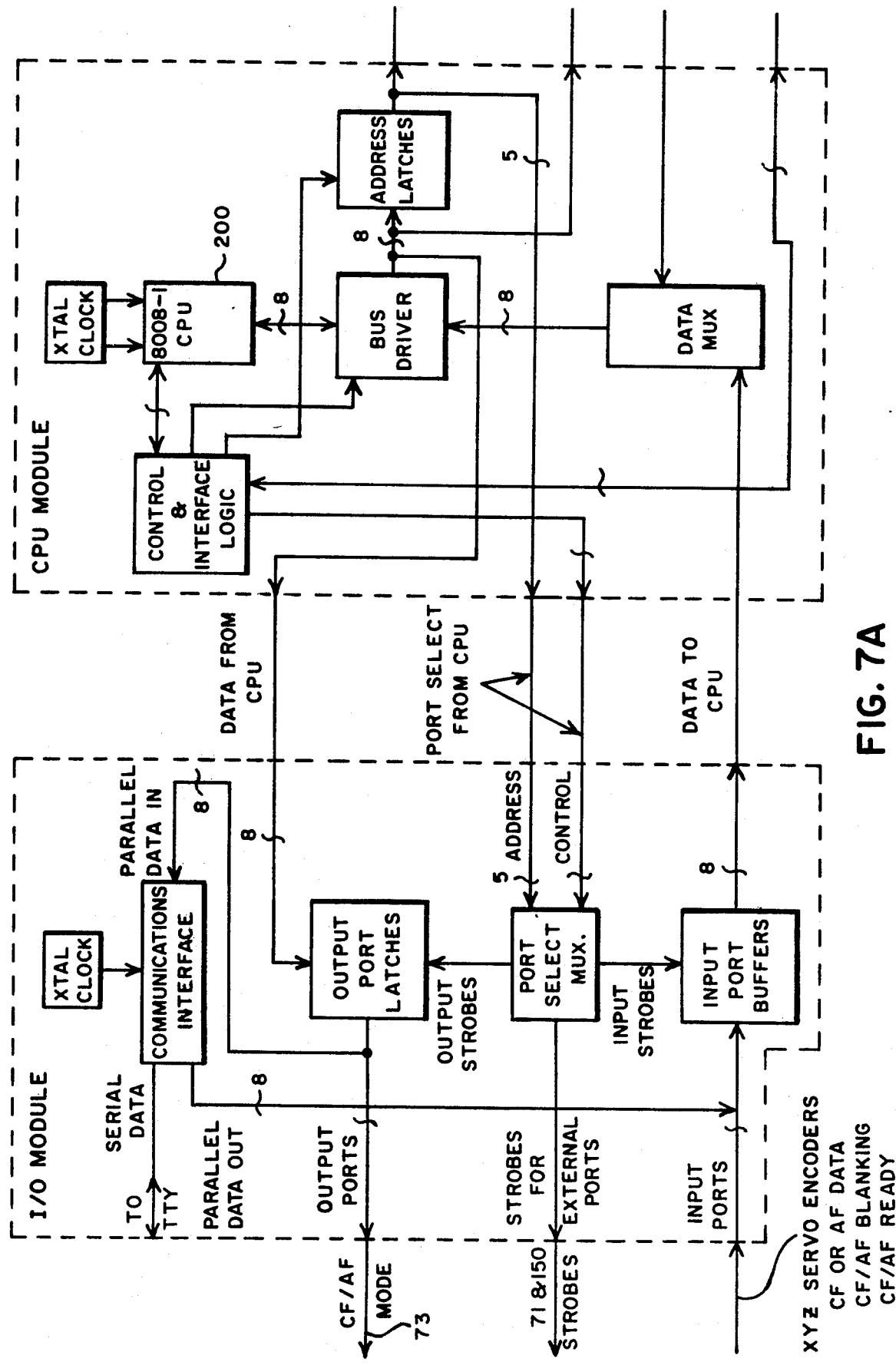

The microprocessor shown as a block in FIGS. 1 and 3 has been referred to a number of times heretofor. Pertinent portions of the microprocessor 70 are shown in a more detailed block diagram form in FIGS. 7A and 7B. The heart of the microprocessor shown in FIG. 7A is a conventional Central Processor Unit (CPU) 200 which is a Model Intel 8008-1, sold by Intel Corporation. The 8008-1 is a single chip MOS 8-bit parallel CPU. This 8008-1 is described in the Intel Corp. literature such as "Intel MSC-8 User's Manual," Nov., 1974). The four basic function blocks of the 8008-1 processor are an instruction register, memory, arithmetic-logic unit and I/O buffers. It includes six 8-bit data registers, an 8-bit accumulator, two 8-bit temporary registers, four flag bits, and an 8-bit parallel binary arithmetic unit which implements addition, substraction, and logical operations. A memory stack containing a 14-bit program counter and seven 14-bit words is used internally to store program and subroutine addresses. The 14-bit address permits the direct addressing of 16K words of memory. More detailed explanation of and instructions for the 8008-1 may be found in the manual listed above. The program of the system is stored in a conventional memory array 201. The remainder of the blocks in FIGS. 7A and 7B may be considered as conventional peripherals to the 8008-1 CPU 200.

PROGRAM

The tables A, B, C, D, and E below detail the program used for cell recall routine, differential count routine, cell-find routine, return to meander line routine, and automatic focus routine. Complementing the program are flow diagrams shown in FIGS. 8 through 12. PL/M program language is used.

Figure 8D:
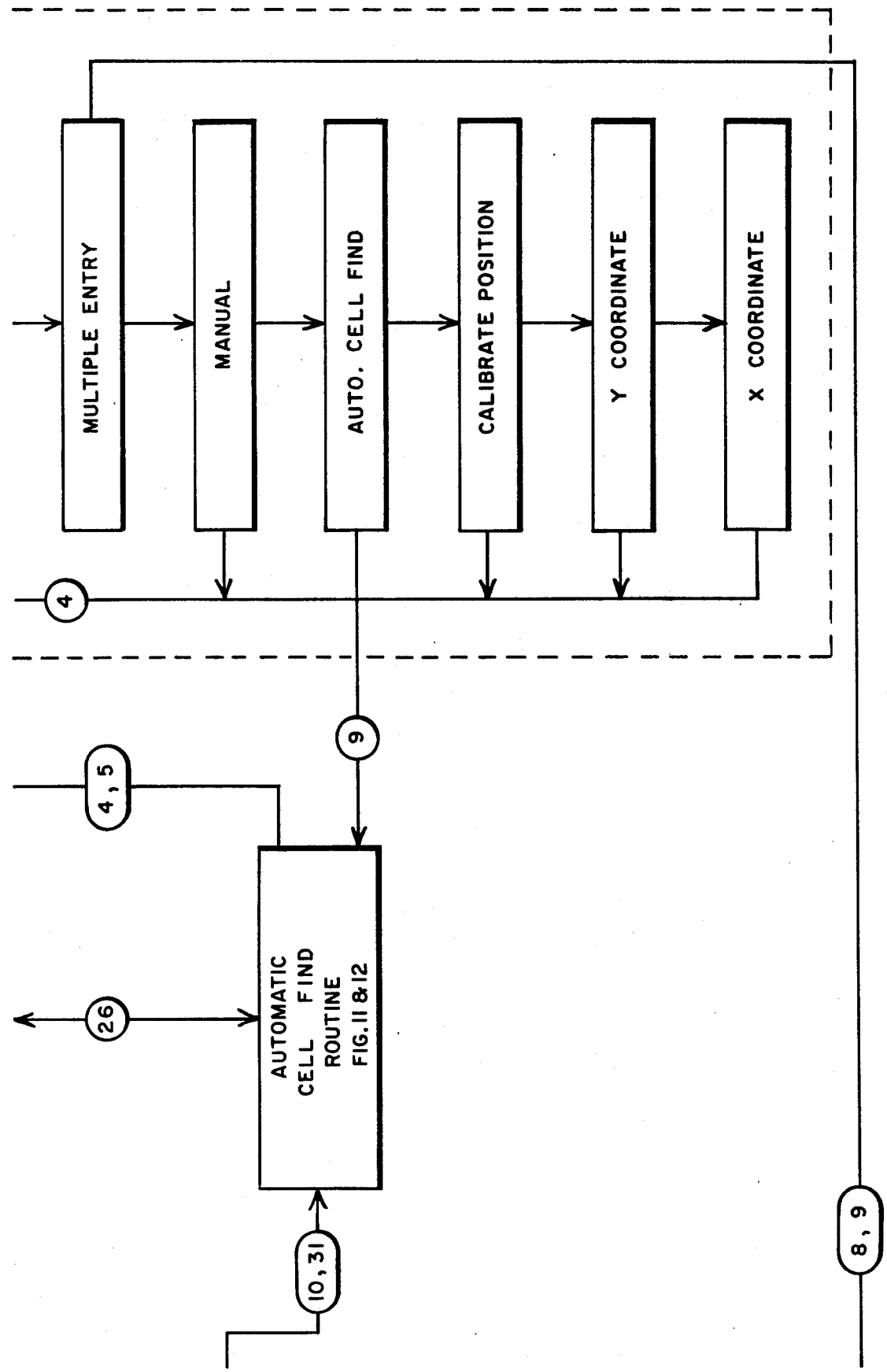
Figure 9A:
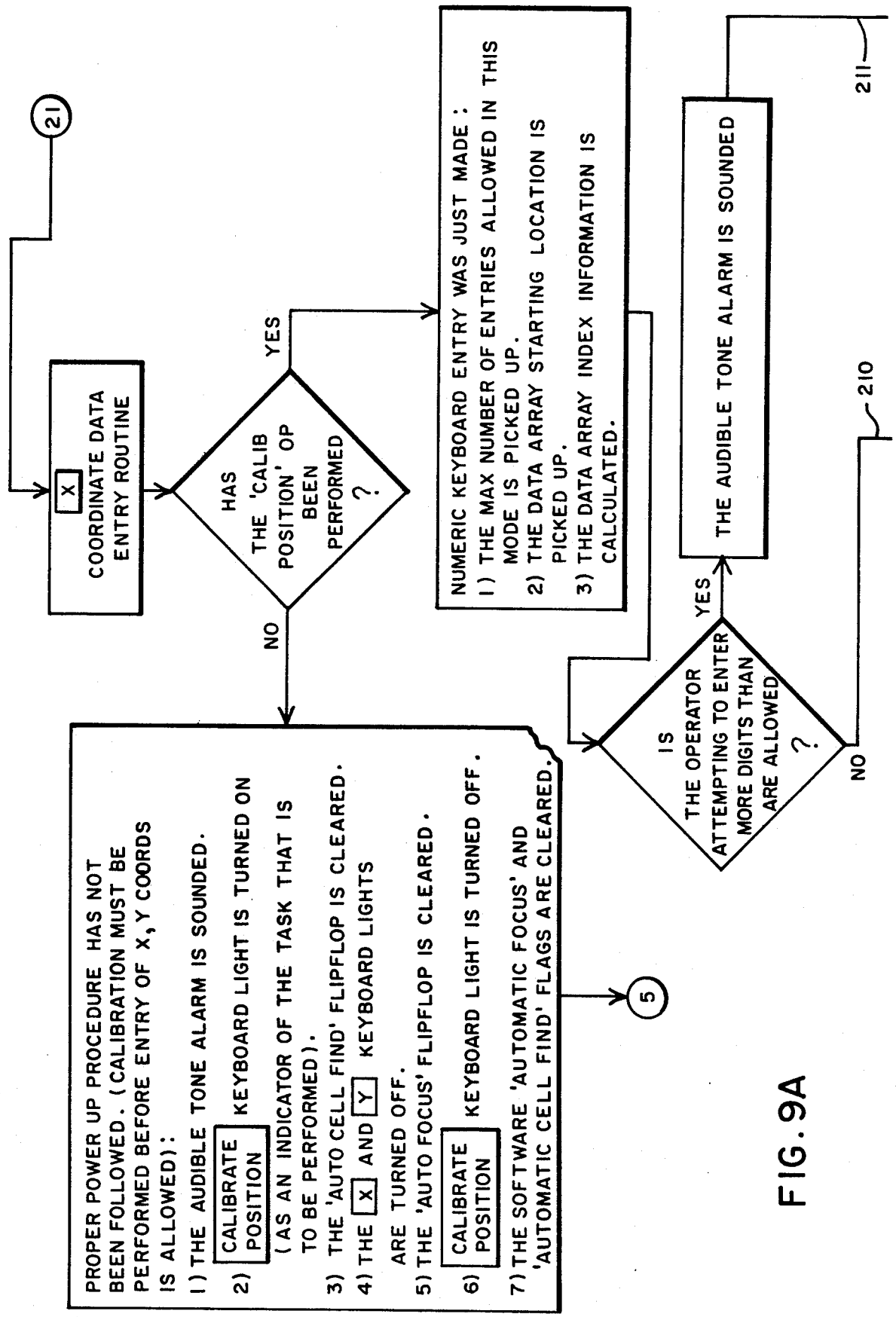
Figure 9B:
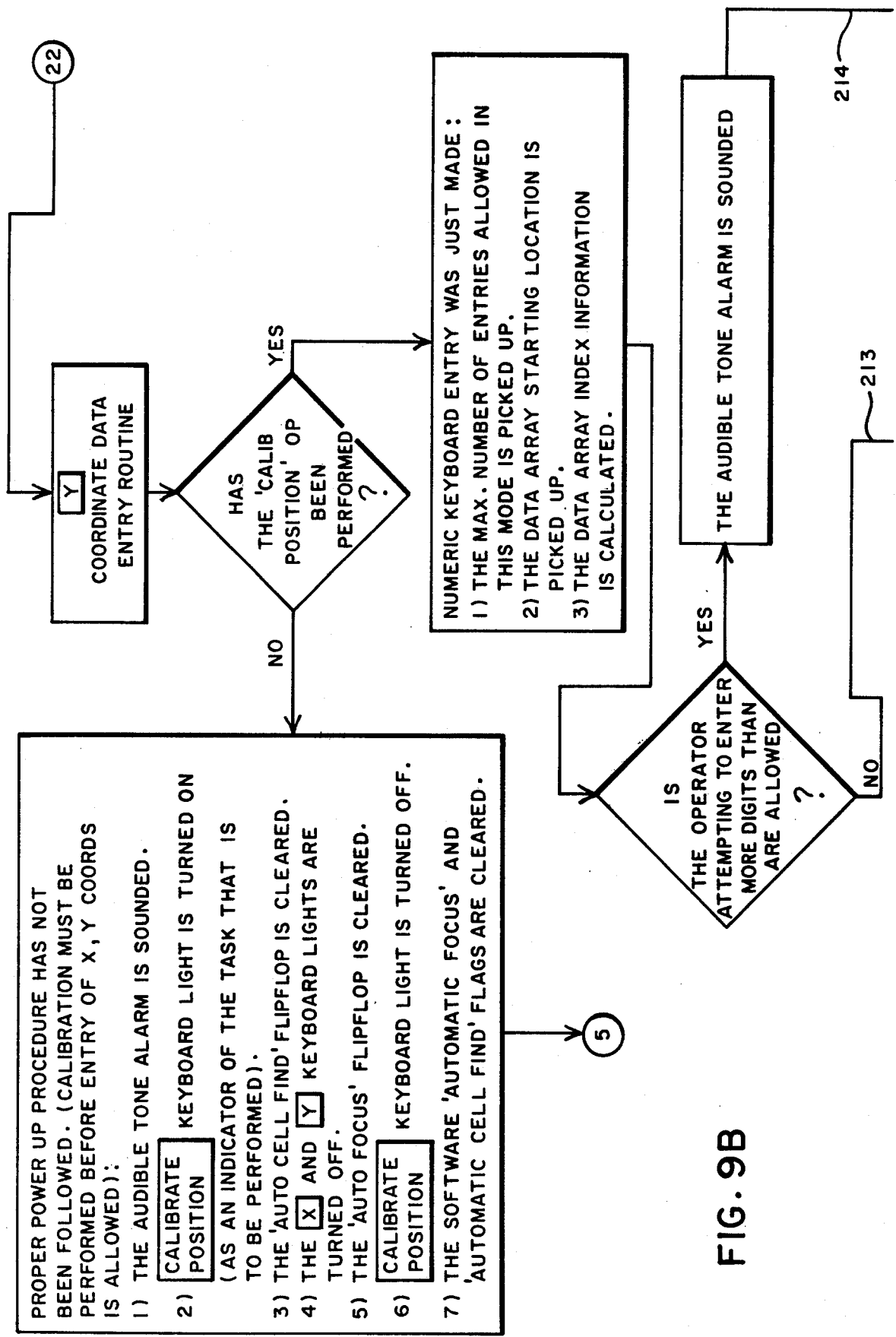
Figure 9C:
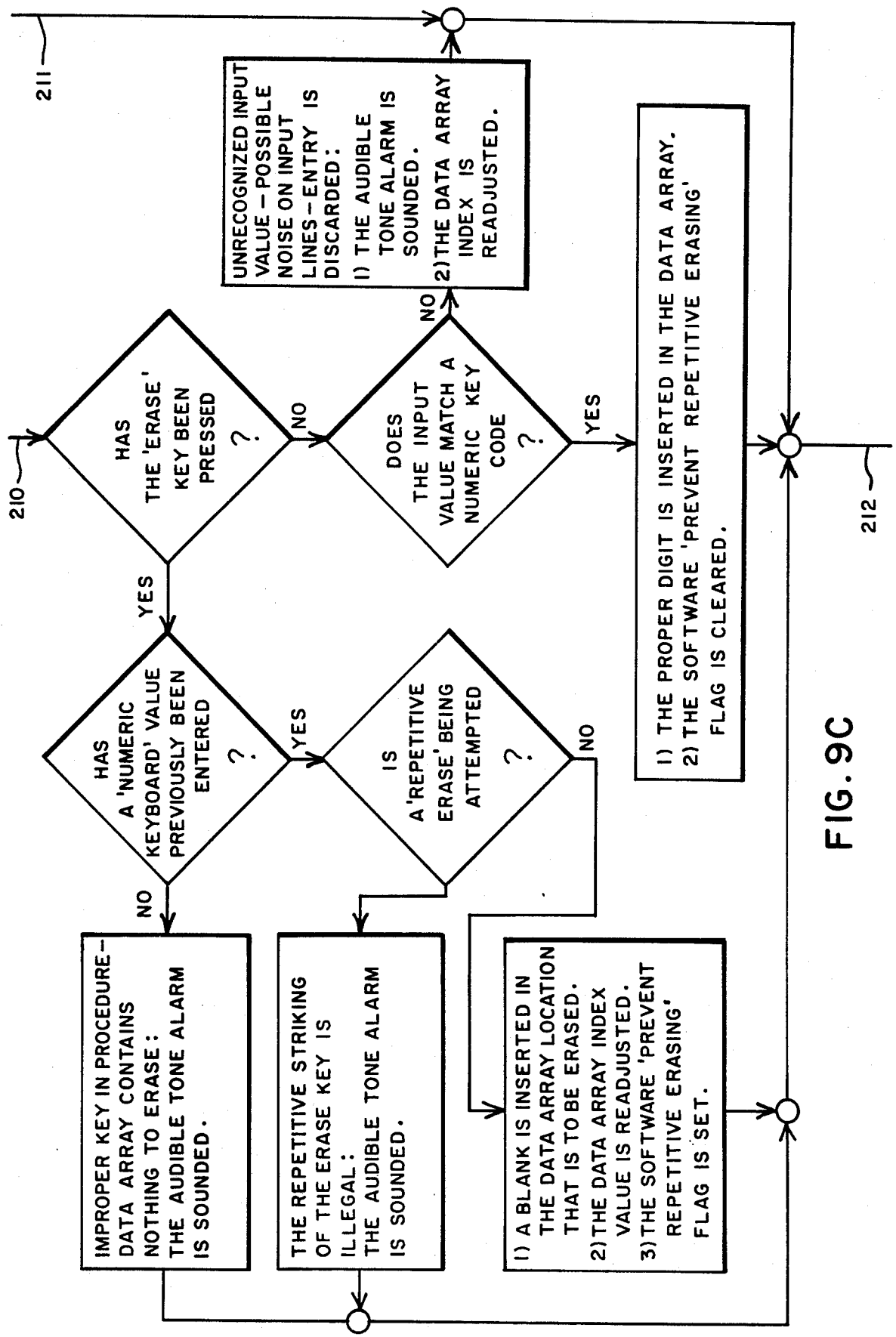
Figure 9D:
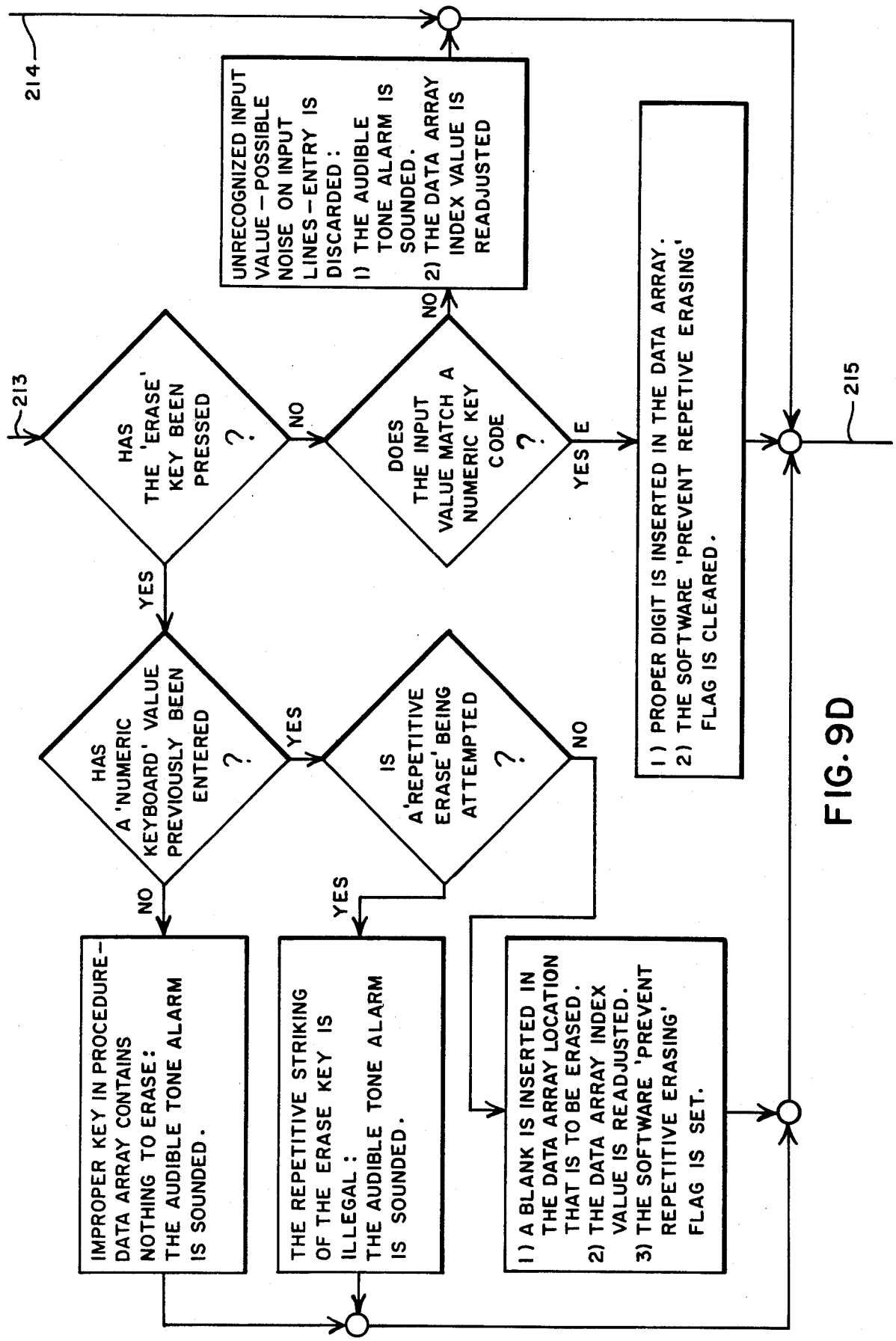
Figure 9E:
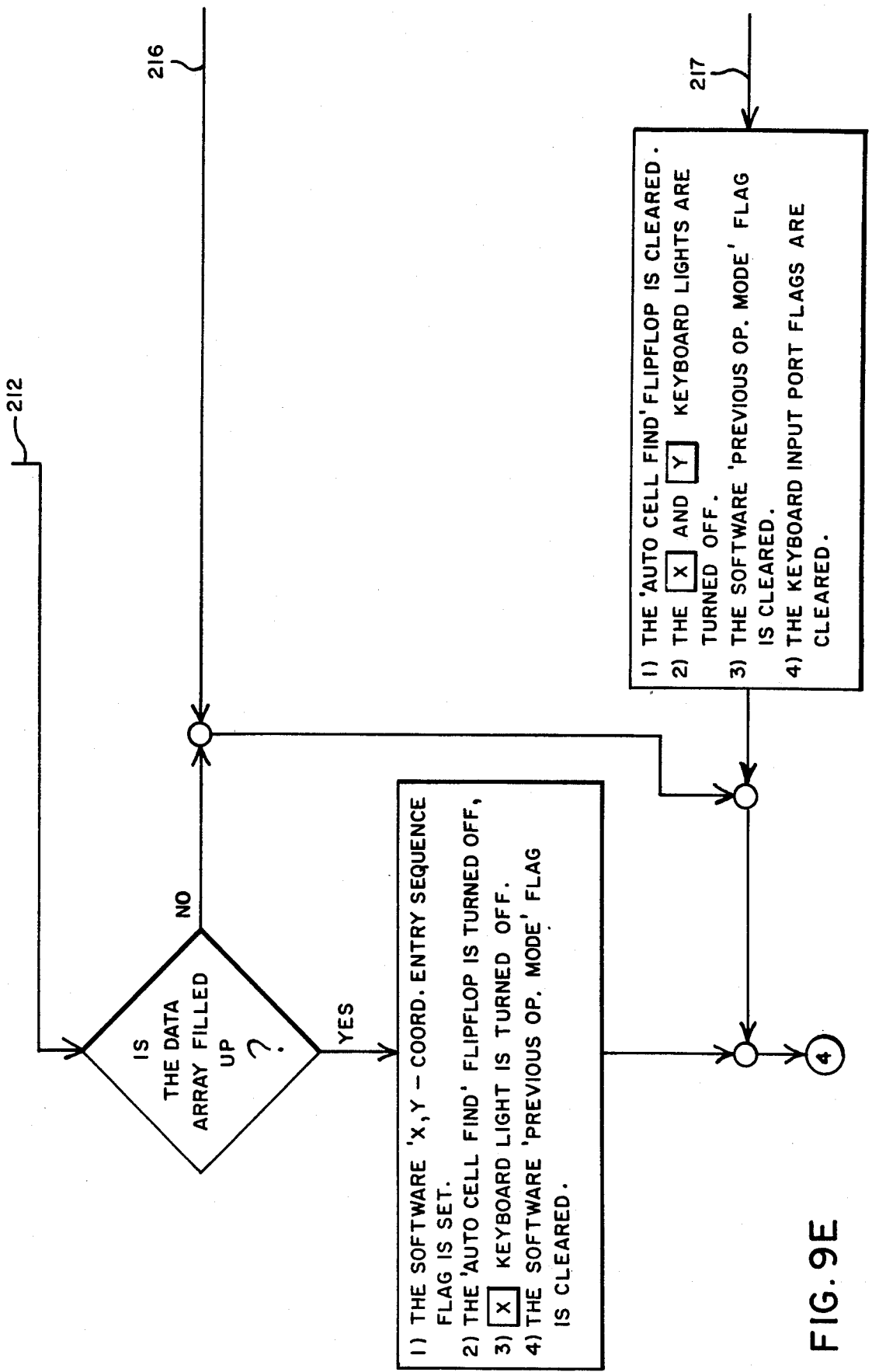
Figure 10A:
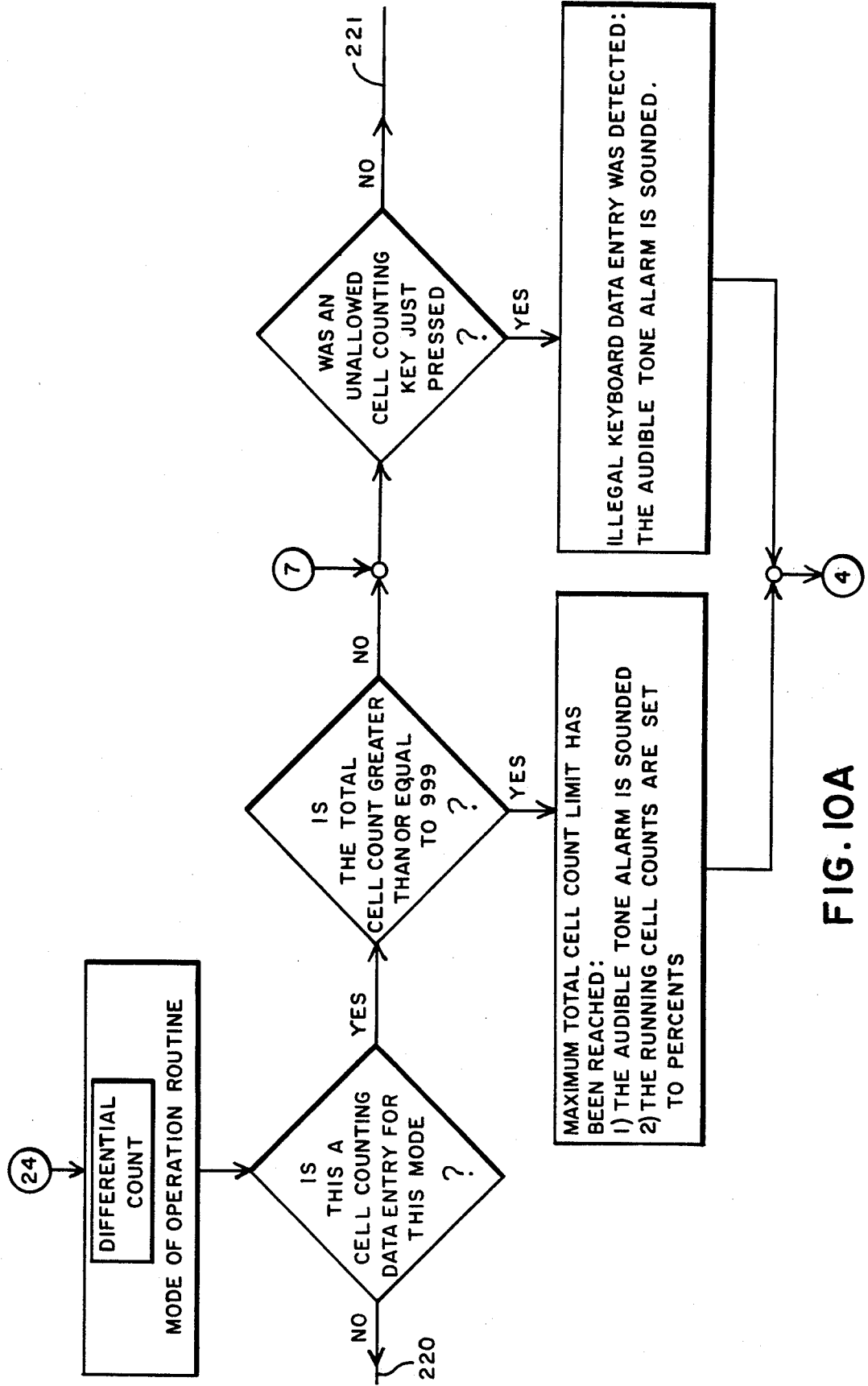
FIGS. 10a, 10b, 10c, 10d, 10e, and 10f, is a flow diagram of keyboard 1: differential count routine.
Figure 10B:
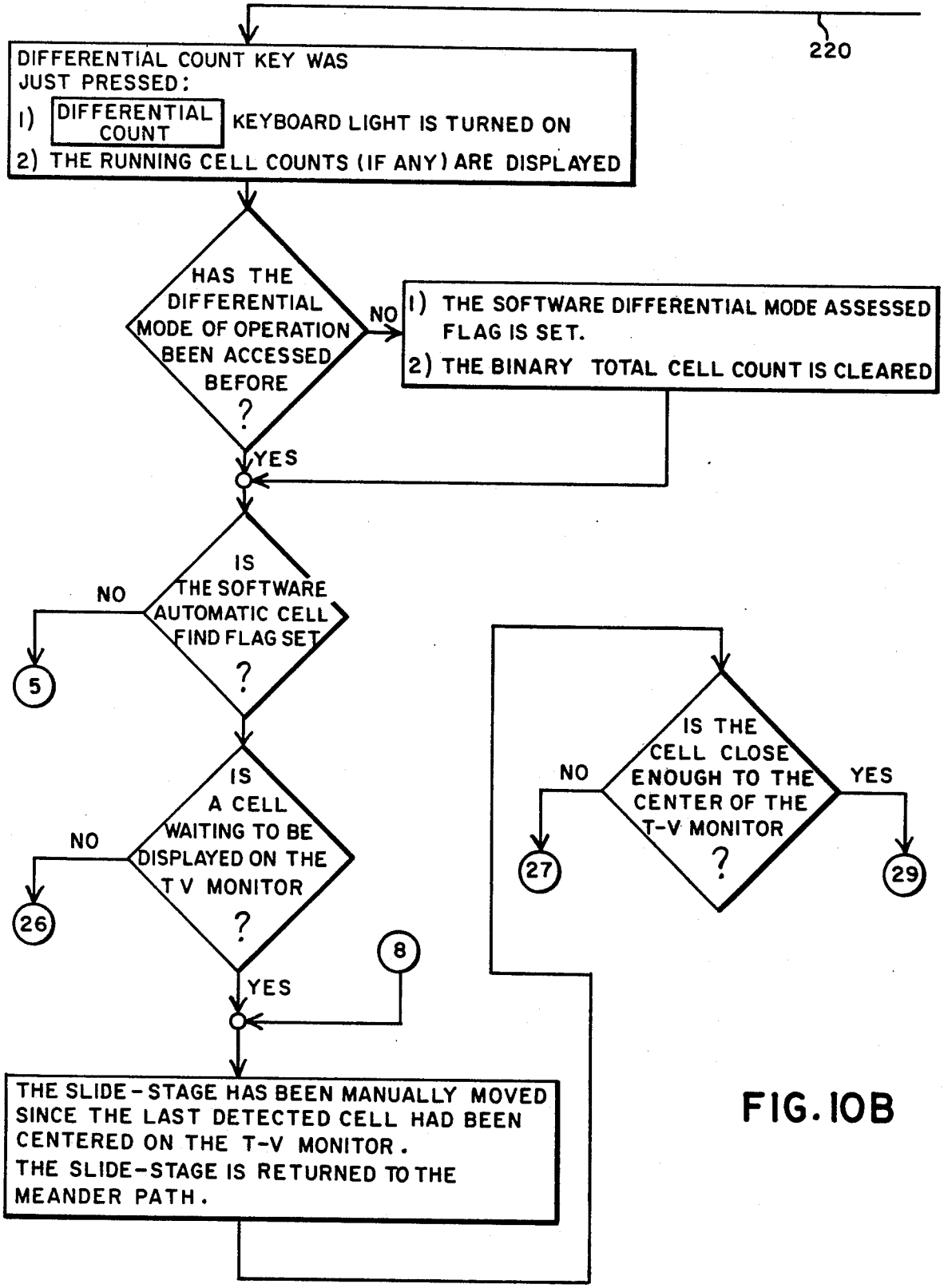
Figure 10C:
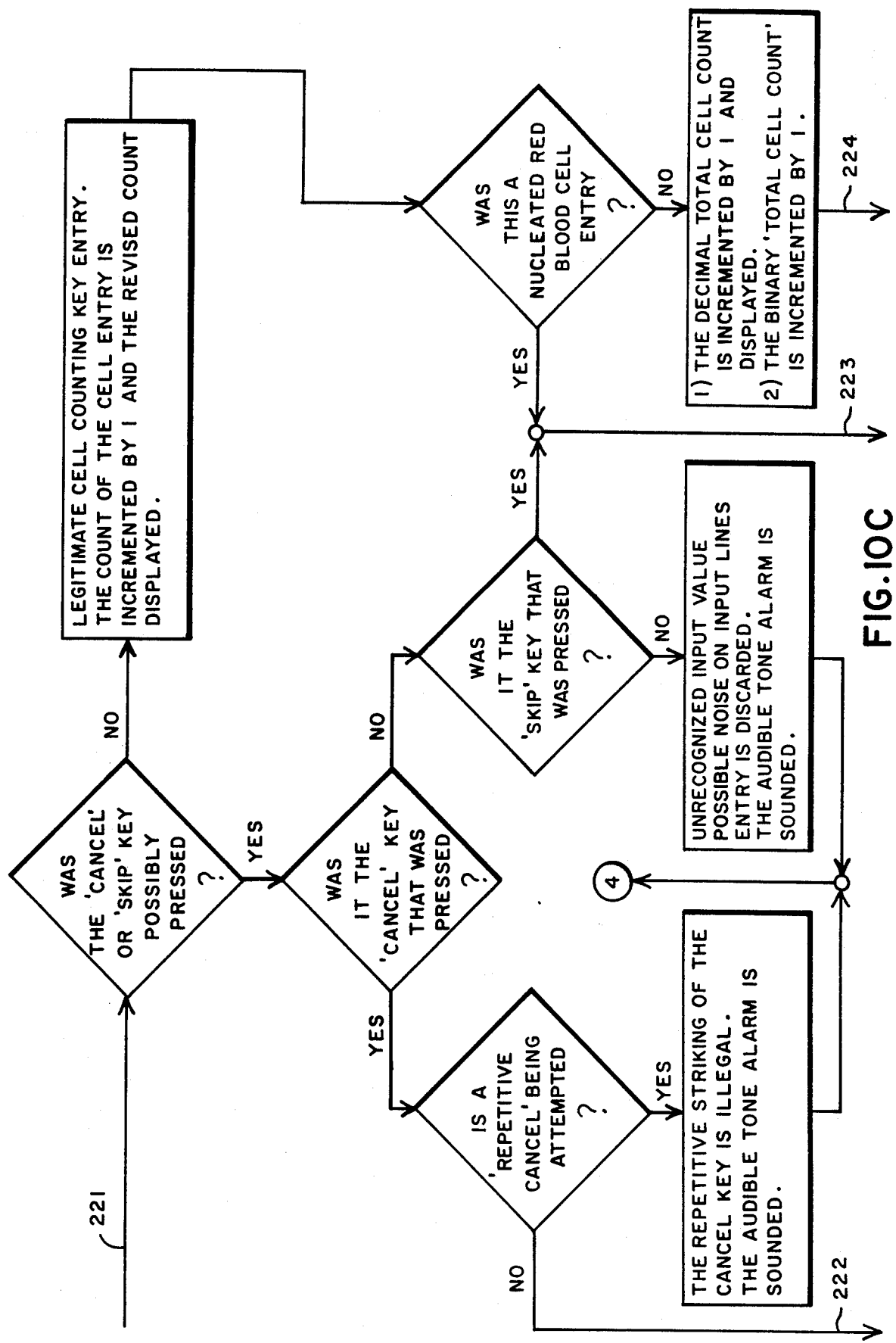
Figure 10D:
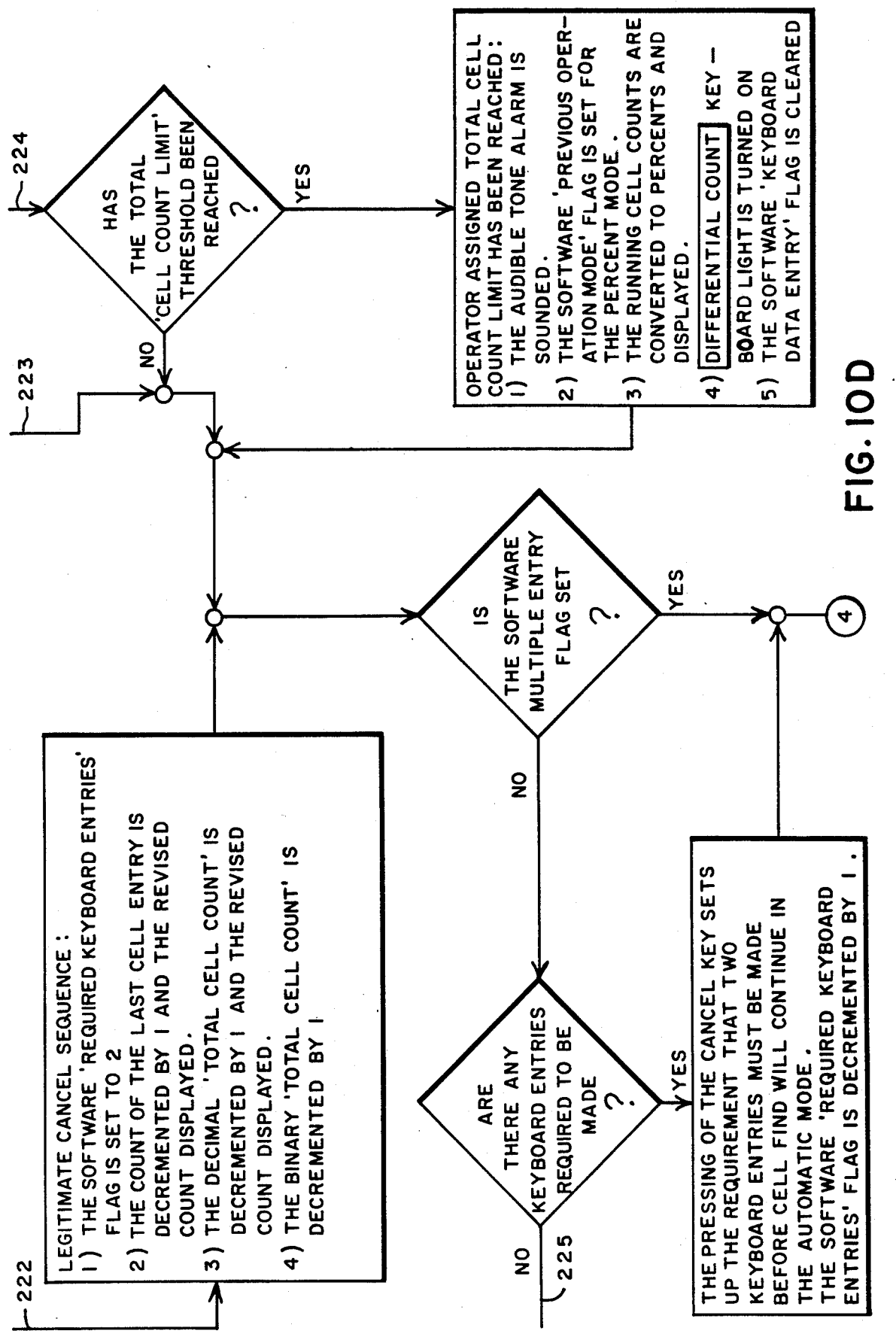
Figure 10E:
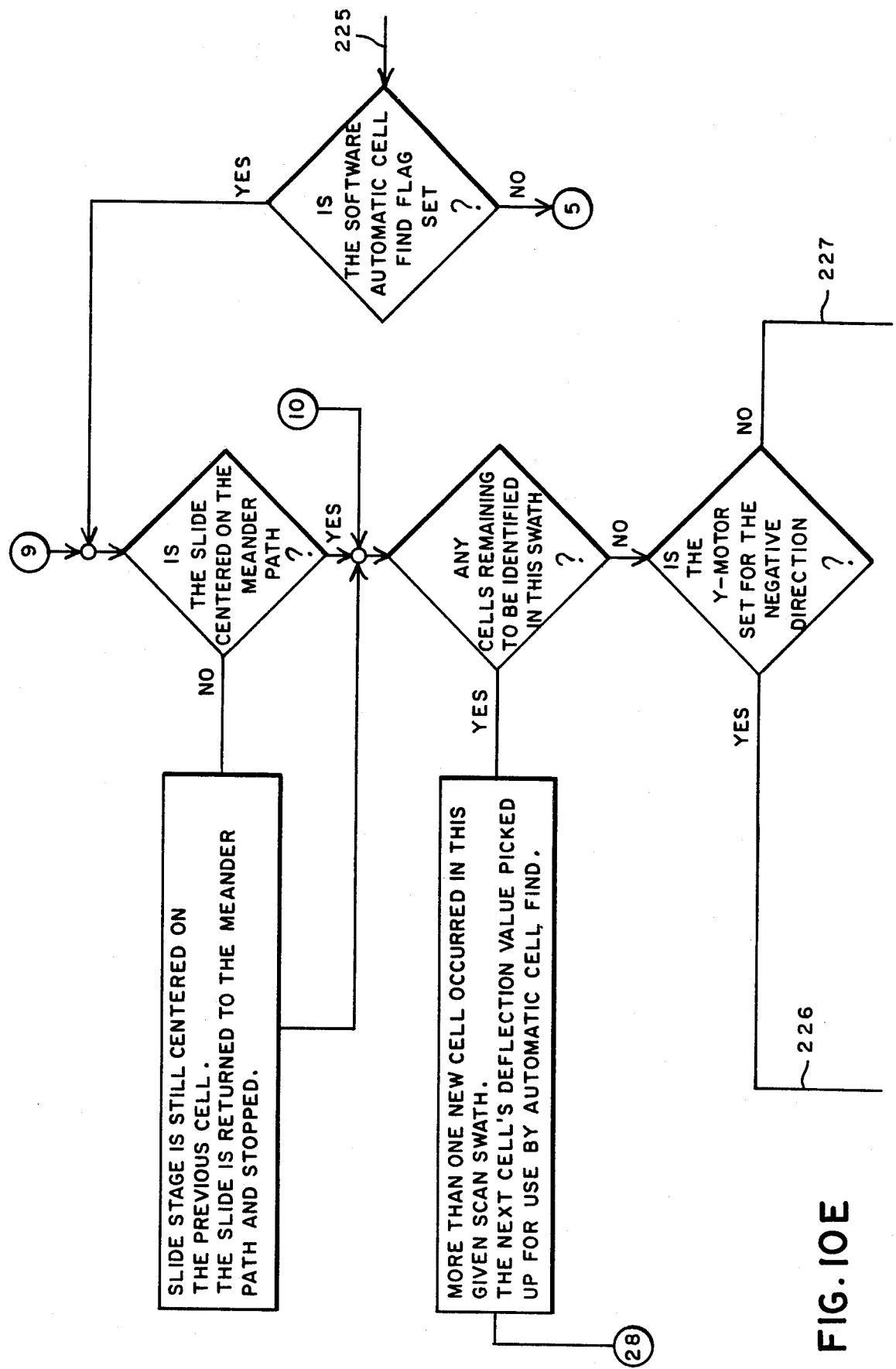
Figure 10F:
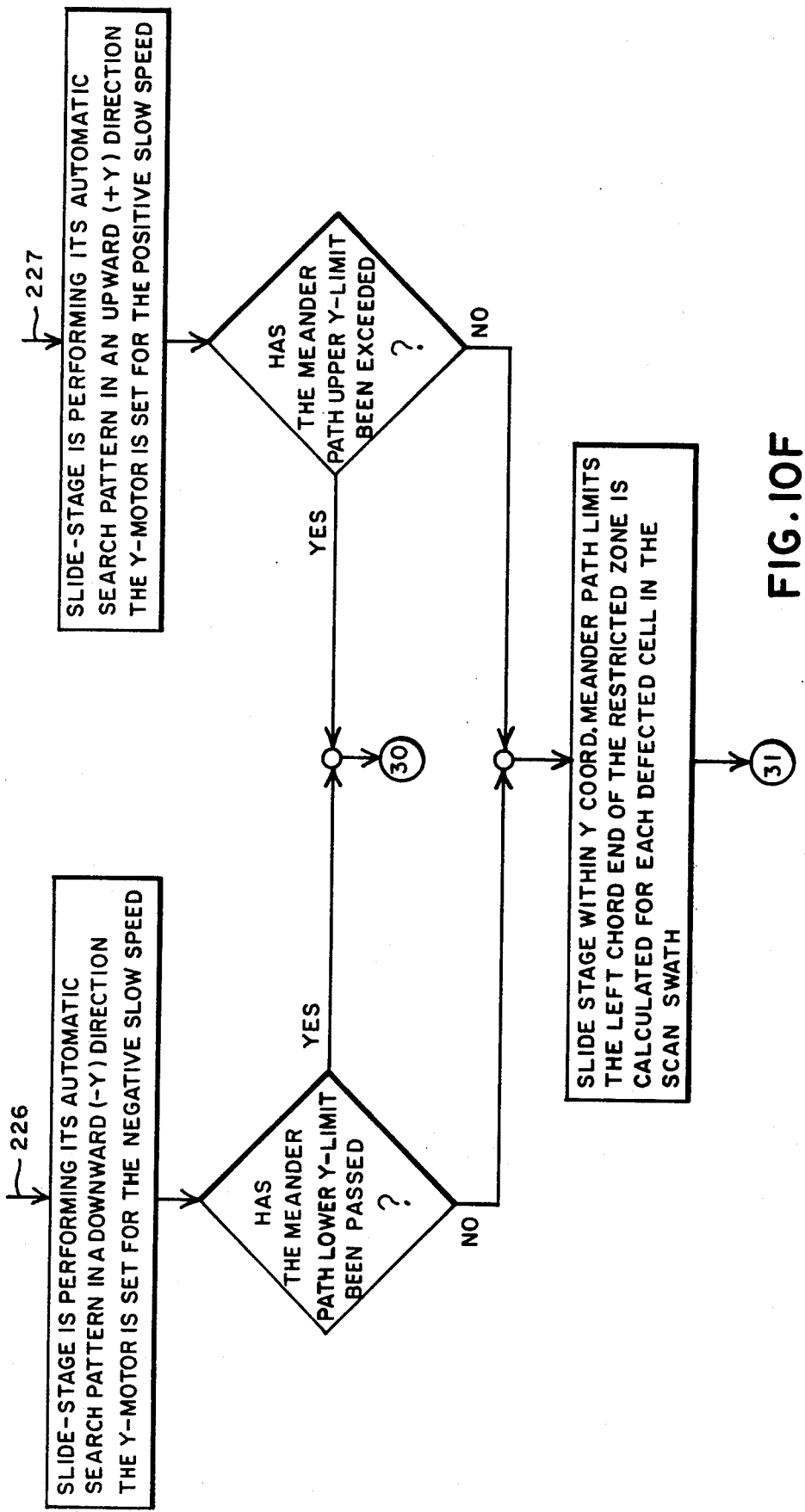
Figure 11A:
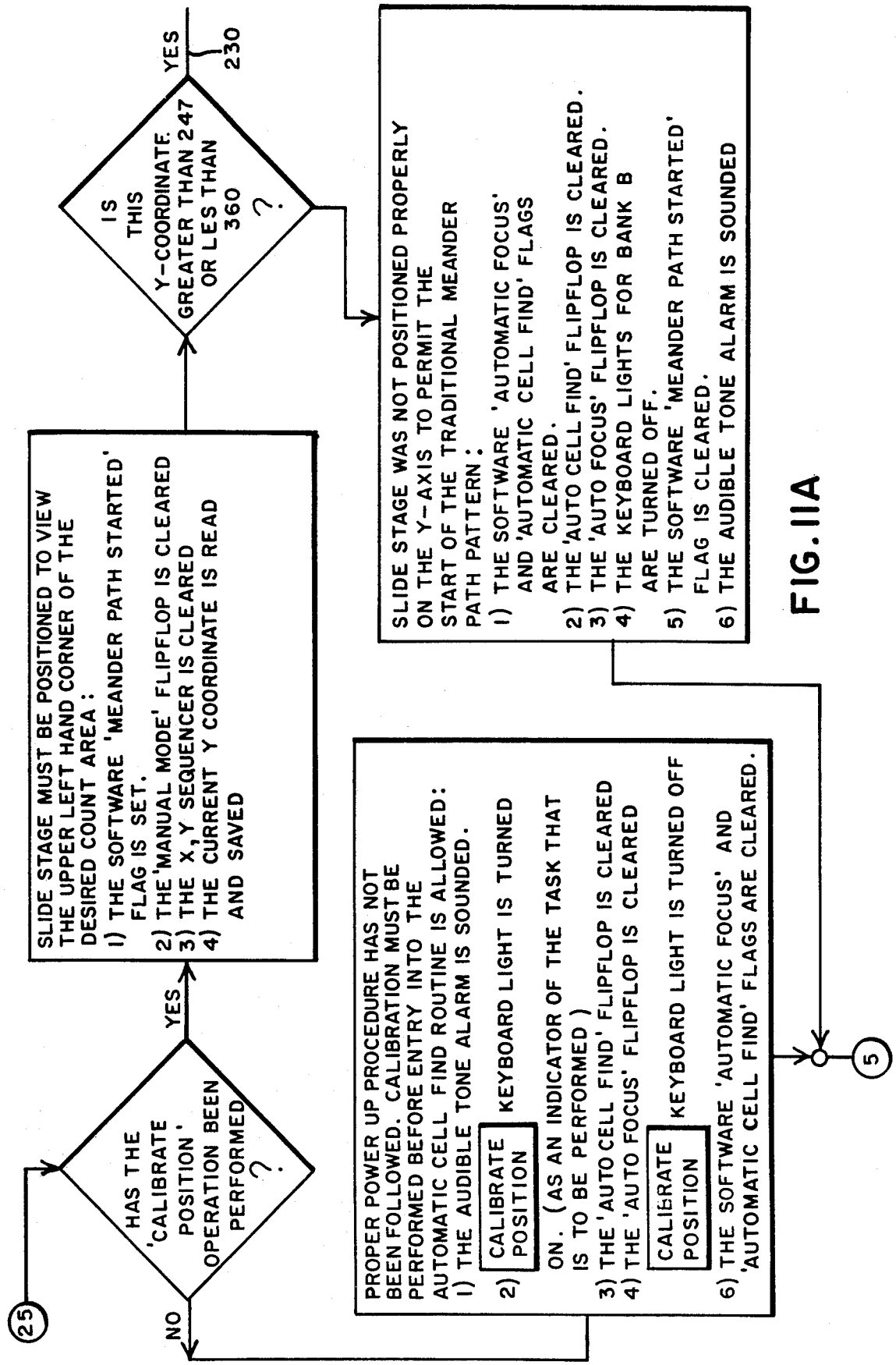
Figure 11B:
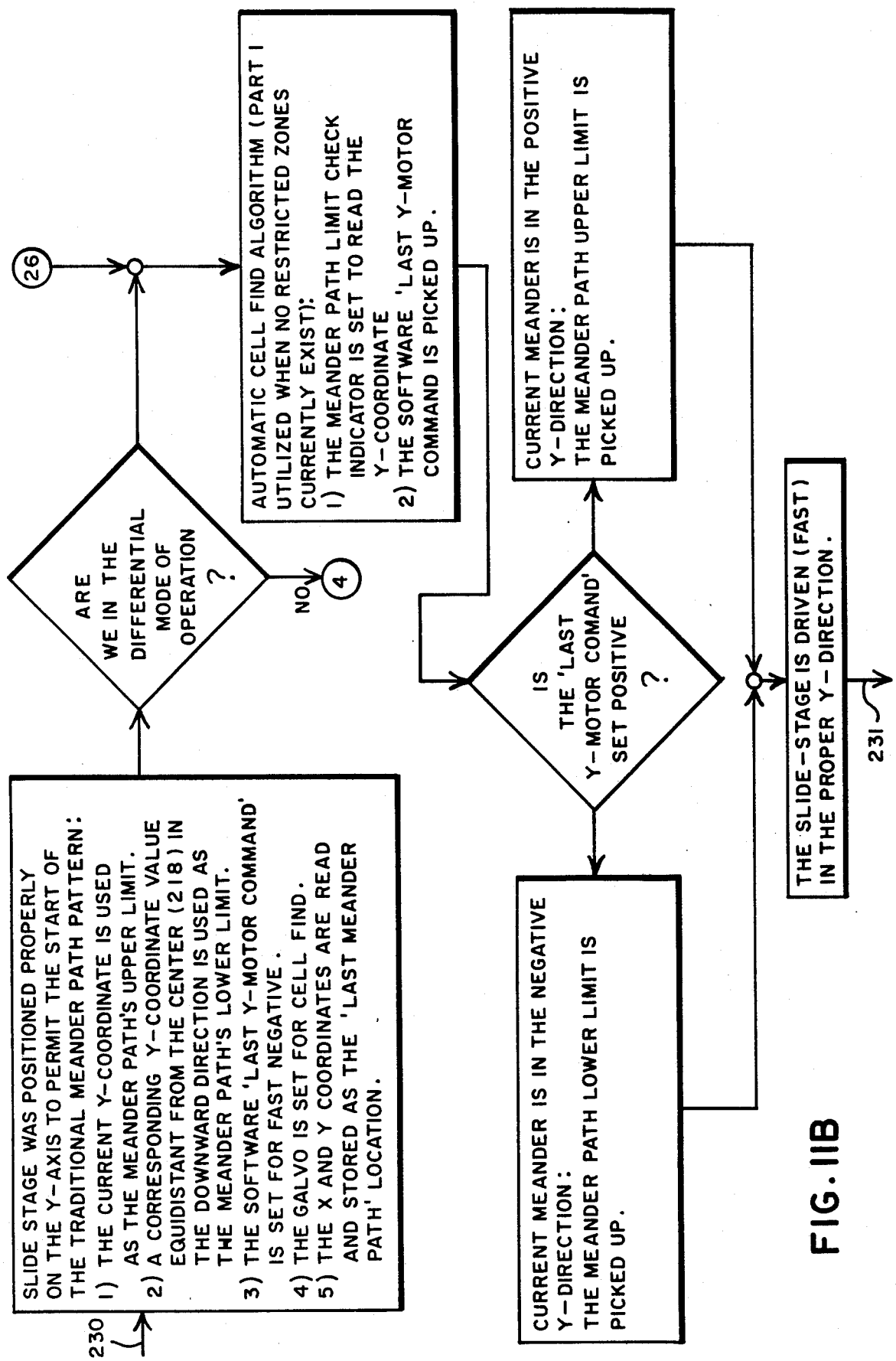
Figure 11C:
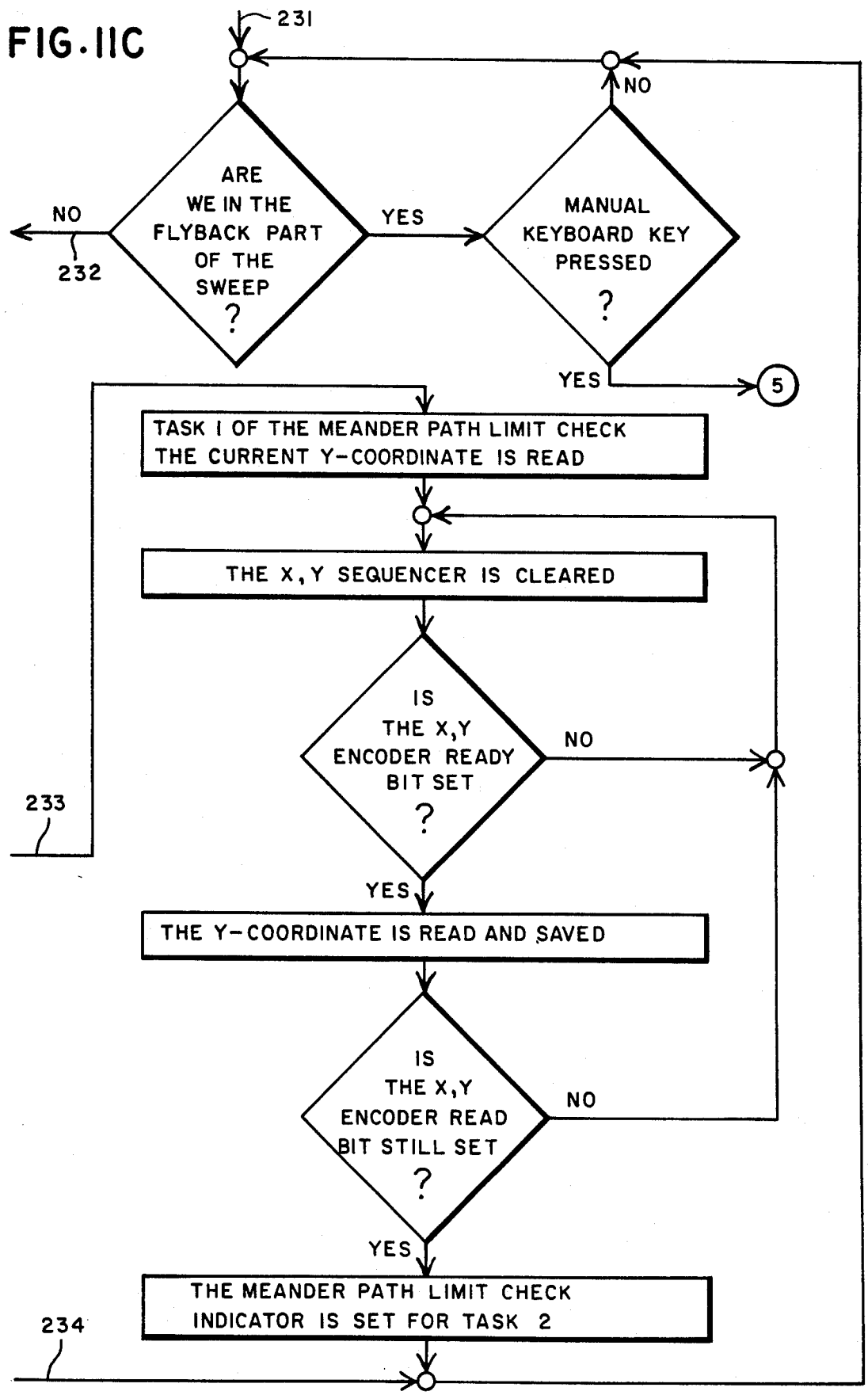
Figure 11D:
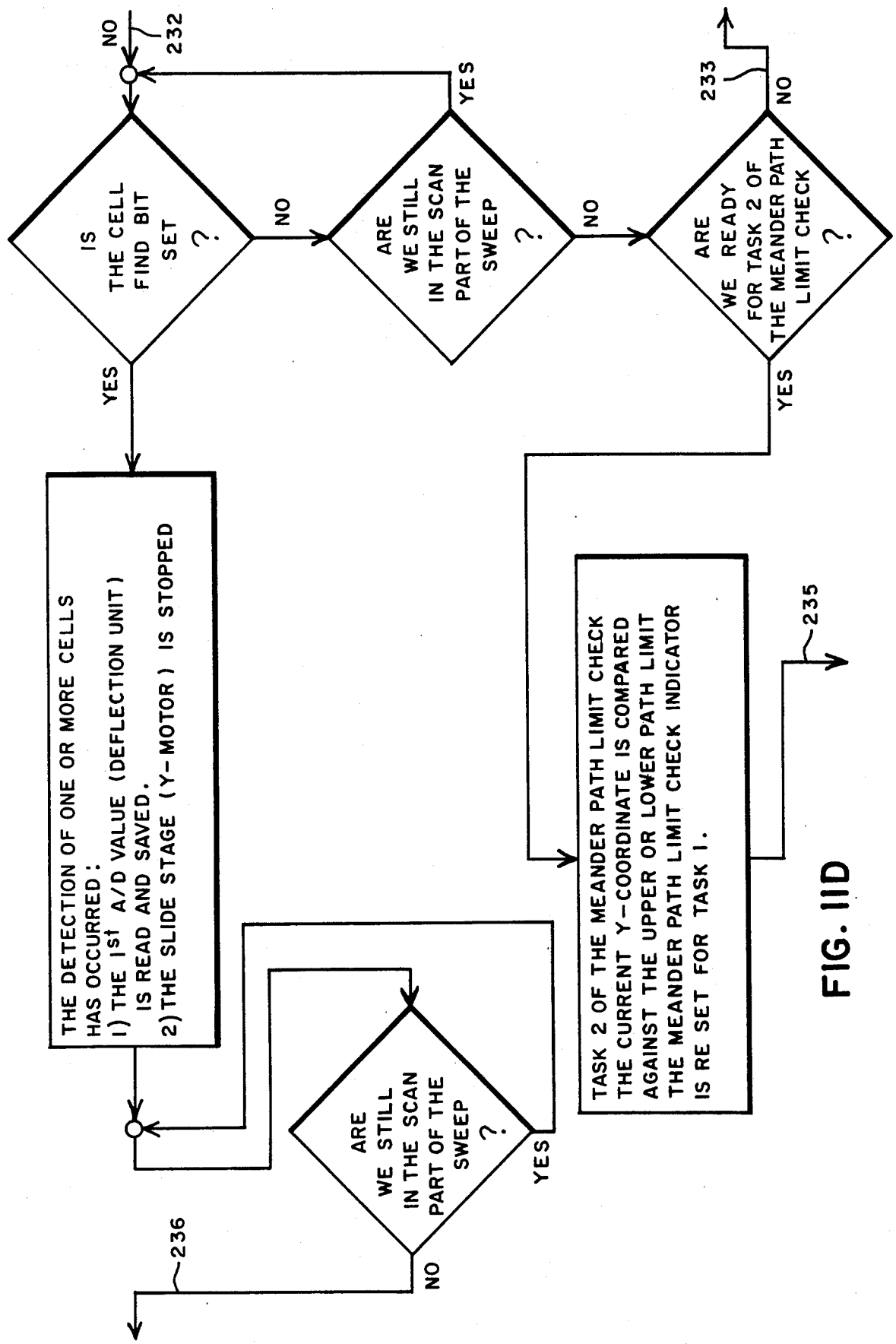
Figure 11E:
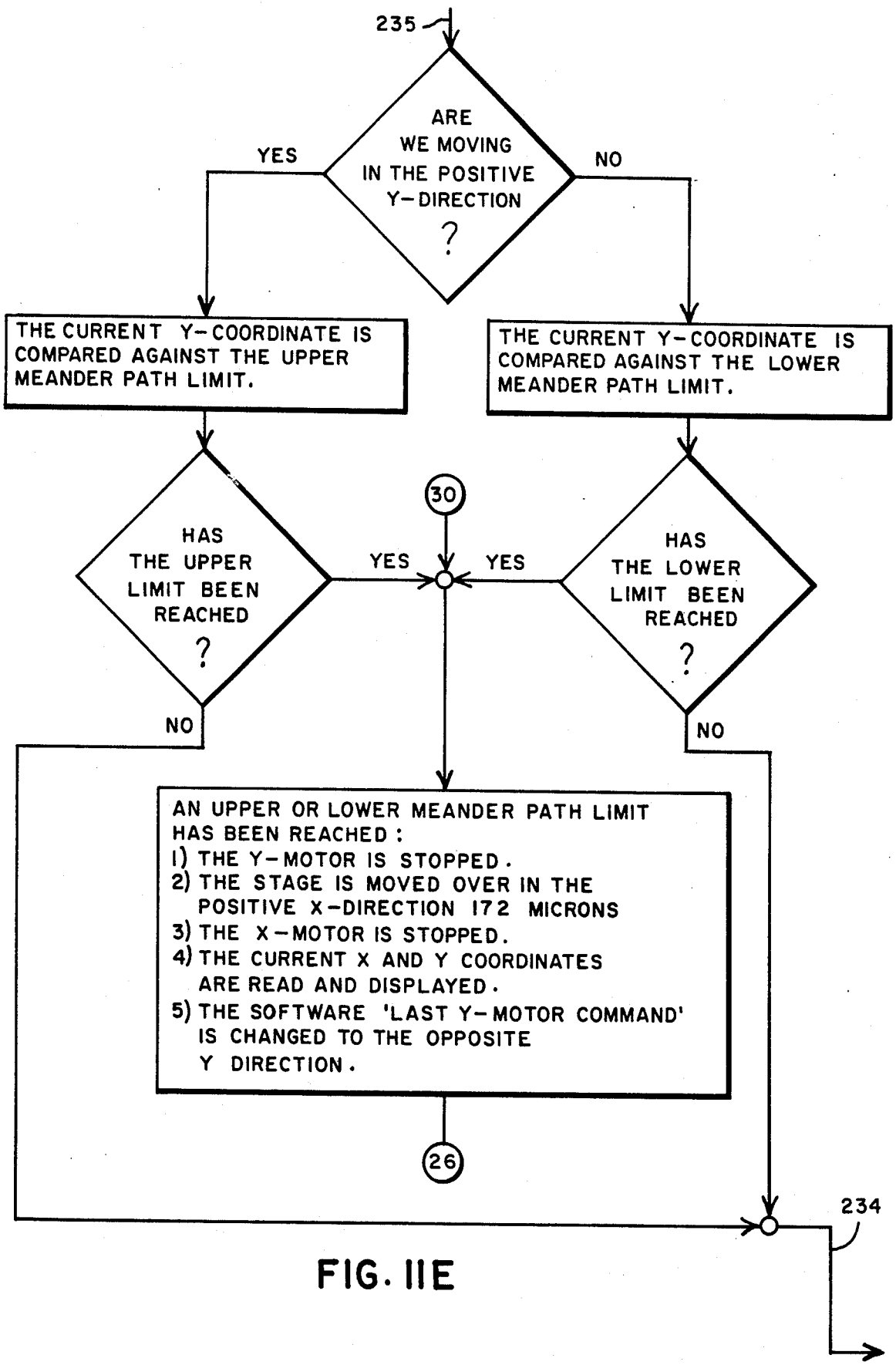
Figure 11F:
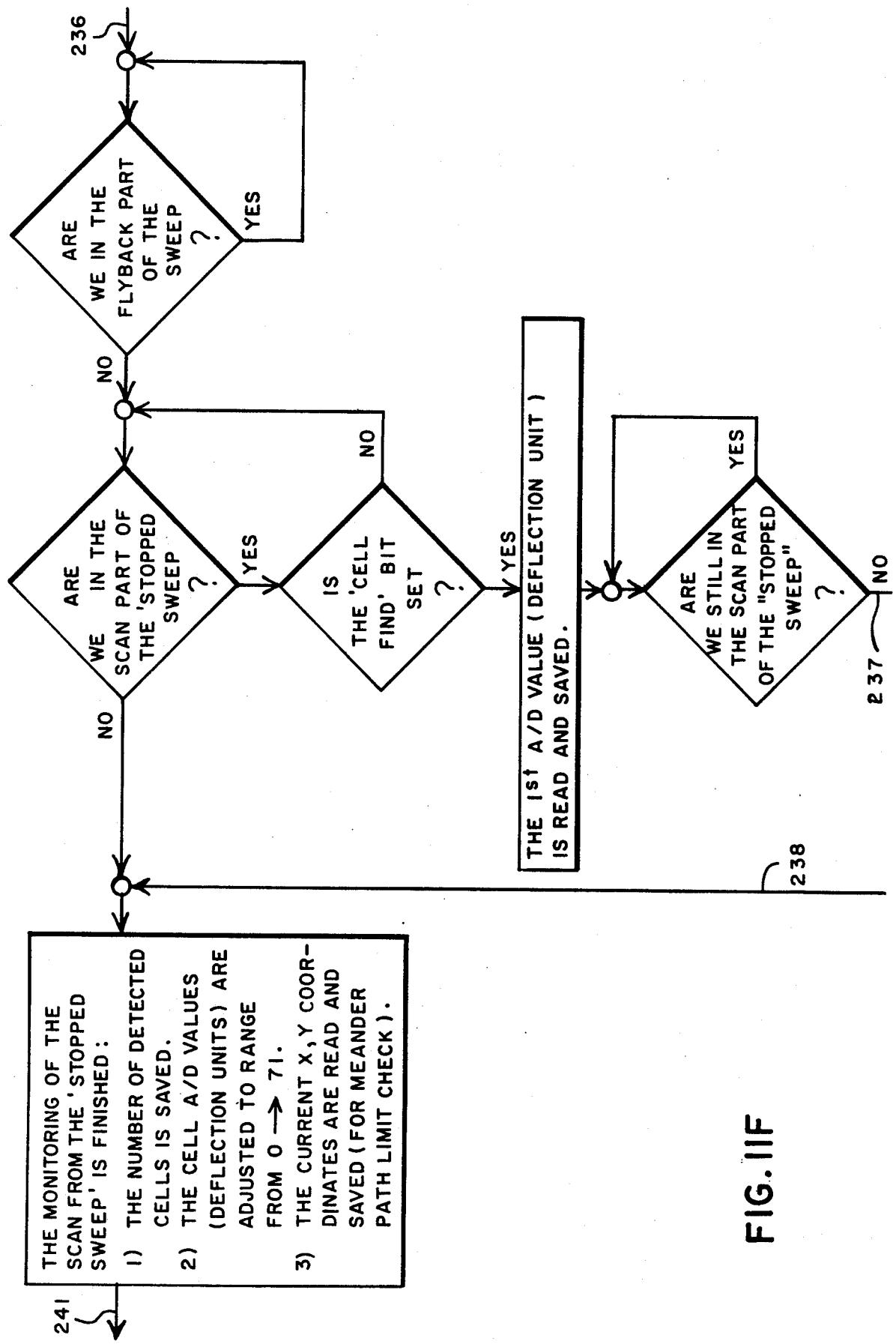
Figure 11H:
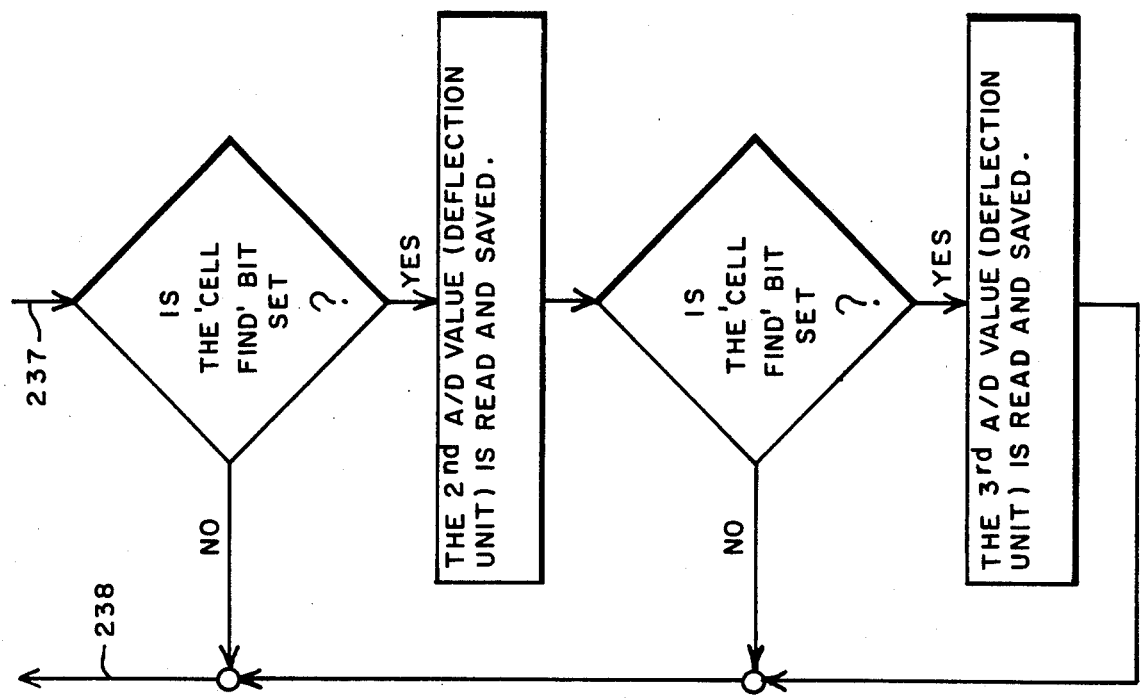
Figure 11H:
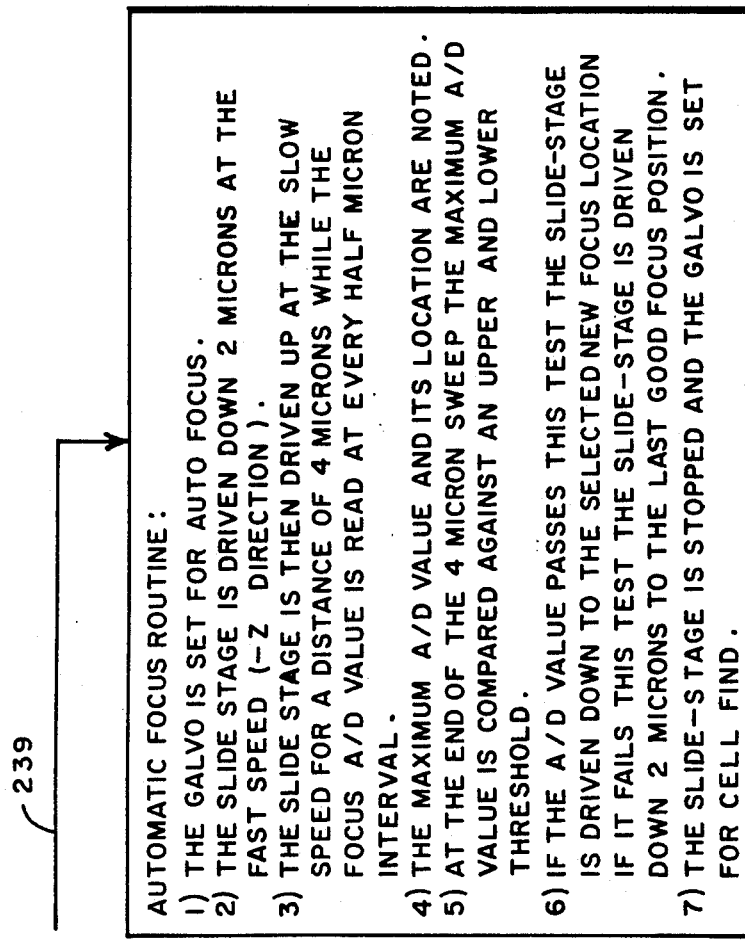

The flow diagram of FIG. 8 comprising FIGS. 8A to 8D is a general diagram showing the overall software operating system and showing functional names for the many routines. Of these routines, several are pertinent to the claimed invention and are shown in FIGS. 9 through 12. FIG. 9 is a flow diagram entitled "X and Y Coordinate Entry Routine" and complements the program routine of Table A which includes the X coordinate entry mode of operation routine (routine to accept 3 digit coordinate and drive to the specified location) and Y coordinate entry mode of operation routine (routine to accept 3 digit coordinate and drive to the specified location).

FIG. 10 comprising FIGS. 10A to 10F is a flow diagram entitled "Keyboard 1: Differential Count Routine" and complements the program routine of Table B which is the Differential Count Mode of Operation Routine.

FIG. 11 comprising FIGS. 11A to 11H is a flow diagram entitled "Automatic Cell-Find Routine (Part 1)" and complements the program routine of Table C which is the "Automatic Cell-Find Routine Capable of Centering on 3 separate cells encountered in any given scan swath."

Figure 12A:
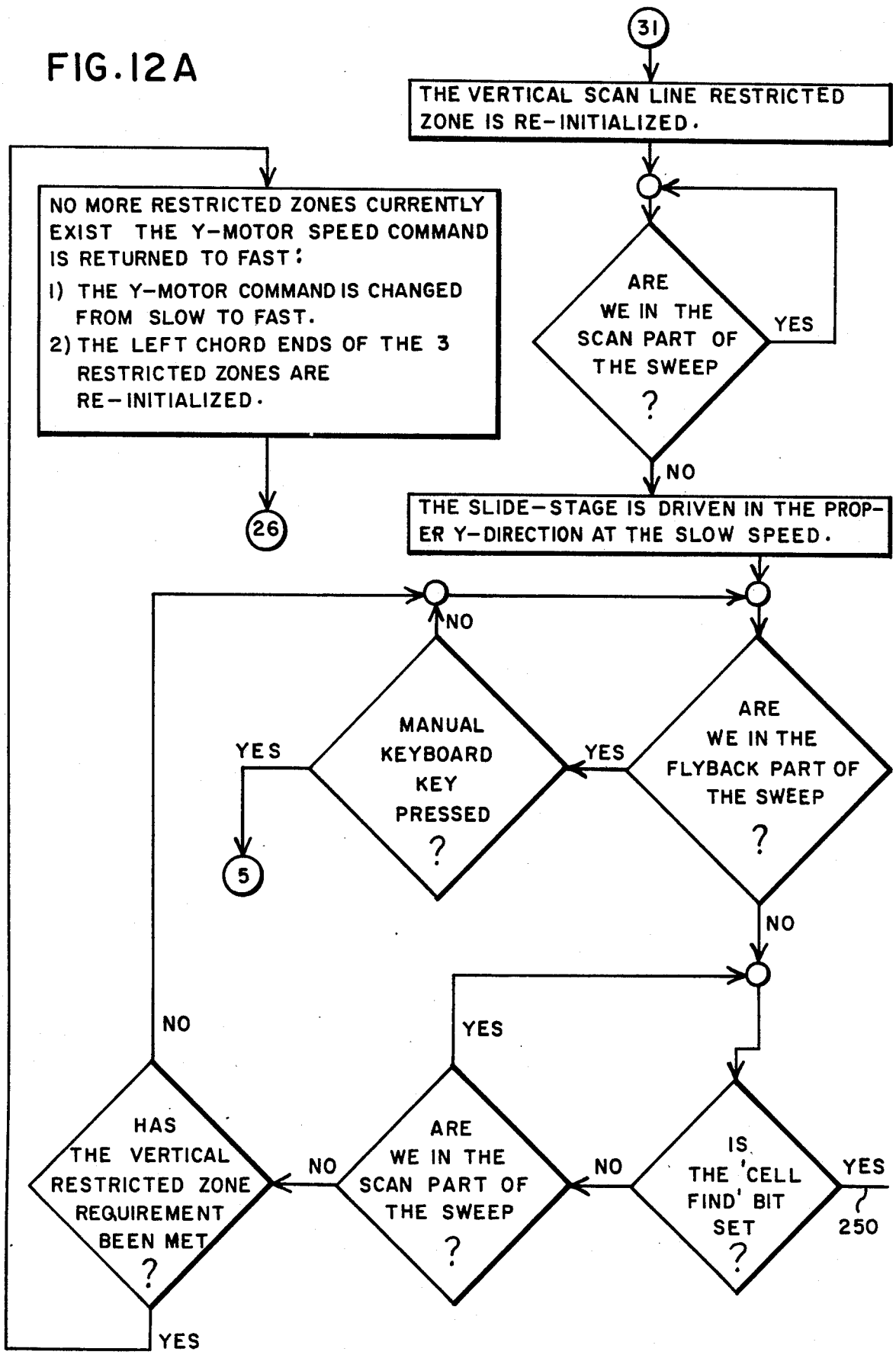
Figure 12B:
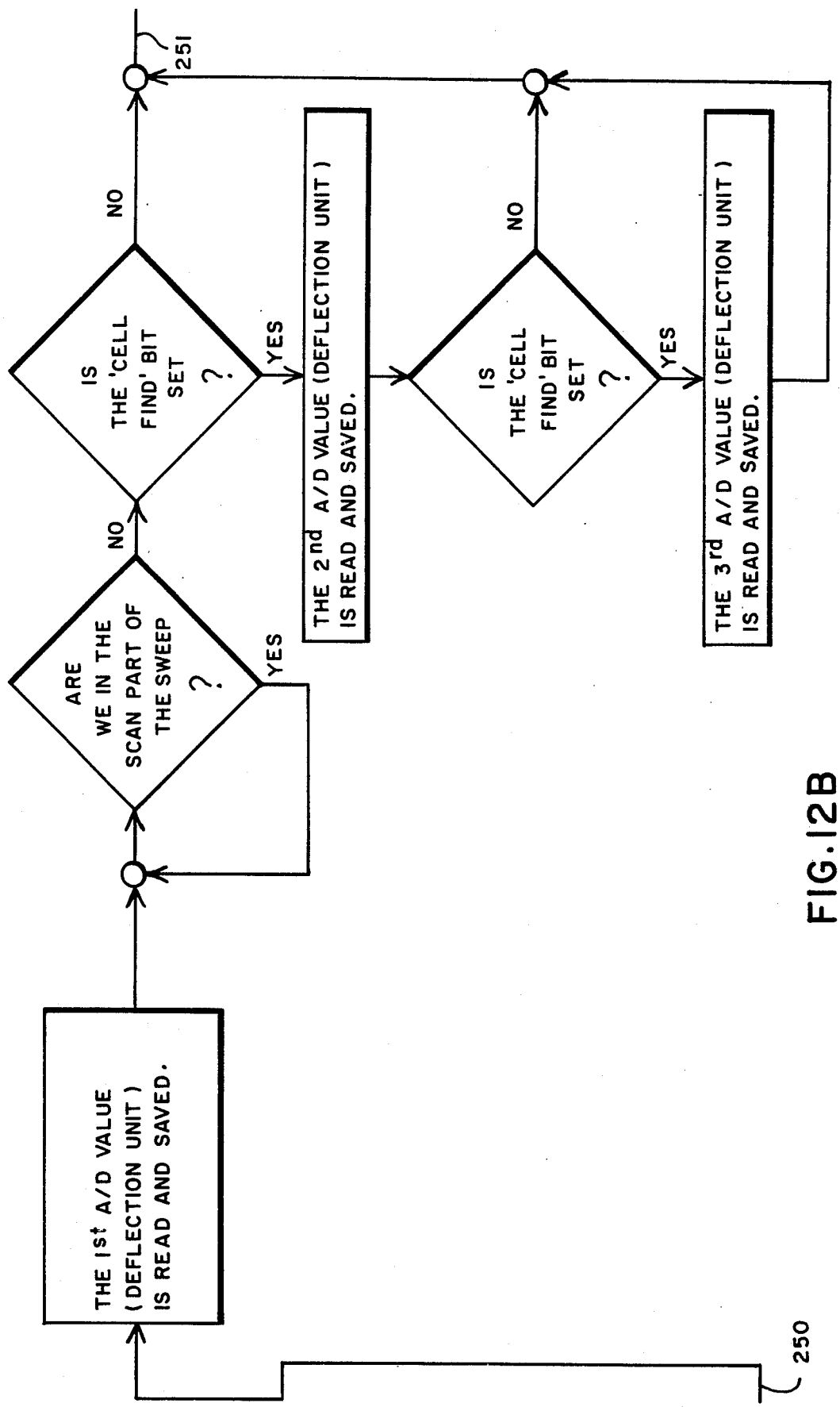
Figure 12D:
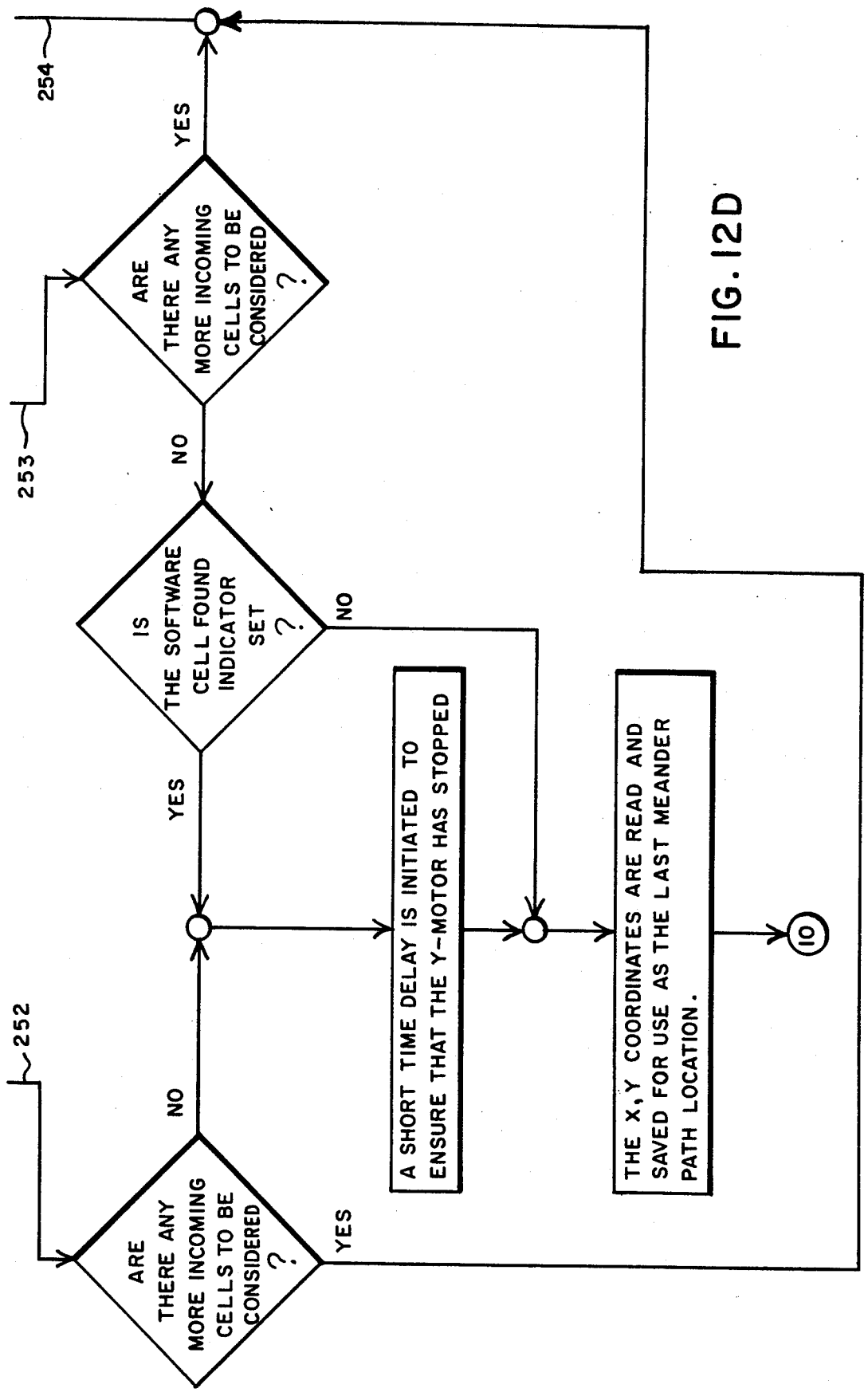

FIG. 12 comprising FIGS. 12A to 12D is a flow diagram entitled "Automatic Cell-Find Routine (Part 2)" and complements the program routine. "Cell-Find Routine, Part 2, used when one or more restricted zones currently exist, Y motor is being driven at slow speed."

TABLE A

```
                            R COORDINATE ENTRY MODE OF OPERATION ROUTINE
                            (ROUTINE TO ACCEPT 3 DIGIT COORDINATE AND
                            DRIVE TO THE SPECIFIED LOCATION)

1788 R8         XENT:   KRA    A           ;CLEAR A
                        LLI    L,CALFL     ;CAL POS DONE YET
1789 3609
178B BF                 CMP    M           ;1=YES
178C 68A317             JZ     NOCAL       ;JUMP IF NOT DONE YET
                        LLI    L, XCO
178F 366B
1791 BE04               MVI    B, 4        ;MAX DIGITS PLUS 1
1793 468A03             CALL   NUMEN
1796 8603               MVI    A, 3H       ;ALL 3 COORDINATES IN?
1798 BA                 CMP    C           ;PRESENT COUNT IN C
1799 482B11             JNZ    KBSCR       ;NOT DONE, GET MORE
                        LLI    L, KYGO     ;ALL COORDINATES ENTERED
179C 36D4
179E 3E01               MVI    M, 1H
17A0 443218             JMP    OKY9
                        ENTRY TO AUTO CELL FIND IS PROHIBITED UNLESS
                        CALIBRATE POSITION HAS BEEN PERFORMED
17A3 460A02     NOCAL   CALL   EHORN       ;SOUND AUDIBLE TONE ALARM
17A6 060F               MVI    A, 0FH      ;FLASH LITE
17AB 468103             CALL   LAMPS
17AB 0646               MVI    A, 46H      ;CLEAR X, Y, & AUTO
17AD 53                 OUT    9
17AE A8                 XRA    A
17AF 53                 OUT    9
17B0 0608               MVI    R, 08H
17B2 55                 OUT    0AH
17B3 A8                 XRA    A
17B4            55      OUT    0AH
17B5 1EDC               MVI    D, 220
17B7 460F07             CALL   TIMR
17BA 061F               MVI    A, 1FH      ;NOW CANCEL LITE
17BC 468103             CALL   LAMPS
                        LLI    L, AFF
17BF 36B7
17C1 3E00               MVI    M, 0H
17C3 30                 INR    L
17C4 3E00               MVI    M, 0H
17C6 44D210             JMP    MANL

Y COORDINATE ENTRY MODE OF OPERATION ROUTINE
                            (ROUTINE TO ACCEPT 3 DIGIT COORDINATE AND
                            DRIVE TO THE SPECIFIED LOCATION)

17C9 A8         YENT:   XRA    A           ;CLEAR A
                        LLI    L, CALFL    ;CAL POS DONE YET
17CA 3609
17CC BF                 CMP    M           ;MUST DO CAL BEFORE Y ENT
17CD 68A317             JZ     NOCAL       ;JUMP IF POS NOT DONE
                        LLI    L, YCO
17D0 366F
17D2 BE04               MVI    B, 04H      ;MAK DIGITS + 1
17D4 468A03             CALL   NUMEN       ;GET & STORE IT
17D7 0603               MVI    A, 3H       ;ALL 3 ENTERED
```

TABLE A-continued

| | | | | |
|---|---|---|---|---|
| 17D9 BA | | CMP | C | ;PRESENT DIGIT COUNT INC |
| 17DA 482B11 | | JNZ | KBSCR | ;JUMP IF NOT DONE |
| 17DD 0602 | | MVI | A, 2 | |
| 17DF 55 | | OUT | 0AH | |
| 17E0 AB | | XRA | A | |
| 17E1 55 | | OUT | 0AH | ;CLEAR MANUAL |
| 17E2 0626 | | MVI | A, 26H | |
| 17E4 53 | | OUT | 09H | |
| 17E5 A8 | | XRA | A | |
| 17E6 53 | | OUT | 09H | |
| | | LLI | L, YCO+3 | ;ALL 3 IN |
| 17E7 3672 | | | | |
| 17E9 C7 | | MOV | A, M | ;GET MSD |
| 17EA 02 | | RLC | | ;SHIFT TO |
| 17EB 02 | | RLC | | ;HIGH NIBBLE |
| 17EC 02 | | RLC | | ;OF A |
| 17ED 02 | | RLC | | |
| 17EE 747B | | ANI | 0F0H | ;AND OFF LOW NIBBLE |
| 17F0 31 | | DCR | L | ;NEXT BYTE (TENS) |
| 17F1 08 | | MOV | B, A | ;MOVE SHIFTED MSD TO B |
| 17F2 07 | | MOV | R, M | ;MID DIGIT OF COORDINATES |
| 17F3 240F | | ANI | 0FH | ;AND OFF HIGH NIBBLE OF TENS |
| 17F5 81 | | ADD | B | ;COMBINE WITH MSD |
| 17F6 D8 | | MOV | D, A | |
| 17F7 31 | | DCR | L | ;UNITS OF COORDINATES |
| 17F8 C7 | | MOV | A, M | ;TO A |
| 17F9 02 | | RLC | | ;SHIFT TO |
| 17FA 02 | | RLC | | ;HIGH NIBBLE |
| 17FB 02 | | RLC | | ;OF A |
| 17FC 02 | | RLC | | ;OF A |
| 17FD 02 | | RLC | | |
| 17EE 24F0 | | ANI | DEBH | ;AND OFF LOW NIBBLE |
| 17F0 31 | | DCR | L | ;NEXT BYTE (TENS) |
| 17F1 C8 | | MOV | B, A | ;MOVE SHIFTED MSD TO B |
| 17F2 C7 | | MOV | A, M | ;MID DIGIT OF COORDINATES |
| 17F3 240F | | ANI | 0FH | ;AND OFF HIGH NIBBLE OF TENS |
| 17F5 81 | | ADD | B | ;COMBINE WITH MSD |
| 17F6 D8 | | MOV | D, A | |
| 17F7 31 | | DCR | L | ;UNITS OF COORDINATES |
| 17F8 C7 | | MOV | A, M | ;TO A |
| 17F9 02 | | RLC | | ;SHIFT TO |
| 17FA 02 | | RLC | | ;HIGH NIBBLE |
| 17FD 02 | | RLC | | ;OF A |
| 17FC 02 | | RLC | | |
| 17FD 24F0 | | ANI | 0F0H | ;AND OF LOW NIBBLE NOW |
| 17FF 0408 | | ADI | 08H | ;ADD ENCODER MID-RANGE |
| 1801 E0 | | MOV | E, A | ;AND MOE TO E |
| 1882 469106 | | CALL | YPET | ;GO THERE |
| | | LLI | L, XCO+3 | ;DESIRED MID COORDINATE |
| 1805 366E | | | | |
| 1807 C7 | | MOV | A, M | ;TO A |
| 1808 02 | | RLC | | ;MOVE TO |
| 1809 02 | | RLC | | ;HIGH NIBBLE |
| 180A 02 | | RLC | | ;OF A |
| 180B 02 | | RLC | | |
| 180C 24F0 | | ANI | 0F0H | ;AND OFF LOW NIBBLE |
| 180E 31 | | DCR | L | ;NEXT COORDINATE (TENS) |
| 180F C8 | | MOV | B, A | ;SHIFTED MSD TO B |
| 1810 C7 | | MOV | A, M | ;TENS TO A |
| 1811 240F | | ANI | 0FH | ;AND OFF ANY SPARES |
| 1813 81 | | ADD | B | ;COMBINE WITH MSD |
| 1814 D8 | | MOV | D, A | ;MOVE TO D |
| 1815 31 | | DCR | L | ;NEXT BYTE - UNITS OF COORD. |
| 1816 C7 | | MOV | A, M | ;TO A |
| 1817 02 | | RLC | | ;SHIFT TO |
| 1818 02 | | RLC | | ;HIGH NIBBLE |
| 1819 02 | | RLC | | ;OF A |
| 181A 02 | | RLC | | |
| 181B 24F0 | | ANI | 0F0H | ;AND OFF SPARES |
| 181D 0408 | | ADI | 08H | ;ADD ENCOPER MID-RANGE TO LSD |
| 181F E0 | | MOV | E, A | ;MOVE TO E |
| 1820 466406 | | CALL | XRET | ;MOVE TO E |
| | | LLI | L, XYGO | |
| 1823 36D4 | | | | |
| 1825 3E00 | | MVI | M, 0H | |
| 1827 A8 | | XRA | A | ;CHECK FOR FOCUS |
| | | LLI | L, AFF | ;FOCUS FLAG |
| 1828 36B7 | | | | |
| 182A BF | | CMP | M | |
| 182B 4A6D1E | | CNZ | FOCUS | ;FLAG UP, FOCUS |
| | OXY: | LLI | L, XYGO | ;CLEAR X, Y PROPER ENTRY FLAG |
| 182E 36D4 | | | | |
| 1830 3E00 | | MVI | M, 0 | |
| 1832 0646 | OXY9: | MVI | A, 46H | ;CODE FOR LIGHT |
| 1834 53 | | OUT | 09H | ;EXTINGUISH |
| 1835 A8 | | XRA | A | |
| 1836 53 | | OUT | 09H | |
| | | LLI | L, LMODE | ;CLEAR MODE OF OPERATION INDICAT |
| 1837 360B | | | | |
| 1839 3E00 | | MVI | M, 0 | |
| 183B 45 | | IN | 2 | |
| 183C 47 | | IN | 3 | |

TABLE A-continued

| 183D 44D210 | | JMP | MANL | |

TABLE B

```
            ;
            ;           DIFFERENTIAL COUNT MODE OF OPERATION ROUTINE
            ;
                DIFF:   LLI     L, DATFL    ; DATA IN FLAG
18B2 36BA
18B4 C7             MOV     A, M
18B5 3C00           CPI     0H          ; 1=DATA, 0=MODE, LAST READ
18B7 482215         JNZ     THDU        ; ZERO?
18BA 061F           MVI     A, 1FH      ; JUMP IF DATA
18BC 468103         CALL    LAMPS       ; TURN OFF BANK B LITES
                    LLI     L, ACFF     ; CHECK IF AUTO CELL FIND LITE
18BF 36BB
18C1 A8             XRA     A           ; SHOULD BE TURNED BACK ON
18C2 BF             CMP     M
18C3 060D           MVI     A, 0DH      ; AUTO CELL FIND LITE CODE
18C5 4A8103         CNZ     LAMPS
18C8 0607           MVI     A, 07H      ; LAMP ADDR OF DIFF
18CA 468103         CALL    LAMPS       ; LITE THE LIGHT
18CD 469600         CALL    DDIP        ; DISPLAY COUNTS
                    LLI     L, BEFOR    ; FLAG FOR BEEN HERE BEFORE
18D0 36CB
18D2 A8             XRA     A           ; CLEAR A
18D3 BF             CMP     M           ; 0= NOT HERE BEFORE
18D4 48E018         JNZ     DIF1        ; THIS IS OLD STUFF GO BACK
18D7 3E01           MVI     M, 1H       ; SET FLAG
                    LLI     L, HCNT     ; BEEN TO RETIC WITHOUT A CLEAR,
18D9 36B1
18DB 3E00           MVI     M, 0        ; RESET COUNTERS
18DD 30             INR     L
18DE 3E00           MVI     M, 0H
                DIF1:   LLI     L, ACFF
18E0 36B8
18E2 C7             MOV     A, M
18E3 3C00           CPI     0H
18E5 68D210         JZ      MANL
                    LLI     L, REMAN
18E8 36DB
18EA CF             MOV     B, M
18EB C1             MOV     A, B
18EC 3C01           CPI     1H
18EE 60971B         JC      CEL6        ; GO TO LOOK FOR MORE CELLS
            ;       SECTION TO RETURN STAGE TO LAST
            ;       UNIDENTIFIED CELL
18F1 465F06     DIF2:   CALL    RMPX        ; RETURN TO LAST MEANDER PATH POS
18F4 468C06         CALL    RMPY
                    LLI     L, DEFLT
18F7 36D7
18F9 D7             MOV     C, M
18FA A8             XRA     A
18FB BF             CMP     M           ; IF CELL ALREADY NEAR CENTER,
18FC 68081D         JZ      CEL28       ; SKIP CENTERING PROCESS
18FF 30             INR     L
1900 44F51C         JMP     CEL26       ; GO TO CENTER ON CELL
                DIF3:   LLI     L, ENTRY    ; SET MULTIPLE ENTRY MADE FLAG
1903 36E6
1905 3E01           MVI     M, 1
                    LLI     L, KBID     ; CHECK DATA FOR VALIDITY
1907 36B5
1909 C7             MOV     A, M        ; KEYBOARD 1 DATA
190A C8             MOV     B, A        ; SAVE IN B
190B 3001           CPI     01H         ; 1=RETIC NO VALID
190D 682919         JZ      DIF5        ; JUMP IF RETIC
1910 3C08           CPI     08H         ; 2-7H IS VALID
1912 603019         JC      DIF6        ; GO IF VALID
1915 300C           CPI     0CH         ; B-0BH INVALID
1917 602919         JC      DIF5        ; JUMP IF NO GOOD
191A 3C13           CPI     13H         ; 0C-12H IS VALID
191C 603A19         JC      DIF6-2      ; JUMP IF VALID
            ;       COULD BE A SKIP OR CANCEL
191F 3C16       DIF4:   CPI     16H         ; CODE FOR CANCEL
1921 68041A         JZ      DIF17       ; GO FOR CANCEL
1924 3C17           CPI     17H         ; HOW ABOUT A SKIP
1926 682F19         JZ      DIF5A       ; GO FOR FURTHER CHECKS
1929 460A02     DIF5:   CALL    EHORN       ; BUZZ HORN FOR MISTAKE
192C 442B11         JMP     KBSCR       ; GO BACK TO KEYBOARD
                DIF5A:  LLI     L, T2FLG
192F 36E7
1931 3E00           MVI     M, 00H
                    LLI     L, T3FLG
1933 36E8
1935 3E00           MVI     M, 00H
1937 448819         JMP     DIF7
            ;       REMOVE BIAS FOR CELL COUNT
193A 1404           SUI     04H         ; FOR C-12 SUBTRACT 4 MAKING 1-0E
                DIF6:   LLI     L, ASAVE
193C 36E9
```

TABLE B-continued

| | | | | |
|---|---|---|---|---|
| 193E F8 | | MOV | M, A | |
| | | LLI | L, MULTF | |
| 193F 36BD | | | | |
| 1941 C7 | | MOV | A, M | |
| 1942 3000 | | CPI | 00H | |
| 1944 684D19 | | JZ | DIF6A | |
| | | LLI | L, ASAVE | |
| 1947 36E9 | | | | |
| 1949 C7 | | MOV | A, M | |
| 194A 445819 | | JMP | DIF6B | |
| | DIF6A: | LLI | L, T3FLG | |
| 194D 36E8 | | | | |
| 194F C7 | | MOV | A, M | |
| 1950 3C01 | | CPI | 01H | |
| 1952 682B11 | | JZ | KBSCR | |
| | | LLI | L, ASAVE | |
| 1955 36E9 | | | | |
| 1957 C7 | | MOV | A, M | |
| 1958 2E00 | DIF6B: | MVI | H, O | ; SET H-REG FOR TABLE LOOKUP |
| | | LLI | L, CTABL | ; TABLE OF OFFSET AND |
| 195A 361A | | | | |
| | ; | | DISPLAY ADDR FOR CELL TYPES | |
| 195C 80 | | ADD | A | ; DOUBLE A |
| 195D 1402 | | SUI | 02H | ; CORRECT ADDR NOW |
| 195F 86 | | ADD | L | ; ADD TO BASE ADDR OF TABLE |
| 1960 F0 | | MOV | L, A | ; AND PUT IN L |
| 1961 C7 | | MOV | A, M | ; GET OFFSET OF CELL COUNT |
| 1962 30 | | INR | L | ; NEXT BYTE IS DISPLAY ADDR |
| 1963 CF | | MOV | B, M | ; B IS PROPER REG FOR ADDR |
| 1964 2E08 | | MVI | H, S | ; RESET H-REG FOR RAM MEMORY |
| | | LLI | L, LAST | ; STORE THIS AS LAST CELL |
| 1966 36AD | | | | |
| 1968 F8 | | MOV | M, A | ; LAST OFFSET |
| 1969 30 | | INR | L | ; NOW LED ADDR |
| 196A F9 | | MOV | M, B | ; STORE ADDR OF LAST LED |
| | | LLI | L, CELL | ; CELL COUNT ARRAY |
| 196B 360D | | | | |
| 196D 86 | | ADD | L | ; ADD THE OFFSET IN A TO BASE |
| 196E F0 | | MOV | L, A | ; AND PUT IN L |
| 196F 466A00 | | CALL | COUNT | ; INCREMENT PROPER COUNT |
| 1972 46F801 | | CALL | DISP | ; FLASH NEW COUNT |
| 1975 0601 | | MVI | A, 01H | ; LED ADDR OF RNBC |
| 1977 B9 | | CMR | B | ; IS THIS A NRBC |
| 1978 688819 | | JZ | DIF7 | ; DONT INCREMENT TOTALS IF NRBC |
| | | LLI | L, TOTL+2 | ; GET TOTAL CELL COUNT |
| 197B 3669 | | | | |
| 197D 466A00 | | CALL | COUNT | ; INCREMENT TOTALS COUNT |
| 1980 0E00 | | MVI | B, 0H | ; LED ADDR OF TOTALS |
| 1982 46F801 | | CALL | DISP | ; FLASH NEW TOTAL |
| 1985 44B61A | | JMP | DIF21 | ; UP THE BINARY COUNTER |
| | DIF7: | LLI | L, REFLG | |
| 1988 366A | | | | |
| 198A C7 | | MOV | A, M | |
| 198B 3C00 | | CPI | 0H | |
| 198D 485418 | | JNZ | RET1 | |
| | | LLI | L, MULTF | ; MULT ENTRY FLAG |
| 1990 36BD | | | | |
| 1992 C7 | | MOV | A, M | ; 1=ON 0=OFF |
| 1993 3C00 | | CPI | 0H | ; ZERO? |
| 1995 482B11 | | JNZ | KBSCR | |
| | | LLI | L, PERGO | ; CHECK FOR CANCEL CONDITION |
| 1998 36BC | | | | |
| 199A C7 | | MOV | A, M | ; 0=NO CANCEL COND |
| 199B 3C00 | | CPI | 0H | ; 1,2 MULT ENTRY FOR CANCEL |
| 199D 68A619 | | JZ | DIF8 | ; NO MULT CHECK FOR FIND |
| 19A0 1401 | | SUI | 01H | ; DEC NUMBER OF ENTRIES |
| 19A2 F8 | | MOV | M, A | ; RESTORE DIGIT COUNTER |
| 19A3 422B11 | | JMP | KBSCR | |
| | ; | | IS THE CELL FIND FLAG SET | |
| | DIF8: | LLI | L, ACFF | ; FLAG FOR CELL FIND UP |
| 19A6 36B8 | | | | |
| 19A8 C7 | | MOV | A, M | |
| 19A9 3C00 | | CPI | 0H | |
| 19AB 68D210 | | JZ | MANL | ; IF NOT CELL FIND THEN MANUAL |
| | ; | | NOW RETURN TO MEANDER PATH BY COUNTING PULSES | |
| | DIF9: | LLI | L, T2FLG | |
| 19AE 36E7 | | | | |
| 19B0 C7 | | MOV | A, M | |
| 19B1 3C01 | | CPI | 01H | |
| 19B3 68BE19 | | JZ | TILT | |
| 19B6 0608 | | MVI | A, 0BH | |
| 19B8 5B | | OUT | 0DH | |
| 19B9 A8 | | XRA | A | |
| 19BA 5B | | OUT | 0DH | |
| 19BB 44CA19 | | JMP | DIF9A | |
| 19BE 0610 | TILT: | MVI | A, 10H | |
| 1900 5B | | OUT | 0DH | |
| 1901 A8 | | XRA | A | |
| 1902 5B | | OUT | 0DH | |
| | | LLI | L, T3FLG | |
| 1903 36E8 | | | | |
| 1905 3E01 | | MVI | M, 01H | |
| 1907 442B11 | | JMP | KBSCR | |

TABLE B-continued

```
                   DIF9A:  LLI    L, DEFLT
190A  36D7
190C  D7                   MOV    C, M         ; NUMBER OF PULSES
19CD  A8                   XRA    A
19CE  BA                   CMP    C            ; ARE WE ON PATH?
19CF  68E719               JZ     DIF11        ; YES
19D2  30                   INR    L
19D3  C7                   MOV    A, M
19D4  59                   OUT    0CH          ; MOTOR COMMAND TO RETURN TO PATH
19D5  464E07       DIF10:  CALL   WTXY         ; RETURN AT A PULSE
19D8  11                   DCR    C
19D9  48D519               JNZ    DIF10
19DC  0608                 MVI    A, 08H       ; BACK, STOP MOTOR
19DE  59                   OUT    0CH
19DF  1EFB                 MVI    D, 0FBH
19E1  460F07               CALL   TIMR
19E4  46271E               CALL   RMP1
                    ;      CHECK TO SEE IF ANY MORE CELLS LEFT TO BE CENTE
                   DIF11:  LLI    L, REMAN
19E7  36DB
19E9  C7                   MOV    A, M
19EA  1401                 SUI    1
19EC  F8                   MOV    M, A
19ED  C8                   MOV    B, A
19EE  3C00                 CPI    0
19F0  68041A               JZ     DIF12
                           LLI    L, QUE+2
19F3  36DE
19F5  C6                   MOV    A, L
19F6  81                   ADD    B
19F7  F0                   MOV    L, A
19F8  C7           ENHER:  MOV    A, M
19F9  3C80                 CPI    80H
19FB  60CD1C               JC     CEL25        ; GO TO CENTER CELL
19FE  247F                 ANI    7FH
1A00  F8                   MOV    M, A
1A01  44E719               JMP    DIF11
                    ;      CHECK MEANDER PATH LIMITS
                   DIF12:  LLI    L, YCOM      ; CHANGE TO SLOW SPEED IF NEC.
1A04  36C5
1A06  C7                   MOV    A, M
1A07  2401                 ANI    1
1A09  68251A               JZ     DIF13
1A0C  3E0D                 MVI    M, 0DH       ; SET Y TO SLOW +
                           LLI    L, HIYL      ; NOW CHECK FOR MEANDER LIMITS
1A0E  36C3
1A10  C7                   MOV    A, M
1A11  30                   INR    L
1A12  CF                   MOV    B, M
                           LLI    L, LMP+2
1A13  36C8
1A15  BF                   CMP    M
1A16  60521C               JC     CEL16        ; AT OR PAST LIMIT, REVERSE
1A19  483B1A               JNZ    DIF14
1A1C  C1                   MOV    A, B         ; LSB OF LIMIT
1A1D  30                   INR    L
1A1E  BF                   CMP    M
1A1F  60521C               JC     CEL16        ; PAST LIMIT, REVERSE
1A22  443B1A               JMP    DIF14        ; WITHIN LIMITS CONTINUE
1A25  3E0C         DIF13:  MVI    M, 0CH       ; SLOW DOWN
                           LLI    L, LMP+2
1A27  36C8
1A29  C7                   MOV    A, M         ; CHECK LIMIT
1A2A  30                   INR    L
1A2B  CF                   MOV    B, M
                           LLI    L, LOYL      ; MEANDER LIMITS-LOW
1A2C  36C1
1A2E  BF                   CMP    M
1A2F  60521C               JC     CEL16        ; PAST LIMIT
1A32  483B1A               JNZ    DIF14        ; BETWEEN LIMITS STILL
1A35  C1                   MOV    A, B
1A36  30                   INR    L            ; CHECK LSB IF MSB =
1A37  BF                   CMP    M
1A38  60521C               JC     CEL16        ; JUMP IF PAST LIMIT
                    ;      SET UP RESTRICTED ZONES FOR ANY CURRENT CELLS
                   DIF14:  LLI    L, LSIDE
1A3B  36E1
1A3D  0678                 MVI    A, 120
1A3F  F8                   MOV    M, A
1A40  30                   INR    L
1A41  F8                   MOV    M, A
1A42  30                   INR    L
1A43  F8                   MOV    M, A
                           LLI    L, QUE
1A44  36DC
1A46  CF                   MOV    C, M         ; PICK UP NUMBER OF CELLS
1A47  1600                 MVI    C, 0
                   DIF15:  LLI    L, QUE+2
1A49  36DE
1A4B  C6                   MOV    A, L
1A4C  82                   ADD    C
1A4D  F0                   MOV    L, A
1A4E  C7                   MOV    A, M         ; PICK UP DEFLECTION VALUE (0-70)
```

TABLE B-continued

```
1A4F 140A                SUI    1D
1A51 40551A              JNC    DIF16
1A54 A8                  XRA    A
1A55 D8        DIF16:    MOV    D, A
                         LLI    L, LSIDE
1A56 36E1
1A58 C6                  MDV    A, L
1A59 82                  ADD    C
1A5A F0                  MOV    L, A
1A5B FB                  MOV    M, D
1A5C 10                  INR    C
1A5D 09                  DCR    B
1A5E 48491A              JNZ    DIF15
1A61 44571D              JMP    CEL29       ; GO TO LOOK FOR MORE CELLS
               ;         SECTION TO CANCEL LAST ENTRY
               DIF17:    LLI    L, LAST     ; CANCEL LAST CELL ENTERED
1A64 36AD
1A66 C7                  MOV    A, M        ; OFFSET OF LAST TYPE
1A67 3C00                CPI    0H          ; 0 OFFSET=CANCEL LAST
1A69 48721A              JNZ    DIF18       ; JUMP IF LAST WAS CELL
1A6C 460A02              CALL   EHORN       ; THATS A NO-NO
1A6F 442B11              JMP    KBSCR       ; WHAT NOW PERSON
1A72 3E00      DIF18:    MVI    M, 0H       ; SET LAST TO CANCEL=0
1A74 30                  INR    L           ; STORED LED ADDR
1A75 CF                  MOV    B, M        ; FOR CANCEL
                         LLI    L, CELL     ; BASE ADDR OF COUNTS
1A76 360D
1A78 86                  ADD    L           ; ADD OFFSET IN A TO BASE
1A79 F0                  MOV    L, A        ; CORRECT ADDR
1A7A 46B900              CALL   DECR        ; DECREMENT COUNT FOR CELL
                         LLI    L, ASAVE
1A7D 36E9
1A7F FA                  MOV    M, C
                         LLI    L, MULTF    ; PICK UP MULTIPLE ENTRY INFORMAT
1A80 36BD
1A82 D7                  MOV    C, M
                         LLI    L, ENTRY    ; CLEAR MULTIPLE ENTRY MADE FLA
1A83 36E6
1A85 3E00                MVI    M, 0
                         LLI    L, PERGO    ; DETERMINE REQUIRED ENTRIES
1A87 36BC
1A89 0602                MVI    A, 2        ; INFORMATION
1A8B 92                  SUB    C
1A8C 92                  SUB    C
1A8D F8                  MOV    M, A
                         LLI    L, ASAVE
1A8E 36E9
1A90 D7                  MOV    C, M
1A91 06FF                MVI    A, 0FFH     ; CHECK FOR RETIC
1A93 B9                  CMP    B           ; CANT DISPLAY RETICS
1A94 63A01A              JZ     DIF19       ; SKIP NEXT IF RETIC
1A97 46F801              CALL   DISP        ; FLASH NEW COUNT ON DISPLAYS
1A9A 0601                MVI    A, 01H      ; FLASH FOR NRBC
1A9C B9                  CMP    B           ; DONT DEC TOTAL IF NRBC
1A9D 688819              JZ     DIF7        ; JUMP IF NRBC
               DIF19:    LLI    L, TOTL+2   ; ADDR OF TOTALS
1AA0 3669
1AA2 30                  INR    L           ; CHECK FOR RETIC CANCEL
1AA3 A8                  XRA    A           ; CLEAR A
1AA4 BF                  CMP    M           ; 1=RETIC
1AA5 68AA1A              JZ     DIF20
                         LLI    L, RETD+9   ; RETIC TOTALS
1AA8 363D
1AAA 31        DIF20:    DCR    L           ; GET TOTAL
1AAB 46B900              CALL   DECR        ; DECREMENT TOTALS COUNT
1AAE 0E00                MVI    B, 0H       ; LED ADDR OF TOTALS
1AB0 46F801              CALL   DISP        ; FLASH NEW TOTALS ON BOARD
1AB3 44E11A              JMP    DIF23       ; DECREMENT BINARY COUNTER
               ;         INCREMENT BINARY COUNTER AND CHECK AGAINST LIMI
               DIF21:    LLI    L, HCNT     ; ADDR OF HEN COUNTER
1A86 36B1
1AB8 CF                  MOV    B, M        ; LD BYTE TO B
1AB9 08                  INF    B           ; INCREMENT COUNT
1ABA F9                  MOV    M, B        ; SAVE IT
1ABB 48021A              JNZ    DIF22       ; JUMP IF NO CARRY
1ABE 30                  INR    L           ; WAS A CARRY, ADDR OF HI BYTE
1ABF CF                  MOV    B, M        ; TO B REG
1AC0 08                  INR    B           ; BUMP B BY ONE
1AC1 F9                  MOV    M, B        ; SAVE IT
               ;         ROUTINE TO CHECK CELL COUNTS
               DIF22:    LLI    L, HCNT     ; HEX CELL COUNT
1AC2 36B1
1AC4 CF                  MOV    B, M        ; STORE LO BYTE IN B
1AC5 30                  INR    L           ; NEXT BYTE
1AC6 C7                  MOV    A, M        ; HI BYTE OF COUNT TO A
                         LLI    L, CLIM+1   ; SET COUNT LIMIT
1AC7 36B0
1AC9 BF                  CMP    M           ; COMPARE HI BYTES
1ACA 488819              JNZ    DIF7        ; JUMP IF DEFINATELY NOT=
1ACD 31                  DCR    L           ; HI-HI CHECK LO
1ACE C7                  MOV    A, M        ; LO BYTE OF LIMIT
1ACF B9                  CMP    B           ; COMPARE TO LO OF COUNT
1AD8 488819              JNZ    DIF7        ; JUMP IF LIMIT NE COUNT
```

TABLE B-continued

|  |  |  |  |  |
|---|---|---|---|---|
|  | ; | COUNT EQ LIMIT INFORM OPERATOR AND CONVERT TO | | |
|  | ; | PERCENT IF DIFF WAS ENTERED | | |
| 1AD3 460A02 |  | CALL | EHORN | |
|  |  | LLI | L, GOBAC | ; SET RETURN TO DIFF FLAG |
| 1AD6 36E5 |  |  |  | |
| 1AD8 3E01 |  | MVI | M, 1 | |
|  |  | LLI | L, LMODE | |
| 1ADA 360B |  |  |  | |
| 1ADC 3E21 |  | MVI | M, 21H | ; SET LAST MODE TO PERCH |
| 1ADE 449C14 |  | JMP | PER13 | |
|  | ; | ROUTINE TO DECREMENT HEX COUNT FOR A CANCEL | | |
|  | DIF23: | LLI | L, HCNT | ; ADDR OF HEX COUNT |
| 1AE1 36B1 |  |  |  | |
| 1AE3 CF |  | MOV | B, M | ; LO BYTE TO B |
| 1AE4 09 |  | DCR | B | ; DECREMENT LO BYTE |
| 1AE5 F9 |  | MOV | M, B | ; STORE |
| 1AE6 06FF |  | MVI | A, 0FFH | ; BORROW? |
| 1AE8 B9 |  | CMP | B | ; B=OFFH THEN YES |
| 1AE9 48C21A |  | JNZ | DIF22 | ; JUMP IF NO BORROW |
| 1AEC 30 |  | INR | L | ; HI ORDER BYTE |
| 1AED CF |  | MOV | B, M | ; PUT IN B |
| 1AEE 09 |  | DCK | B | ; DECREMENT THAT |
| 1AEF F9 |  | MOV | M, B | ; STORE BACK |
| 1AF0 44C21A |  | JMP | DIF22 | ; NOW COMPARE COUNT TO LIMIT |

TABLE C

|  |  |  |  |  |
|---|---|---|---|---|
|  | ; | AUTOMATIC CELL FIND ROUTINE CAPABLE OF | | |
|  | ; | CENTERI | | |
|  | ; | ON 3 SEPARATE CELLS ENCOUNTERED IN ANY GIVEN | | |
|  | ; | SCAN SWATH) | | |
|  | ; | | | |
|  | ; | SET UP MEANDER PATH LIMITS | | |
|  | CELFND: | LLI | L, CALFL | ; CALIBRATION DONE |
| 1AF3 3609 |  |  |  | |
| 1AF5 0601 |  | MVI | A, 1 | |
| 1AF7 BF |  | CMP | M | |
| 1AF8 48A317 |  | JNZ | NOCAL | |
|  |  | LLI | L, FFF | ; FIRST IN FIND FLAG |
| 1AFB 36D3 |  |  |  | |
| 1AFD 3E01 |  | MVI | M, 01H | ; PRAISE FLAG |
| 1AFF 0602 |  | MVI | A, 2 | ; KILL MANUAL MODE |
| 1B01 55 |  | OUT | 0AH | |
| 1B02 A8 |  | XRA | A | |
| 1B03 55 |  | OUT | 0AH | |
|  |  | LLI | L, HIYL | ; SET HI LIMIT FIRST |
| 1B04 36C3 |  |  |  | |
| 1B06 466B14 |  | CALL | RDY | |
| 1B09 C1 |  | MOV | A, B | ; GET Y-HI |
| 1B0A 3C24 |  | CPI | 24H | |
| 1B0C 60651B |  | JC | CEl3 | ; JUMP IF NOT PAST 240 |
| 1B0F 3C37 |  | CPI | 37H | ; STARTING LOCATION MUST NOT BE |
| 1B11 40651B |  | JNC | CEL3 | ; ABOVE 369 |
| 1B14 F9 |  | MOV | M, B | ; STORE Y-HI AS UPPER LIMIT |
| 1B15 30 |  | INR | L | ; UPPER LIMIT OF LOW Y |
| 1B16 FA |  | MOV | M, C | ; Y-LO OF UPPER LIMIT |
| 1B17 C2 |  | MOV | A, C | ; GET Y-LO |
| 1B18 24F0 |  | ANI | 0F0H | ; REMOVE HEX PART OF ADDR |
| 1B1A 1480 |  | SUI | 80H | ; SUBTRACT 8 of 218 CENTER |
| 1B1C 40221B |  | JNC | CEL1 | ; JUMP IF UNITS OF PRESENT ADDR |
|  | ; | IS 8 OR 9 - NO BORROW | | |
| 1B1F 09 |  | DCR | B | ; SUBTRACT ONE FROM Y-HI |
| 1B20 1460 |  | SUI | 60H | ; CONVERT TO DECIMAL |
| 1B22 E0 | CEL1: | MOV | E, A | ; STORE LO ORDER DIFFERENCE IN E |
| 1B23 C1 |  | MOV | A, B | ; GET Y-HI OF UPPER LIMIT |
| 1B24 240F |  | ANI | 0FH | ; CHECK LSD FOR HEX FROM |
|  |  | A POSIBLE DECREMENT ABOVE | | |
| 1B26 3C0A |  | CPI | 0AH | ; GE. A = HEX |
| 1B28 C1 |  | MOV | A, B | ; GET Y-HI AGAIN |
| 1B29 602E1B |  | JC | $+5 | ; JUMP IF NO HEX FROM DRC |
| 1B2C 1406 |  | SUI | 06H | ; CONVERT TO DEC IF HEX |
| 1B2E 1421 |  | SUI | 21H | ; SUBTRACT 21 OF 218 CENTER |
| 1B30 C8 |  | MOV | B, A | ; STORE IN B |
| 1B31 240F |  | ANI | 0FH | ; CHECK FOR ANY HEX DIGITS |
| 1B33 3C0A |  | CPI | 0AH | ; GE. A = HEX |
| 1B35 C1 |  | MOV | A, B | ; RE-GET SUBTRACTED RESULT |
|  | ; | OF Y-HI - CENTER HI | | |
| 1B36 603B1B |  | JC | $+5 | ; JUMP IF NO HEX RESULT |
| 1B39 1406 |  | SUI | 06H | ; CONVERT TO DEC FROM HEX |
| 1B3B D8 |  | ,MOV | D, A | ; STORE DIFFER OF Y-HI |
|  |  | AND CENTER IN D | | |
| 1B3C 3C03 |  | CPI | 03H | ; CHECK FOR RANGE OF 30 UNITS |
|  | ; | ABOVE | ; GE. 248 | |
|  |  | CENTER | | |
| 1B3E 60651B |  | IC | CEL3 | ; JUMP IF BELOW 248 |
|  | ; | NOW CALC LOW LIMIT FROM DIFFERENCE | | |

TABLE C-continued

```
                        LLI     L,
                                LOYL+1
1B41 36C2
1B43 0680               MVI     A, 80H      ;SET A = CENTER-LO
1B45 94                 SUB     E           ;SUBTRACT LO-DIFFERENCE
1B46 F8                 MOV     M, A        ;MOVE TO MEMORY AS LOW LIMIT
1B47 40521B             JNC     CEL2        ;JUMP IF NO BORROW IN SUBTRACT
1B4A 1460               SUI     60H         ;CONVERT TO DEC IF BORROW
1B4C F8                 MOV     M, A        ;RE-STORE DEC LOW LIMIT
1B4D 0620               MVI     A, 20H      ;SET A TO CENTER-HI LESS 1
1B4F 44541B             JMP     $+5         ;FROM BORROW, JUMP
1B52 0621       CEL2    MVI     A, 21H      ;NO BORROW, SET A = Y CENTER
1B54 93                 SUB     D           ;SUBTRACT Y-HI DIFFERENCE IN D
1B55 08                 MOV     B, A        ;STORE DIFF IN B TEMP
1B56 240F               ANI     0FH         ;CHECK FOR HEX IN SUBTRACT
1B58 3007               CPI     07H         ;GE. 7 = BORROW
1B5A C1                 MOV     A, B        ;RE-GET SUBTRACTED DIFF
1B58 60601B             JC      $+5         ;JUMP IF NO BORROW
1B5E 1406               SUI     06H         ;CONVERT TO DECIMAL
1B60 31                 DCR     L           ;GET ADDR OF Y LIMIT MSD
1B61 F8                 MOV     M, B        ;STORE Y LOW LIMIT MSD
1B62 44851B             JMP     CEL4        ;SET Y MOTOR COMMANDS NOW
                CEL3    LLI     L, AFF
1B65 36B7
1B67 3E00               MVI     M, 0H
1B69 30                 INR     L
1B6A 3E00               MVI     M, 0H
1B6C 0640               MVI     A, 40H
1B6E 53                 OUT     09H
1B6F A8                 XRA     A
1B70 53                 OUT     09H
1B71 0608               MVI     A, 08H
1B73 55                 OUT     0AH
1B74 A8                 XRA     A
1B75 55                 OUT     0AH
1B76 061F               MVI     R, 1FH
1B78 468103             CALL    LAMPS
                        LLI     L, FFF
1B7B 36D3
1B7D 3E00               MVI     M, 0H
1B7F 460A02             CALL    EHORN
1B82 44D210             JMP     MANL
                ;       START OF MEANDER PATH
                CEL4:   LLI     L,          SET Y-MOTOR COMMAND FOR FAST NE
                                YCOM
1B85 36C5
1B87 3E04               MVI     M, 4
1B89 066D               MVI     A, 6DH      ;SET CELL FIND GALVO
1B8B 5D                 OUT     0EH
1B8C 468114             CALL    RDKY
1B8F 0622               MVI     A, 22H
                        LLI     L,          ;CHECK TO SEE IF IN DIFFERENTIAL
                                LMODE
1B91 360B
1B93 BF                 CMP     M           ;OF OPERATION
1B94 482B11             JNZ     KBSCR       ;NO,. GO TO MONITOR THE KEYBOARD
                ;       STARTING POINT FOR START OF MEANDER PATH OR IF
                ;       NO RESTRICTED ZONES CURRENTLY EXIST
1B97 0E01       CEL6:   MVI     B, 1        ;PRESET B-REG TO SELECT TASK 1 O
                        LLI     L,
                                FOCTR
1B99 36EC
1B9B 3E9C               MVI     M,          ;FOCUS EVERY 1248 MICRONS
                                9CH
                        LLI     L,          ;MEANDER PATH LIMIT CHECK
                                YCOM
1B9D 36C5
1B9F D7                 MOV     C, M
1BA0 C7                 MOV     A, M
1BA1 2401               ANI,    1           ;DETERMINE WHICH LIMIT SHOULD BE
1BA3 48AD1B             JNZ     CEL7
                        LLI     L,
                                LOYL
1BA6 36C1
1BA8 2600               MVI     E, 0        ;SET INDICATOR TO LOOK FOR LOW L
1BAA 44B11B             JMP     CEL8        ;0 = GOING DOWN
                CEL7:   LLI     L,
                                HIYL
1BAD 36C3
1BAF 2601               MVI     E, 1        ;SET INDICATOR TO LOOK FOR HIGH
1BB1 C2         CEL8:   MOV     R, C        ;1 = GOING UP
1BB2 59                 OUT     0CH         ;START Y-MOTOR MOVING
1BB3 4B         CEL9:   IN      5           ;READ GENERAL FLAG PORT
1BB4 2404               ANI     4
1BB6 68C51B             JZ      CEL9A
1BB9 47                 IN      3           ;KEYBOARD 2 FLAG HIGH
1BBA 2410               ANI     10H         ;CHECK MANUAL BIT
1BBC 68C51B             JZ      CEL9A
1BBF 0608               MVI     A, 8        ;MANUAL KEY WAS PRESSED
1BC1 59                 OUT     0CH         ;STOP Y-MOTOR
1BC2 44D210             JMP     MANL
1BC5 43         CEL9A:  IN      1
```

TABLE C-continued

```
1BC6 2480              ANI    80H     ;WAIT IF IN FLYBACK PART OF SWEE
1BC8 68B31B            JZ     CEL9
1BCB 4B      CEL10:    IN     5
1BCC 2410              ANI    10H     ;IF CELL FIND BIT IS HIGH, GO TO
1BCE 48801C            JNZ    CEL18   ;PICK UP DEFLECTION(S)
1BD1 43                IN     1
1BD2 2480              ANI    80H     ;IF STILL IN SCAN PART OF SWEEP,
1BD4 48CB1B            JNZ    CEL10   ;MONITORING CELL FIND BIT
             ;        IN FLYBACK PART OF SWEEP CHECK M.P. LIMITS
1BD7 C1                MOV    A, B    ;CHECK M.P.L. TASK INDICATOR
1BD8 3C02              CPI    2
1BDA 68F91B            JZ     CEL12
             ;        TASK 1 OF MEANDER PATH LIMIT CHECK (READ X, Y
                      CO
1BDD 064D    CEL11:    MVI    A, 4DH
1BDF 5D                OUT    0EH     ;CLEAR X, Y SEQUENCER
1BE0 066D              MVI    A, 6DH
1BE2 5D                OUT    0EH
1BE3 4B                IN     5
1BE4 2420              ANI    20H     ;WAIT IF X, Y READY BIT IS LOW
1BE6 68DD1B            JZ     CEL11
1BE9 49                IN     4
1BEA 49                IN     4
1BEB 49                IN     4
1BEC D0                MOV    C, A    ;PICK UP Y-HIGH
1BED 49                IN     4
1BEE D8                MOV    D, A    ;PICK UP Y-LOW
1BEF 4B                IN     5
1BF0 2420              ANI    20H
1BF2 68DD1B            JZ     CEL11   ;IF CHANGE OF STATE OCCURRED, RE
1BF5 08                INR    B
1BF6 44B21B            JMP    CEL9
             ;        TASK 2 OF MEANDER PATH LIMIT CHECK
1BF9 C6      CEL12:    MOV    A, L
                       LLI    L,
                              ASAVE
1BFA 36E9
1BFC F8                MOV    M, A
                       LLI    L,FOCTR
1BFD 36EC
1BFF C7                MOV    A, M
1C00 1401              SUI    01H
1C02 3C00              CPI    00H
1C04 680F1C            JZ     TIMFO
1C07 FB                MOV    M, A
             BG1:      LLI    L,
                              ASAVE
1C08 36E9
1C0A C7                MOV    A, M
1C0B F0                MOV    L, A
1C0C 44251C            JMP    CL12A
             TIMFO:    LLI    L, AFF
1C0F 36B7
1C11 C7                MOV    A, M
1C12 3C00              CPI    00H
1C14 68081C            JZ     BG1
1C17 0608              MVI    A, 08H
1C19 59                OUT    0CH
1C1A 1EFB              MVI    D,
                              0FBH
1C1C 460F07            CALL   TIMR
1C1F 466D1E            CALL   FOCUS
1C22 44971B            JMP    CEL6
1C25 09      CL12A:    DCR    B
1C26 A8                XRA    A
1C27 BC                CMP    E       ;DETERMINE DIRECTION OF Y-MOTOR
1C28 48401C            JNZ    CEL14
1C2B C7                MOV    A, M    ;GOING DOWN THE SLIDE
1C2C BA                CMP    C
1C2D 68361C            JZ     CEL13   ;MSB EQUAL, CHECK LSB
1C30 60B31B            JC     CEL9    ;NOT AT LIMIT YET, GO TO LOOK FO
1C33 44521C            JMP    CEL16   ;AT LIMIT, GO TO REVERSE DIRECTI
1C36 30      CEL13:    INR    L
1C37 C7                MOV    A, M
1C38 31                DCR    L
1C39 BB                CMP    D
1C3A 60B31B            JC     CEL9    ;NOT AT LIMIT YET, GO TO LOOK FO
1C3D 44521C            JMP    CEL16   ;AT LIMIT, GO TO REVERSE DIRECTI
1C40 C7      CEL14:    MOV    A, M    ;GOING UP THE SLIDE
1C41 BA                CMP    C
1C42 684B1C            JZ     CEL15   ;MSB EQUAL, CHECK LSB
1C45 40B31B            JNC    CEL9    ;NOT AT LIMIT, GO LOOK FOR CELLS
1C48 44521C            JMP    CEL16   ;AT LIMIT, GO TO REVERSE DIRECTI
1C4B 30      CEL15:    INR    L
1C4C C7                MOV    A, M
1C4D 31                DCR    L
1C4E BB                CMP    D
1C4F 40B31B            JNC    CEL9    ;NOT AT LIMIT YET, GO TO LOOK FO
             ;        VERTICAL LIMIT DETECTED, TIME TO CHANGE
                      Y-DIREC
1C52 0608    CEL16:    MVI    A, 8
1C54 59                OUT    0CH     ;STOP THE Y-MOTOR
```

TABLE C-continued

| | | | | |
|---|---|---|---|---|
| 1C55 1EFD | | MVI | D, 0FDH | |
| 1C57 460F07 | | CALL | TIMR | ;SHORT TIME DELAY |
| 1C5A 0607 | | MVI | A, 7 | |
| 1C5C 59 | | OUT | 0CH | ;MOVE THE STAGE OVER IN THE +X-D |
| 1C5D 162B | | MVI | C, 43 | |
| 1C5F 464E07 | CEL17: | CALL | WTXY | ;COUNT THE NUMBER OF ENCODER PUL |
| 1C62 11 | | DCR | C | |
| 1C63 485F1C | | JNZ | CEL17 | |
| 1C66 0608 | | MVI | A, 8 | |
| 1C68 59 | | OUT | 0CH | ;STOP THE X-MOTOR |
| 1C69 1EFB | | MVI | D,0FBH | |
| 1C6B 460F07 | | CALL | TIMR | ;SHORT TIME DELAY |
| 1C6E 468114 | | CALL | RDXY | ;READ AND STORE LMP |
| 1C71 468507 | | CALL | XRDC | ;DISPLAY X-COORDINATE |
| 1C74 46AC07 | | CALL | YACL | ;DISPLAY Y-COORDINATE |
| | | LLI | L, YCOM | ;CHANGE THE Y-MOTOR COMMAND |
| 1C77 36C5 | | | | |
| 1C79 0609 | | MVI | A, 9 | |
| 1C7B 97 | | SUB | M | |
| 1C7C FB | | MOV | M, A | |
| 1C7D 44971B | | JMP | CEL6 | ;GO TO LOOK FOR MORE CELLS |
| | ; | DETECTION OF CELL <5> HAS OCCURRED | | |
| 1C80 4F | CEL18: | IN | 7 | ;READ 1ST DEFLECTION UNIT <0-180 |
| | | LLI | L, QUE+2 | |
| 1C81 36DE | | | | |
| 1C83 F8 | | MOV | M, A | |
| 1C84 0E01 | | MVI | B, 1 | |
| 1C86 0602 | | MVI | A, 02H | |
| 1C88 5B | | OUT | 0DH | |
| 1C89 A8 | | XRA | A | |
| 1C8A 5B | | OUT | 0DH | |
| | | LLI | L, T2FLG | |
| 1C8B 36E7 | | | | |
| 1C8D 3E00 | | MVI | M, 00H | |
| | | LLI | L, QUE+2 | |
| 1C8F 36DE | | | | |
| 1C91 43 | CEL19: | IN | 1 | |
| 1C92 2480 | | ANI | B0H | ;WAIT FOR SCAN TO FINISH |
| 1C94 48911C | | JNZ | CEL19 | |
| 1C97 4B | | IN | 5 | ;LOOK AT CELL FIND BIT |
| 1C98 2410 | | ANI | 10H | |
| 1C9A 68B11C | | JZ | CEL24 | |
| 1C9D 4F | | IN | 7 | ;CELL FOUND, FETCH DEFLECTION UN |
| 1C9E 30 | | INR | L | |
| 1C9F F8 | | MOV | M, A | |
| 1CA0 88 | | INR | B | |
| 1CA1 43 | | IN | 1 | |
| 1CA2 2480 | | ANI | B0H | ;WAIT FOR STOPPED SCAN TO FINI |
| 1CA4 48B11C | | JNZ | CEL24 | |
| 1CA7 4B | | IN | 5 | |
| 1CA8 2410 | | ANI | 10H | ;CHECK CELL FIND READY BIT |
| 1CAA 68B11C | | JZ | CEL24 | |
| 1CAD 4F | | IN | 7 | ;CELL FOUND <0-180> |
| 1CAE 30 | | INR | L | |
| 1CAF F8 | | MOV | M, A | |
| 1CB0 08 | | INR | B | |
| | ; | CELL INFORMATION FLAGS ARE SET | | |
| 1CB1 0608 | CEL24: | MVI | A, 08H | |
| 1CB3 59 | | OUT | 0CH | |
| | | LLI | L, QUE | |
| 1CB4 36DC | | | | |
| 1CB6 F9 | | MOV | M, B | ;SAVE NUMBER OF CELLS FOUND IN |
| | | LLI | L, REMAN | ;LOCATIONS QUE AND REMAN |
| 1CB7 36DB | | | | |
| 1CB9 F9 | | MOV | M, B | |
| 1CBA 464D00 | | CALL | ADJUST | ;ADJUST CELL FIND A/D READINGS |
| 1CBD 1EFD | | MVI | D, 0FDH | |
| 1CBF 460F07 | | CALL | TIMR | ;Y-MOTOR IS STOPPED |
| | | LLI | L, LMP+2 | |
| 1CC2 36C8 | | | | |
| 1CC4 466B14 | | CALL | RDY | |
| 1CC7 F9 | | MOV | M, B | |
| 1CC8 30 | | INR | L | |
| 1CC9 FA | | MOV | M, C | |
| | ; | CENTER ON NEWLY FOUND CELLS | | |
| | | LLI | L, QUE+2 | |
| 1CCA 36DE | | | | |
| 1CCC C7 | | MOV | A, M | |
| | CEL25: | LLI | L, DEFLT | ;CLEAR THE NO. OF ENCODER PULSES |
| 1CCD 36D7 | | | | |
| 1CCF 3E00 | | MVI | M, 0 | ;CELL IS FROM THE CENTER OF THE |

TABLE C-continued

| | | | | |
|---|---|---|---|---|
| 1CD1 3C2D | | CPI | 45 | ;CHECK WHICH SIDE OF CENTER THE |
| 1CD3 48E81C | | JNC | CL25A | |
| | ; | THE CELL IS ON THE RIGHT SIDE OF THE T-V MONITO | | |
| 1CD6 2CFF | | XRI | 0FFH | COMPUTE THE NUMBER OF ENCODER P |
| 1CD8 14D2 | | SUI | 218 | ;THE CELL IS TO THE RIGHT OF CEN |
| 1CDA 24FE | | ANI | 0FEH | |
| 1CDC 68A81D | | JZ | CEL28 | ;IF AT CENTER, SKIP CENTERING |
| 1CDF 0A | | RRC | | |
| 1CE0 F8 | | MOV | M, A | |
| 1CE1 D0 | | MOV | C, A | |
| 1CE2 30 | | INR | L | |
| 1CE3 3E07 | | MVI | M, 7 | ;SET THE RETURN X-MOTOR COMMAND |
| 1CE5 44F51C | | JMP | CEL26 | |
| | ; | THE CELL IS ON THE LEFT SIDE OF THE T-V MONITOR | | |
| 1CE8 142C | CL25A: | SUI | 41 | ;COMPUTE THE NUMBER OF ENCODER P |
| 1CEA 24FE | | ANI | 0FEH | ;THE CELL IS TO THE LEFT OF CENT |
| 1CEC 68081D | | JZ | CEL28 | ;IF AT CENTER, SKIP CENTERING |
| 1CEF 8A | | RRC | | |
| 1CF0 FB | | MOV | M, A | |
| 1CF1 D0 | | MOV | C, A | |
| 1CF2 30 | | INR | L | |
| 1CF3 3E06 | | MVI | M, 6 | ;SET THE RETURN X-MOTOR COMMAND |
| | ; | DRIVE TO CENTER THE CELL | | |
| 1CF5 060D | CEL26: | MVI | A, 13 | |
| 1CF7 97 | | SUB | M | ;DETERMINE X-MOTOR COMMAND |
| 1CF8 59 | | OUT | 0CH | ;DRIVE TO THE CELL |
| 1CF9 464E07 | CEL27: | CALL | WTXY | |
| 1CFC 11 | | DCR | C | |
| 1CFD 48F91C | | JNZ | CEL27 | |
| 1D00 0608 | | MVI | A, 8 | ;STOP THE X-MOTOR WHEN AT THE CE |
| 1D02 59 | | OUT | 0CH | |
| 1D03 1EFB | | MVI | D, 0FBH | |
| 1D05 460F07 | | CALL | TIMR | ;SHORT TIME DELAY |
| 1D08 468507 | CEL28: | CALL | XADC | |
| 1D0B 46H007 | | CALL | YACL | |
| 1D0E 45 | | IN | 2 | |
| 1D0F 47 | | IN | 3 | |
| | | LLI | L, AFF | |
| 1D10 36B7 | | | | |
| 1D12 07 | | MOV | A, M | |
| 1D13 3C01 | | CPI | 1 | |
| 1D15 6A6D1E | | CZ | FOCUS | ;FOCUS IF AUTO FOCUS FLAG SET |
| 1D18 43 | | IN | 01H | |
| 1D19 2440 | | ANI | 40H | |
| 1D18 484A1D | | JNZ | CL2BB | |
| 1D1E 1604 | | MVI | C, 04 | |
| 1D20 060D | | MVI | A, 0DH | |
| 1D22 59 | | OUT | 0CH | |
| 1D23 464E07 | | CALL | WTXY | |
| 1D26 11 | | DCR | C | |
| 1D27 48231D | | JNZ | CL2BA-12 | |
| 1D2A 1608 | | MVI | C, 0CH | |
| 1D2C 060C | | MVI | A, 0CH | |
| 1D2E 59 | | OUT | 0CH | |
| 1D2F 464E07 | CL28A: | CALL | WTXY | |
| 1D32 11 | | DCR | C | |
| 1D33 482F1D | | JNZ | CL28A | |
| 1D36 1604 | | MVI | C, 04 | |
| 1D38 060D | | MVI | A, 0DH | |
| 1D3A 59 | | OUT | 0CH | |
| 1D3B 464E07 | | CALL | WTXY | |
| 1D3E 11 | | DCR | C | |
| 1D3F 483B1D | | JNZ | CL28A+12 | |
| 1D42 0608 | | MVI | A, 0CH | |
| 1D44 59 | | OUT | 0CH | |
| 1D45 1EF0 | | MVI | D, 0F0H | |
| 1D47 460F07 | | CALL | TIMR | |
| 1D4A 43 | CL28B: | IN | 01H | |
| 1D4B 2440 | | ANI | 40H | |
| 1D4D 482B11 | | JNZ | KBSCR | |
| | | LLI | L, T2FLG | |
| 1D50 36E7 | | | | |
| 1D52 3E01 | | MVI | M, 01H | |
| 1D54 442B11 | | JMP | KBSCR | ;GO TO HAVE CELL IDENTIFIED |
| | ; | CELL FIND ROUTINE PART 2 (USED WHEN ONE OR | | |
| | ; | MORE RESTRICTED ZONES CURRENTLY EXIST, | | |
| | ; | Y-MOTOR IS BEING DRIVEN AT THE SLOW SPEED.) | | |
| 1D57 0E0C | CEL29: | MVI | B, 12 | |
| 1D59 43 | CEL30: | IN | 1 | ;WAIT FOR SWEEP FLYBACK |
| 1D5A 2480 | | ANI | 80H | |

TABLE C-continued

```
1D5C 48591D            JNZ    CEL30
                       LLI    L,       ;ISSUE SLOW Y-MOTOR COMMAND
                              YCOM
1D5F 36C5
1D61 C7                MOV    A, M
1D62 59                OUT    0CH
                       LLI    L, QUE
1D63 36DC
1D65 4B       CEL31:   IN     5        ;READ GENERAL FLAG PORT
1D66 2404              ANI    4
1D68 68771D            JZ     CL31A
1D6B 47                IN     3        ;KEYBOARD 2 FLAG HIGH
1D6C 2410              ANI    10H      ;CHECK MANUAL BIT
1D6E 68771D            JZ     CL31A
1D71 0608              MVI    A, 8     ;MANUAL KEY WAS PRESSED
1D73 59                OUT    0CH      ;STOP THE Y-MOTOR
1D74 44D210            JMP    MANL
1D77 43       CL31A:   IN     1        ;WAIT FOR SWEEP SCAN
1D78 2488              ANI    80H
1D7A 68651D            JZ     CEL31
1D7D 4B       CEL32:   IN     5        ;MONITOR CELL FIND BIT
1D7E 2410              ANI    10H
1D80 48A31D            JNZ    CEL33    ;IF HIGH, GO TO PICK UP CELLS(S)
1D83 43                IN     1
1D84 2480              ANI    80H
1D86 487D1D            JNZ    CEL32    ;KEEP MONITORING IF IN SCAN
1D89 89                DCR    B
1D8A 48651D            JNZ    CEL31
              ;        NO MORE RESTRICTED ZONES EXIST, RESUME
              ;        FAST Y-MOTOR SPEED
1D8D 0E04              MVI    B, 4
                       LLI    L,
                              YCOM
1D8F 36C5
1D91 C7                MOV    A, M
1D92 2401              ANI    1
1D94 81                ADD    B        ;DETERMINE Y-DIRECTION AND SWITC
1D95 F8                MOV    M, A     ;Y-MOTOR SPEED FROM SLOW TO FAST
1D96 D0                MOV    C, A
                       LLI    L,       ;RE-INITIALIZE ZONE BOUNDARIES
                              LSIDE
1D97 36E1
1D99 0678              MVI    A, 120
1D9B F8                MOV    M, A
1D9C 30                INR    L
1D9D F8                MOV    M, A
1D9E 30                INR    L
1D9F F8                MOV    M, A
1DA8 44971B            JMF    CEL6     ;GO TO LOOK FOR MORE CELLS
              ;        CELL FIND READY BIT WENT HIGH
1DA3 3E01     CEL33:   MVI    M, 1
1DA5 30                INR    L
1DA6 30                INR    L
1DA7 4F                IN     7        ;SAVE 1ST DEFLECTION UNIT <0-180
1DA8 F8                MOV    M, A
1DA9 1601              MVI    C, 1
1DAB 0602              MVI    A, 02H
1DAD 58                OUT    0DH
1DAE A8                XRA    A
1DAF 58                OUT    0DH
                       LLI    L,
                              T2FLG
1DB0 36E7
1DB2 3E80              MVI    M,
                              00H
                       LLI    L,
                              QUE+2
1DB4 36DE
1DB6 43       CEL34:   IN     1
1DB7 2480              ANI    C0H      ;WAIT FOR SCAN TO FINISH
1DB9 48861D            JNZ    CEL34
1DBC 0E02              MVI    B, 2
1DBE 4B       CEL35:   IN     5        ;CHECK FOR ANY MORE CELLS
1DBF 2410              ANI    10H
1DC1 68CC1D            JZ     CEL36
1DC4 4F                IN     7        ;CELL FOUND, FETCH DEFLECTION UN
1DC5 30                INR    L
1DC6 10                INR    C
1DC7 F8                MOV    M, A
1DC8 09                DCR    B
1DC9 48BE1D            JNZ    CEL35
              ;        COMPARE JUST FOUND CELL (S) AGAINST
              ;        RESTRICTED Z
              CEL36:   LLI    L,       SAVE NUMBER OF CELLS DETECTED P
                              REMAN
1DCC 36DB
1DCE FA                MOV    M, C
                       LLI    L, QUE   ;SAVE NUMBER OF CELLS DETECTED
1DCF 36DC
1DD1 FA                MOV    M, C
1DD2 CA                MOV    B, C
1DD3 464D00            CALL   ADJUST   ;ADJUST CELL FIND A/D READINGS
1DD6 1E00              MVI    D, 0
```

TABLE C-continued

|  |  |  |  |  |
|---|---|---|---|---|
|  | CEL37: | LLI | L, QUE+1 |  |
| 1DDB 36DD |  |  |  |  |
| 1DDA C6 |  | MOV | A, L |  |
| 1DDB 82 |  | ADD | C |  |
| 1DDC F0 |  | MOV | L, A |  |
| 1DDD E0 |  | MOV | E, A |  |
| 1DDE C7 |  | MOV | A, M | ;NEW DEFLECTION VALUE |
| 1DDF CF |  | MOV | B, M |  |
|  |  | LLI | L, LSIDE |  |
| 1DE0 36E1 |  |  |  |  |
| 1DE2 97 |  | SUB | M |  |
| 1DE3 3C14 |  | CPI | 20 | ;ZONE FOR 0–90 VALUES |
| 1DE5 60131E |  | JC | CEL41 | ;INVALID NEW CELL FOUND |
| 1DE8 30 |  | INR | L |  |
| 1DE9 C1 |  | MOV | A, B |  |
| 1DEA 97 |  | SUB | M |  |
| 1DEB 3C14 |  | CPI | 20 | ;ZONE FOR 0–90 VALUES |
| 1DED 60131E |  | JC | CEL41 | ;INVALID NEW CELL FOUND |
| 1DF0 30 |  | INR | L |  |
| 1DF1 C1 |  | MOV | A, B |  |
| 1DF2 97 |  | SUB | M |  |
| 1DF3 3014 |  | CPI | 20 | ;ZONE FOR 0–90 VALUES |
| 1DF5 60131E |  | JC | CEL41 | ;INVALID NEW CELL FOUND |
|  | ; | VALID NEW CELL FOUND |  |  |
| 1DF8 0608 |  | MVI | A, 8 |  |
| 1DFA 59 |  | OUT | 0CH | ;STOP THE Y-MOTOR |
| 1DFB 1E01 |  | MVI | D, 1 | ;SET FOUND CELL INDICATOR |
| 1DFD 11 |  | DCR | C |  |
| 1DFE 48D81D |  | JNZ | CEL37 |  |
| 1E01 1EFD | CEL38: | MVI | D, 0FDH |  |
| 1E03 460F07 |  | CALL | TIMR |  |
|  | CEL39: | LLI | L, LMP+2 |  |
| 1E06 36C8 |  |  |  |  |
| 1E08 466B14 |  | CALL | RDY |  |
| 1E0B F9 |  | MOV | M, B |  |
| 1E0C 30 |  | INR | L |  |
| 1E0D FA |  | MOV | M, C |  |
|  |  | LLI | L, QUE+2 |  |
| 1E0E 36DE |  |  |  |  |
| 1E10 44F819 |  | JMP | ENHER |  |
|  | ; | FLAG INVALID CELL TO PREVENT CENTERING ON IT |  |  |
| 1E13 C1 | CEL41: | MOV | A, 8 |  |
| 1E14 048B |  | ADI | 80H |  |
| 1E16 F4 |  | MOV | L, E |  |
| 1E17 F8 |  | MOV | M, A |  |
| 1E18 11 |  | DCR | C |  |
| 1E19 48D81D |  | JNZ | CEL37 |  |
| 1E1C A8 |  | XRA | A |  |
| 1E1D BB |  | CMP | D |  |
| 1E1E 48011E |  | JNZ | CEL38 | ;IF VALID CELL PREVIOUSLY FOUND, |
| 1E21 464E07 |  | CALL | WTXY |  |
| 1E24 44061E |  | JMP | CEL39 |  |

TABLE D

;ROUTINE TO RETURN TO LAST MEANDER PATH
;

|  |  |  |  |
|---|---|---|---|
|  | RMPI: | LLI | L, LMP |
| 1E27 36C6 |  |  |  |
| 1E29 DF |  | MOV | D, M |
| 1E2A 30 |  | INR | L |
| 1E2B E7 |  | MOV | E, M |
| 1E2C 465514 |  | CALL | RDX |
| 1E2F 46DC01 |  | CALL | DIRFX |
| 1E32 3C08 |  | CPI | 08H |
| 1E34 2B |  | RZ |  |
|  |  | LLI | L, ENCTR |
| 1E35 36EB |  |  |  |
| 1E37 3E04 |  | MVI | M, 04 |
| 1E39 59 |  | OUT | 0CH |
| 1E3A 465515 | RRI: | CALL | RDX |
| 1E3D C1 |  | MOV | A, B |
| 1E3E BB |  | CMP | D |
| 1E3F 48521E |  | JNZ | AG1 |
| 1E42 C2 |  | MOV | A, C |
| 1E43 BC |  | CMP | E |
| 1E44 48521E |  | JNZ | AG1 |
| 1E47 0608 |  | MVI | A, 08H |
| 1E49 59 |  | OUT | 0CH |
| 1E4A 1EFB |  | MVI | D, 0FBH |
| 1E4C 1678 |  | MVI | C, 120 |
| 1E4E 460F07 |  | CALL | TIMR |
| 1E51 07 |  | RET |  |
| 1E52 36EB | AG1: | LLI | L, ENCTR |
| 1E54 C7 |  | MOV | A, M |
| 1E55 1401 |  | SUI | 01H |
| 1E57 3C00 |  | CPI | 00H |
| 1E59 68601E |  | JZ | AG2 |
| 1E5C F8 |  | MOV | M, A |
| 1E5D 443A1E |  | JMP | RR1 |
| 1E60 0608 | AG2: | MVI | A, 08H |
| 1E62 59 |  | OUT | 0CH |
| 1E63 1EFB |  | MVI | D, 0FBH |
| 1E65 1678 |  | MVI | C, 120 |
| 1E67 460F07 |  | CALL | TIMR |
| 1E6A 44271E |  | JMP | RMPI |

TABLE E

```
                        ; FAIL SAFE AUTOMATIC FOCUS ROUTINE
1E6D 0665    FOCUS:  MVI    A, 65H
1E6F 5D              OUT    DEH        ;ENABLE AUTO FOCUS GALVO
1E70 0602            MVI    A, 2
1E72 59              OUT    0CH        ;DRIVE Z-MOTOR FAST NEGATIVE <-Z
1E73 2622            MVI    E, 34
1E75 46D91E  FOC1:   CALL   PULSE      ;WAIT FOR 25 Z-ENCODER PULSES <2
1E78 21              DCR    E
1E79 48751E          JNZ    FOC1
1E7C 060B            MVI    A, 0BH     ;REVERSE Z-DIRECTION
1E7E 59              OUT    0CH        ;DRIVE Z-MOTOR SLOW POSITIVE <+Z
1E7F 0E00            MVI    B, O       ;CLEAR PEAK FOCUS A/D VALUE
1E81 1E00            MVI    D, O       ;CLEAR PEAK LOCATION INDICATOR
                   ; SET SHEEP RANGE FOR 50 Z-ENCODER PULSES <4 MICE
1E83 2644            MVI    E, 68
1E85 4B      FOC2:   IN     5          ;PICK UP AUTO FOCUS AND Z-ENCODE
1E86 2450            ANI    50H
1E88 3C50            CPI    50H
1E8A 689E1E          JZ     FOC3       ;AUTO FOCUS PRESENT
1E8D 3C0A            CPI    10
1E8F 68A81E          JZ     F0C4       ;AUTO FOCUS AND Z-ENCODER
                                         PRESEN
1E92 3C40            CPI    40H
1E94 68851E          JZ     FOC2       ;BOTH SIGNALS ABSENT
                   ; ONLY Z-ENCODER SIGNAL READY
1E97 21              DCR    E          ;ADJUST LOCATION INDICATOR
1E98 68851E          JZ     FOC6       ;LEAVE WHEN SHEEP FINISHED
1E98 44851E          JMP    FOC2
                   ; ONLY AUTO FOCUS SIGNAL READY
1E9E 4F      FOC3:   IN     7          ;PICK UP NEW FOCUS A/D VALUE
1E9F B9              CMP    B          ;AND COMPARE WITH CURRENT PEAK
1EA0 60851E          JC     FOC2
1EA3 CB              MOV    B, A       ;BETTER PEAK FOUND
1EA4 DC              MOV    D, E
1EA5 44851E          JMP    FOC2
                   ; BOTH AUTO FOCUS AND Z-ENCODER SIGNALS READY
1EA8 21      F0C4:   DCR    E          ;ADJUST LOCATION INDICATOR
1EA9 4F              IN     7          ;PICK UP NEW FOCUS A/D VALUE
1EAA 89              CMP    B          ;AND COMPARE TO CURRENT PEAK
1EAB 60B01E          JC     FOC5
1EAE C8              MOV    B, A       ;BETTER PEAK FOUND
1EAF DC              MOV    D, E
1EB0 20      FOC5:   INR    E
1EB1 21              DCR    E
1EB2 48851E          JNZ    FOC2       ;NOT FINISHED YET
                   ; SWEEP FINISHED, RETURN TO NEWLY FOUND PEAK, OR
                   ; LAST GOOD FOCUS POSITION IF NECESSARY
1EB5 0608    FOC6:   MVI    A, 8
1EB7 59              OUT    0CH        ;STOP Z-MOTOR
1EB8 060D            MVI    A, 13      ;CHECK FOR TOO LOW PEAK
1EBA 89              CMP    B
1EBB 60C01E          JC     FOC7
1EBE 1E22            MVI    D, 34
1EC0 06FD    FOC7:   MVI    A, 253     ;CHECK FOR SATURATED PEAK
1EC2 B9              CMP    B
1EC3 40C81E          JNC    F0C8
1EC6 1E22            MVI    D, 34
                   ; RETURN TO DESIRED FOCUS LOCATION
1EC8 0602    FOC8:   MVI    A, 2
1ECA 59              OUT    0CH        ;DRIVE Z-MOTOR FAST NEGATIVE <-Z
1ECB 46D91E  FOC9:   CALL   PULSE
1ECE 19              DCR    D
1ECF 48CB1E          JNZ    FOC9
                   ; AT PEAK, STOP ALL ACTION
1ED2 0608            MVI    A, 8
1ED4 59              OUT    0CH        ;STOP Z-MOTOR
1ED5 066D            MVI    A, 6DH
1ED7 5D              OUT    0EH        ;ENABLE CELL FIND GALVO
1ED8 07              RET
                   ; ROUTINE TO SYNC ON Z-ENCODER PULSES
1ED9 36FF    PULSE:  MVI    L, 255     ;FAIL SAFE COUNTER
1EDB 4B      PUL1:   IN     5
1EDC 2440            ANI    40H
1EDE 68EB1E          JZ     PUL3       ;WAIT IF PULSE HIGH
1EE1 31              DCR    L
1EE2 48DB1E          JNZ    PUL1
                   ; NO Z-ENCODER PULSE, RETURN TO MANUAL MODE OF OP
1EE5 066D    PUL2:   MVI    A, 6DH
1EE7 5D              OUT    0EH        ;ENABLE CELL FIND GALVO
1EE8 44D210          JMP    MANL
1EEB 36FF    PUL3:   MVI    L, 255     ;FAIL SAFE COUNTER
1EED 4B              IN     5
1EEE 2440            ANI    40H
1EF0 0B              RNZ               ;WAIT IF PULSE LOW
1EF1 31              DCR    L
1EF2 48ED1E          JNZ    PUL3+2
1EF5 44E51E          JMP    PUL2       ;NO ENCODER PULSE FOUND
                     END
```

The embodiments of the invention in which an exclusive property or right is claimed are defined as follows:

1. An automatic cell-find and automatic focus system for use in a scanning microscope which includes both an objective lens and an adjustable stage means, said system operating at alternate times in a cell-find mode and in an automatic focus mode, the system comprising:

slide supporting stage means adjustable in the x, y, and z axis;

light source means providing a light beam through said stage means and said objective lens to beam utilizing means;

light responsive means providing an electrical output level which is a function of the light falling thereon;

optical scanning means comprising an oscillating mirror, said mirror oscillating in the x axis and intercepting at least a part of the light beam, to repetitively scan across the scene of the microscope slide in the x direction, and directing the intercepted light beam on to said light responsive means, and scanning means being operative during both of said modes;

means driving said scanning means at a slower speed during the automatic focus mode than during cell-find mode;

stage traverse control means connected to said stage means to cause said stage means to traverse along a predetermined meander path in the y axis while in cell-find mode until an area of desired optical density appears in view, said traverse control means being further connected to and controlled by said light responsive means to interrupt stage traverse upon appearance of the area of desired optical density in said scan;

means including switching means responsive to the appearance of the area of desired optical intensity in the scanned view for switching said system for the cell-find mode to the automatic focus mode, said y traverse being stopped during automatic focus mode;

focus control means for adjusting the position of said stage in the z axis after appearance of a desired area to provide proper focusing comprising, means sequentially activating said focus control means, after interruption of said traverse, for the period of time required to accomplish focus, z axis actuator means connected to said slide supporting stage means for adjusting said stage means in the z axis direction, control means causing said actuator means to adjust the position of said stage means in a predetermined sequence during focus mode so that said position is changing while the plurality of scans is simultaneously occuring, light intensity to electrical signal level transducer means including said light responsive means, to provide an output signal with each of said plurality of scans, and comparator-controller means connected to receive and compare the magnitude of each output signal from said transducer means with the signal magnitude of the highest previous scan, to select the highest magnitude signal of said plurality of scans and instruct said focus control means so that said actuator means returns said stage means to the z position of highest signal representing optimum focus.

2. The invention according to claim 1 in which said predetermined sequence of stage adjust during auto-focus further comprises:

said control means first causing the z axis actuator means to drive the stage slightly away from the previous optimum focus position, then to drive the stage back to and through the previous optimum focus position while the scanner provides repetitive auto-focus scans to determine a new optimum focus, means recording the signal indicative of focus from each of the successive scans, the maximum amplitude signal indicating the new optimum focus position being kept, said control means in response to the maximum amplitude signal, then causing the z axis actuator means to move to the new optimum focus position.

3. The invention according to claim 1 in which said light intensity to electrical signal level transducer means is a light intensity rate of change to electrical signal level transducer means and is responsive only to light intensity rate of change to provide an output signal, the magnitude of which signal is a function of the rate of change in light intensity received by said light responsive means.

4. The invention according to claim 3 in which said light intensity rate of change to voltage transducer means further includes, differentiating means responsive to each rate of change in the level of electrical output, the differentiating means providing output pulses the magnitudes of which are a function of the light intensity rate of change during a scan.

5. The incention according to claim 4 in which said light intensity rate of change to voltage transducer means further includes integrating means connected to said differentiating means output to receive and integrate the differentiated pulses of each auto-focus scan.

6. The invention according to claim 5 in which said light intensity rate of change to voltage transducer means further includes integrator reset means for resetting said integrating means before commencing each auto-focus scan.

7. The invention according to claim 1 in which said light responsive means comprises a first and a second light responsive element, the first light responsive element being connected to said stage traverse control means and the second light responsive element being included in said light intensity rate of change to voltage transducer means.

8. The invention according to claim 7 in which said light responsive elements are silicon photodetectors.

9. The invention according to claim 1 in which said area of desired optical density is a leukocyte.

10. The invention according to claim 1 in which said comparator-controller means is a microprocessor.

11. In a scanning automated microscope system, a process of centering a leukocyte in the optics comprising the steps of:

a. reading the location of the leukocyte along the scan line and converting the read value to a digital number;

b. storing the digital number location in the memory;

c. subtracting $x/2$ from the digital number, where numbers across the scan increase from $0$ to $x$ and $x/2$ represents mid-position, the subtracted remainder being positive (+), negative (−), or zero (0) depending upon the magnitude of the number relative to $x/2$, and d. driving the motor a distance equal to the number of counts of the remainder and in the direction indicated by the scan of the remainder.

12. An automatic cell-find and automatic focus system for use in scanning microscope which includes both an objective lens and an adjustable stage means, said system operating at alternate times in a cell-find mode and in an automatic focus mode, the system comprising:

slide supporting stage means adjustable in the $x$, $y$, and $z$ axis by $x$, $y$, and $z$ motors;

light source means providing a light beam through said stage means and said objective lens to beam utilizing means;

an optical scanner intercepting a part of the light beam and directing it into light responsive means, said scanner comprising a mirror adapted to be oscillated in the $x$ direction scanning across the scene of a microscope slide to scan for information for cell-find and for focus;

mirror position sensing means connected with said optical scanner for providing an electrical signal output representative of mirror position;

first light responsive means receiving the light beam from said mirror and providing a first electrical output signal representative of light received, said electrical signal having a rate of change component which results from abrupt light intensity variation during a sweep such as crossing cell edges;

electrical means connected to receive the first electrical signal from said light responsive means, said electrical means being responsive only to said rate of change component in said electrical signal, said electrical means providing each sweep an electrical focus signal the magnitude of which increases as the light intensity rate of change component increases;

analog to digital converter means; said converter means having a signal input terminal and having a strobe terminal for actuating said converter to accept the analog information at said converter to accept the analog information at said signal input terminal upon the occurrence of a strobe pulse;

mode switchover means connecting said mirror position signal to said converter means signal input terminal during cell-find mode and connecting said focus signal to said signal input terminal during auto-focus mode;

means causing said $x$ and $y$ motors to drive said stage in a predetermined meander path during cell-find mode;

second light responsive means receiving the light beam from said mirror and providing a second electrical output signal the level of which is representative of light intensity received;

signal level comparator means receiving said second electrical output signal and providing an output pulse when said sweep crosses an area of desired optical density such as a leukocyte;

means for applying a strobe pulse to said converter means during cell-find mode scanning upon the occurrence of a leukocyte produced pulse so that the mirror position and thereby the leukocyte $x$ coordinate position long the sweep is recorded;

means for applying a strobe pulse to said converter means during auto-focus mode at the end of sawtooth sweep so that the signal indicative of focus can be obtained with each sweep; and control means active during auto-focus mode first causing the $z$ motor to drive the stage slightly away from the previous optimum focus position, then to drive the stage back to and through the previous optimum focus position and slightly beyond while the scanner provides repetitive auto-focus sweeps to determine a new optimum focus, means recording and comparing the signal indicative of focus from each of the successive sweeps, keeping the maximum amplitude signal of the compared signals indicating the new optimum focus position, said $z$ motor control means in response to the selected signal, then causing the $z$ motor to move to the new optimum focus position.

13. The invention according to claim 12 and further comprising:

sine wave generator means;

sawtooth wave generator means; and said mode switchover means connecting said sine wave generator means to energize said optical scanner to sweep said mirror in a sine wave motion for cell-find mode, and connecting said sawtooth wave generator means to energize said optical scanner to sweep said mirror in a sawtooth motion for auto-focus mode.

14. The invention according to claim 12 in which said control means is a microprocessor.

15. An automatic cell-find system for use in a scanning microscope which includes both an objective lens and an adjustable stage means, the system comprising:

slide supporting stage means adjustable in the $x$ and $y$ axis by $x$ and $y$ motors;

light source means providing a light beam through said stage means and said objective lens to beam utilizing means;

an optical scanner intercepting a part of the light beam and directing it into light responsive means, said scanner comprising a galvanometer movement having a mirror attached, said mirror pivoted to be oscillated in the $x$ direction scanning across the scene of a microscope slide to scan for information for cell-find;

sine wave generator means connected to energize said optical scanner galvanometer movement with sine wave energy;

mirror position sensing means connected with said optical scanner for providing an analog electrical signal output representative of mirror position;

analog to digital converter means, said converter means having a signl input terminal and having a strobe terminal for actuating said converter to accept the analog information at said signal input terminal upon the occurrence of a strobe pulse;

means connecting said mirror position signal to said converter means signal input terminal;

means causing said $x$ and $y$ motor to drive said stage in a predetermined meander path during cell-find;

light responsive means receiving the light beam from said mirror and providing an electrical output signal the level of which is representative of light intensity received;

signal level comparator means receiving said second electrical output signal and providing an output pulse when said sweep crosses an area of desired optical density such as a leukocyte; and means for applying a strobe pulse to said converter means upon the occurrence of a leukocyte produced pulse so that the mirror position and thereby the leukocyte x coordinate position along the sweep is recorded.

16. The invention according to claim 15 in which the center of the x-direction scan lies on the meander path and further having apparatus for automatic centering of a leukocyte in the scan by adjusting the position of the microscope stage means, comprising:
  means for calculating the distance the leukocyte x coordinate position lies off the meander path;
  means for issuing a command to said x motor to drive away from the meander path the calculated distance to thereby center the leukocyte in the scan;
  means for storing the calculated distance for use in returning to said meander path; and
  means for using the stored calculated distance to return the system to the meander path before cell-find recommences.

17. The invention according to claim 16 in which the means for calculating comprises:
  means for subtracting from a number $m$ indicating scan center the leukocyte x coordinate position $n$, the subtracted remainder $(m-n)$ being positive $(+)$, negative $(-)$, or zero $(0)$ depending on the magnitude of the number relative to $m$, the sign of the remainder indicating the direction the motor is to be driven and the number of the remainder indicating the distance.

18. An automatic focusing system for use with an optical system which includes both an objective lens means and mounting means for an object to be viewed, said automatic focusing system comprising:
  light responsive means providing an electrical signal which is a function of the light intensity falling thereon;
  oscillating galvanometer mirror scanning means, said mirror oscillating in the x axis intercepting at least a part of the light beam collected by said objective lens means and directing it to said light responsive means, said scanning means providing a repetitive scan across the field of view of said objective lens means;
  aperture means comprising a light shield having a single aperture mounted in front of said light responsive means between said scanning means and said light responsive means;
  sawtooth wave generator means;
  means connecting said sawtooth wave generator means to said oscillating galvanometer mirror scanning means in energizing relation thereto to repetitively oscillate said mirror in a sawtooth motion;
  light intensity to electrical signal level transducer means including said light responsive means to provide an output signal with each optical scan;
  actuator means controllable to adjust the distance between said mounting means and said objective lens means to accomplish proper focus, said actuator means being caused to adjust said distance through a scheduled range while said repetitive scans are proceding; and
  comparator - controller means connected to compare succeding output signals of said transducer means with the previous signal, said means comprising:
  means for sampling and temporarily storing said plurality of transducer means output signals as well as the lens means - mounting means distance associated with each signal;
  means for comparing the magnitude of each sampled transducer means output signal with the previous signal and for keeping the signal of maximum magnitude which represents optimum focus position; and
  means for resetting to the lens means - mounting means distance position of maximum signal representing optimum focus.

19. The invention according to claim 18 in which said scanning means is an optical scanning means comprising an oscillating mirror, said mirror oscillating in the x axis and directing the intercepted light beam on to said light responsive means.

20. The invention according to claim 19 in which said oscillating mirror is part of a galvanometer structure.

21. The invention according to claim 18 in which said light intensity to electrical signal level transducer means is a light intensity rate of change to electrical signal level transducer means and is responsive only to light intensity rate of change to provide an output signal, the magnitude of which signal is a function of the rate of change in light intensity received by said light responsive means.

22. The invention according to claim 21 in which said light intensity rate of change to voltage transducer means further includes, differentiating means responsive to each rate of change in the level of electrical output, the differentiating means providing output pulses the magnitudes of which are a function of the light intensity rate of change during a scan.

23. The invention according to claim 22 in which said light intensity rate of change to voltage transducer means further includes integrating means connected to said differentiating means output to receive and integrate the differentiated pulses of each auto-focus scan to provide an output voltage at the end of each scan which is a summation of the differentiated pulses during said scan.

24. The invention according to claim 23 in which said light intensity rate of change to voltage transducer means further includes integrator reset means for resetting said integrating means before commencing each auto-focus scan.

25. The invention according to claim 23 in which said light intensity rate of change to voltage transducer means also includes an analog to digital converter receiving the integrated output voltage and converting it to a digital value at the end of each scan.

26. The invention according to claim 18 in which said actuator means further comprises:
  control means causing the actuator to first drive the mounting means slightly away from the last good-focus-position, then to drive the stage back through the last good-focus-position and slightly beyond while the scanner provides repetitive auto-focus sweeps to determine focus, means recording the signal indicative of focus from each of the successive sweeps, the maximum amplitude signal indicating good-focus-position, said z actuator control means in response to the recorded signals, then causing the z actuator to move to the new good-focus-position.

27. In a scanning automated microscope system, in which the center of the x-direction scan lies on the meander path, a process of centering a slide mounted leukocyte in the microscope optics by adjusting the position of a microscope stage comprising the steps of:

a. providing an electrical signal which changes in magnitude as a function of scan position, center scan having a signal magnitude $m$;

b. determining leukocyte position along the scan line by measuring the signal magnitude at leukocyte intercept;

c. calculating the distance the position of the leukocyte lies off the meander path;

d. using the calculated number from step c. to determine the command necessary to move from the meander path to leukocyte centered position; and e. issuing a command to slide stage adjusting motor means.

28. A process according to claim 27 in which step a. is in providing an analog signal and the process further including the step of:

a. converting the analog signal to a digital value representative of leukocyte position.

29. The process according to claim 28 in which the center scan position $m$ is a digital number, and the calculating step c comprises:

subtracting magnitude $m$ from the digital value representative of leukocyte position, the substracted remainder being positive (+), negative (−), or zero (0) depending upon the magnitude of the number relative to $m$.

30. In a scanning automated microscope system, having slide mounting means adjustable in the $x$ and $y$ axis for positioning the slide under the microscope and in the $z$ axis for focus, and in which a light beam is directed through the microscope optics and slide, a process of cell-find, cell centering, and auto-focus comprising the steps of:

1. cell-find comprising the steps of;
   a. driving the stage in the $y$ axis along a meander path while searching for leukocytes;
   b. scanning repetitively across the light beam in the $x$ axis as step $a$. above is occurring, said scanning being astride said meander path and projecting said scanned beam on light responsive means;
   c. providing an electrical signal level ramp proportional to scan position;
   d. identifying a found leukocyte by reason of the opacity of its nucleus causing a diminution of the light reaching said light responsive means;
   e. determining leukocyte position along the scan line by measuring the signal level at leukocyte intercept;
   f. stopping the $y$ axis drive upon identifying a leukocyte;

2. cell centering comprising the steps of;
   a. calculating the distance the leukocyte lies off the meander path;
   b. using the calculated distance from step $a$. to determine the command necessary to move from the meander path to leukocyte centered position; and
   c. issuing a command to $x$ axis stage adjusting motor means if the cell is not already approximately centered;

3. and, auto-focus comprising the steps of:
   a. adjusting the position of the slide mounting means in the $z$ axis in a predetermined sequence during focus so that said position is changing, while;
   b. scanning repetitively the same slide location and providing an output signal with each of said scans while said predetermined sequence of adjusting is occurring;
   c. comparing the magnitude of the output signal of each succeeding scan with the magnitude of the previously preserved scan and preserving only the largest of the two newly compared signals;
   d. recording the $z$ coordinate location of the preserved scan of step $c$. above; and
   e. readjusting the position of the slide mounting means to the $z$ coordinate location of the preserved scan representing the position of optimum focus.

31. A process according to claim 30 wherein step 3.$b$. comprises the steps of:

a. differentiating signal intensity rate of change to provide an output pulse with each rate of change, and b. integrating said differentiated pulses to provide said output signal with each of said scans.

32. The process according to claim 30 and further including a process of accepting a plurality of leukocytes in a single scan comprising after step 1.$e$., the additional steps of:

g. loading the leukocyte position into a register;

h. repeating steps 1.$d$., 1.$e$., and $g$. for each of said additional luekocytes;

i. storing in a counter the number of leukocytes identified;

j. selecting one of said leukocytes, centering on it according to step 2 and auto focusing according to step 3; and, k. repeating step $j$. until the selected leukocytes equal in number the number stored in the counter.

* * * * *

UNITED STATES PATENT OFFICE
CERTIFICATE OF CORRECTION

PATENT NO. : 4,000,417
DATED : December 28, 1976
INVENTOR(S) : William M. Adkisson, Gerald D. Hunter,
William M. Papic, Wayne L. Walters It is certified that error appears in the above-identified patent and that said Letters Patent are hereby corrected as shown below:

In claim 1, line 22, "and" should be --said--.

In claim 1, line 38, "for" (second occurrence) should be --from--.

Claim 5, line 33, "incention" should be --invention--.

Claim 12, line 5, change "in scanning" to --in a scanning--.

Claim 12, line 15, change "into" to --onto--.

Claim 12, line 64, "long" should be --along--.

Claim 15, line 37, change "into" to --onto--.

Signed and Sealed this

Twenty-fourth Day of May 1977

[SEAL]

Attest:

RUTH C. MASON
*Attesting Officer*

C. MARSHALL DANN
*Commissioner of Patents and Trademarks*